US008513006B2

(12) United States Patent
Ross et al.

(10) Patent No.: US 8,513,006 B2
(45) Date of Patent: Aug. 20, 2013

(54) TETRAVALENT INFLUENZA VACCINE AND USE THEREOF

(75) Inventors: Ted M. Ross, Pittsburgh, PA (US); Xianchun Tang, West Roxbury, MA (US); Hairong Lu, West Roxbury, MA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 74 days.

(21) Appl. No.: 13/230,291

(22) Filed: Sep. 12, 2011

(65) Prior Publication Data

US 2012/0064117 A1 Mar. 15, 2012

Related U.S. Application Data

(60) Provisional application No. 61/382,766, filed on Sep. 14, 2010.

(51) Int. Cl.
 *C12N 15/44* (2006.01)
 *A61K 39/145* (2006.01)
 *C12N 15/00* (2006.01)

(52) U.S. Cl.
 USPC .................. 435/320.1; 240/202.1; 240/93.1

(58) Field of Classification Search
 None
 See application file for complete search history.

(56) References Cited

U.S. PATENT DOCUMENTS

| | | | |
|---|---|---|---|
| 5,762,939 | A | 6/1998 | Smith et al. |
| 5,858,368 | A | 1/1999 | Smith et al. |
| 6,245,532 | B1 | 6/2001 | Smith et al. |
| 2008/0003203 | A1 | 1/2008 | Hu et al. |
| 2009/0175909 | A1 | 7/2009 | Yang et al. |
| 2010/0074916 | A1 | 3/2010 | Nabel et al. |
| 2010/0129401 | A1 | 5/2010 | Smith et al. |

FOREIGN PATENT DOCUMENTS

| | | |
|---|---|---|
| WO | WO 96/16184 | 5/1996 |
| WO | WO 2004/022760 | 3/2004 |
| WO | WO 2009/020236 | 2/2009 |

OTHER PUBLICATIONS

Boublik et al., "Eukaryotic Virus Display: Engineering the Major Surface Glycoprotein of the *Autographa californica* Nuclear Polyhedrosis Virus (AcNPV) for the Presentation of Foreign Proteins on the Virus Surface," *Biotechnology* (NY), vol. 13:1079-1084, 1995.
Fan et al., "Construction and Immunogenicity of Recombinant Pseudotype Baculovirus Expressing the Capsid Protein of Porcine Circovirus Type 2 in Mice," *J. Virol. Methods*, vol. 150:21-26, 2008.
Feng et al., "Baculovirus Surface Display of SARS Coronavirus (SARS-CoV) Spike Protein and Immunogenicity of the Displayed Protein in Mice Models," *DNA Cell Biol.*, vol. 25:668-673, 2006.
Gheysen et al., "Assembly and Release of HIV-1 Precursor Pr55$^{gag}$ Virus-Like Particles from Recombinant Baculovirus-Infected Insect Cells," *Cell*, vol. 59:103-112, 1989.
Huber et al., "A Multi-Valent Vaccine Approach that Elicits Broad Immunity within an Influenza Subtype," *Vaccine*, vol. 27:1192-1200, 2009.
Jin et al., "Safety and Immunogenicity of H5N1 Influenza Vaccine Based on Baculovirus Surface Display System of *Bombyx mori*," *PLoS ONE*, vol. 3:e3933, 2008.
Kirnbauer et al., "Efficient Self-Assembly of Human Papillomavirus Type 16 L1 and L1-L2 into Virus-Like Particles," *J. Virol.*, vol. 67:6929-6936, 1993.
Kitagawa et al., "Ligand-Directed Gene Targeting to Mammalian Cells by Pseudotype Baculoviruses," *J. Virol.*, vol. 79:3639-3652, 2005.
Kost et al., "Baculovirus as Versatile Vectors for Protein Expression in Insect and Mammalian Cells," *Nat. Biotechnol.*, vol. 23:567-575, 2005.
Latham et al., "Formation of Wild-Type and Chimeric Influenza Virus-Like Particles following Simultaneous Expression of Only Four Structural Proteins," *J. Virol.*, vol. 75:6154-6165, 2001.
Lin et al., "Baculovirus Surface Display of σC and σB Proteins of Avian Reovirus and Immunogenicity of the Displayed Proteins in a Mouse Mode," *Vaccine*, vol. 26:6361-6367, 2008.
Lu et al., "Baculovirus Surface-Displayed Hemagglutinin of H5N1 Influenza Virus Sustains its Authentic Cleavage, Hemagglutination Activity, and Antigenicity," *Biochem. Biophys. Res. Commun.*, vol. 358:404-409, 2007. (Retracted).
McMichael et al., "Cytotoxic T-Cell Immunity to Influenza," *N. Engl. J. Med.*, vol. 309:13-17, 1983.
Oker-Blom et al., "Baculovirus Display Strategies: Emerging Tools for Eukaryotic Libraries and Gene Delivery," *Brief Funct. Genomic Proteomic*, vol. 2:244-253, 2003.

(Continued)

*Primary Examiner* — Bao Li
(74) *Attorney, Agent, or Firm* — Klarquist Sparkman, LLP

(57) ABSTRACT

Disclosed herein is the finding that baculovirus display of multiple influenza virus hemagglutinin (HA) proteins elicits broadly reactive immune responses against influenza. Thus provided herein are recombinant baculovirus vectors having a first, second, third and fourth nucleic acid sequence, each encoding an influenza hemagglutinin (HA) fusion protein. The first, second, third and fourth nucleic acid sequences each encode an influenza HA with a different amino acid sequence. Also provided are recombinant baculoviruses displaying a first, second, third and fourth influenza virus HA fusion protein in the baculovirus envelope, wherein each HA fusion protein comprises a different HA amino acid sequence. Tetravalent influenza virus vaccines comprising the recombinant baculoviruses disclosed herein are further provided. In addition, methods of immunizing a subject against influenza virus using the tetravalent influenza virus vaccines are provided. In particular examples of the compositions and methods disclosed herein, the HA polypeptides are from H5N1 influenza virus.

19 Claims, 13 Drawing Sheets

(56) References Cited

OTHER PUBLICATIONS

Peralta et al., "A Chimeric Baculovirus Displaying Bovine Herpesvirus-1 (BHV-1) Glycoprotein D on its Surface and their Immunological Properties," *Appl. Microbiol. Biotechnol.*, vol. 75:407-414, 2007.

Prabakaran et al., "Protective Immunity against Influenza H5N1 Virus Challenge in Mice by Intranasal Co-Administration of Baculovirus Surface-Displayed HA and Recombinant CTB as an Adjuvant," *Virology*, vol. 380:412-420, 2008.

Prabakaran et al., "Gastrointestinal Delivery of Baculovirus Displaying Influenza Virus Hemagglutinin Protects Mice against Heterologous H5N1 Infection," *J. Virol.*, vol. 84:3201-3209, 2010.

Prabakaran et al., "Reverse Micelle-Encapsulated Recombinant Baculovirus as an Oral Vaccine against H5N1 Infection in Mice," *Ant. Res.*, vol. 86:180-187, 2010.

Strauss et al., "Baculovirus-Based Vaccination Vectors Allow for Efficient Induction of Immune Responses Against *Plasmodium falciparum* Circumsporozoite Protein," *Mol. Ther.*, vol. 15:193-202, 2007.

Yang et al., "Avian Influenza Virus Hemagglutinin Display on Baculovirus Envelope: Cytoplasmic Domain Affects Virus Properties and Vaccine Potential," *Mol. Ther.*, vol. 15:989-996, 2007.

Yoshida et al., "A Baculovirus Dual Expression System-Based Malaria Vaccine Induces Strong Protection against *Plasmodium berghei* Sporozoite Challenge in Mice," *Infect. Immun.*, vol. 77:1782-1789, 2009.

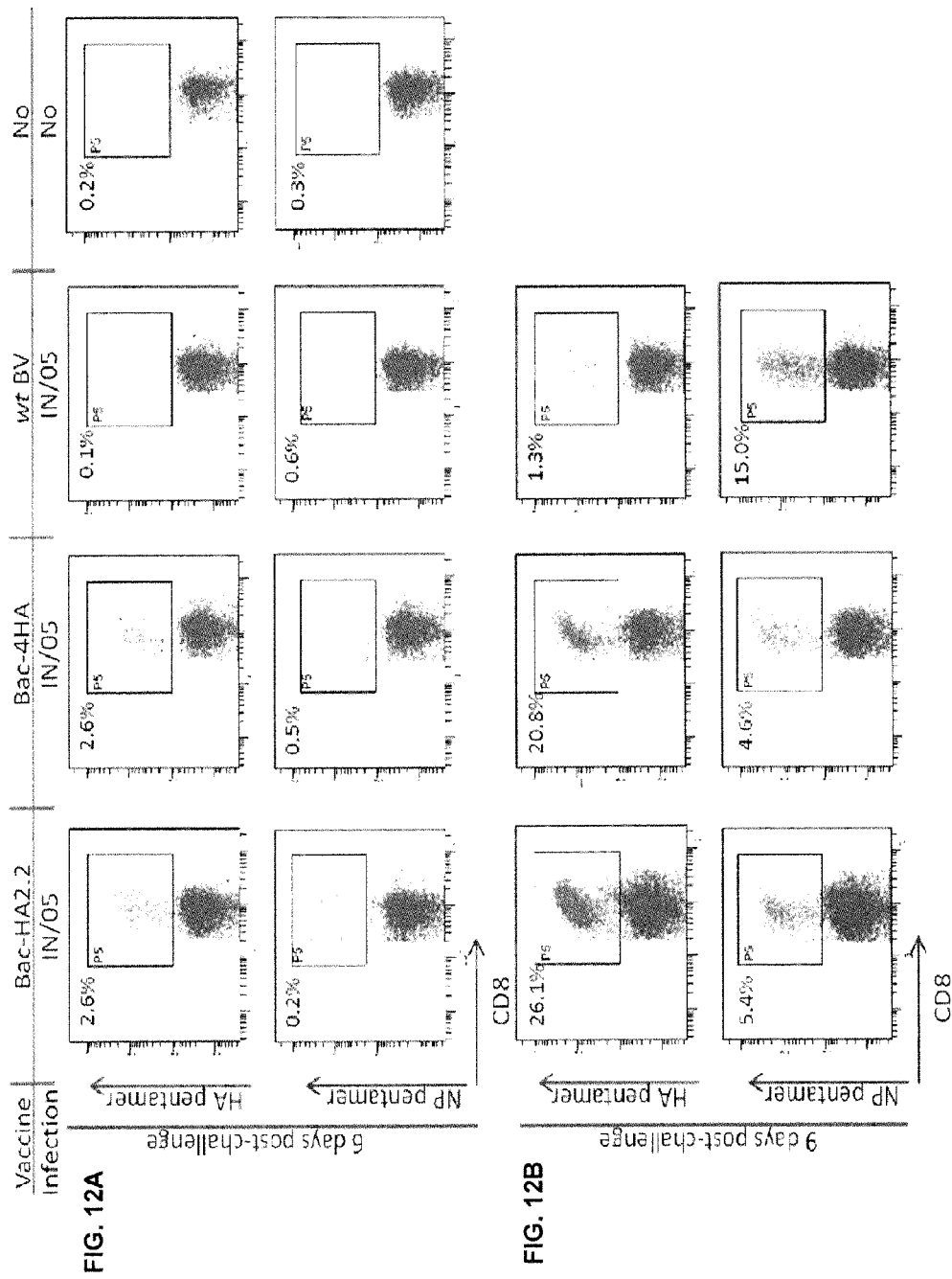

SEQUENCE LISTING

```
<160> NUMBER OF SEQ ID NOS: 18

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 1
cgctgatcag ccaccatgct actggtaaat cagtcacac                              39

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 2
cgagctcgtc gacaggcctg aattcggatc ccgcaaaggc agaatgcgcc                  50

<210> SEQ ID NO 3
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 3
caggcctgtc gacgagctcg cggccgcgtt catgtttggt catgtag                     47

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 4
aagcggccgt taatattgtc tattacggtt tctaatc                                37

<210> SEQ ID NO 5
<211> LENGTH: 37
```

```
<212> TYPE: DNA
<213> ORGANISM: Artificial Sequence
<220> FEATURE:
<223> OTHER INFORMATION: Synthetic oligonucleotide

<400> SEQUENCE: 5
caagtcgacg ccaccatgaa ggcaaaccta ctggtcc                              37

<210> SEQ ID NO 6
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 6
ctcgcggccg ctcagatgca tattctgcac tgc                                  33

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
gcgggatccg cagacacaat atgtataggc                                      30

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8
aacgcggccg caatctgata gatccccatt gattc                                35

<210> SEQ ID NO 9
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 9
ggctctagat taatattgtc tattacggtt tctacacatc agaaactga ttgc             54

<210> SEQ ID NO 10
<211> LENGTH: 1788
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1788)
<220> FEATURE:
<221> NAME/KEY: misc_feature
<222> LOCATION: (1)..(114)
<223> OTHER INFORMATION: gp64 signal peptide
<220> FEATURE:
<221> NAME/KEY: misc_feature
<222> LOCATION: (118)..(141)
<223> OTHER INFORMATION: Flag tag
<220> FEATURE:
<221> NAME/KEY: misc_feature
<222> LOCATION: (142)..(147)
<223> OTHER INFORMATION: XhoI restriction site
<220> FEATURE:
```

```
<221> NAME/KEY: misc_feature
<222> LOCATION: (148)..(1764)
<223> OTHER INFORMATION: HA ectodomain and transmembrane domain
<220> FEATURE:
<221> NAME/KEY: misc_feature
<222> LOCATION: (1765)..(1788)
<223> OTHER INFORMATION: gp64 cytoplasmic tail domain

<400> SEQUENCE: 10 atg cta ctg gta aat cag tca cac caa ggc ttc aat aag gaa cac aca        48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg        96
Ser Lys Met Val Ser Ala Ile Val Leu Tyr Val Leu Leu Ala Ala Ala
            20                  25                  30 gcg cat tct gcc ttt gcg gtc gac tac aaa gac gat gac gac aag ctc       144
Ala His Ser Ala Phe Ala Val Asp Tyr Lys Asp Asp Asp Asp Lys Leu
        35                  40                  45 gag gat cag att tgc att ggt tac cat gca aac aac tcg aca gag cag       192
Glu Asp Gln Ile Cys Ile Gly Tyr His Ala Asn Asn Ser Thr Glu Gln
50                  55                  60 gtt gac aca ata atg gaa aag aac gtt act gtt aca cat gcc caa gac       240
Val Asp Thr Ile Met Glu Lys Asn Val Thr Val Thr His Ala Gln Asp
65                  70                  75                  80 ata ctg gaa aag aaa cac aac ggg aag ctc tgc gat cta gat gga gtg       288
Ile Leu Glu Lys Lys His Asn Gly Lys Leu Cys Asp Leu Asp Gly Val
                85                  90                  95 aag cct cta att ttg aga gat tgt agc gta gct gga tgg ctc ctc gga       336
Lys Pro Leu Ile Leu Arg Asp Cys Ser Val Ala Gly Trp Leu Leu Gly
            100                 105                 110 aac cca atg tgt gac gaa ttc atc aat gtg ccg gaa tgg tct tac ata       384
Asn Pro Met Cys Asp Glu Phe Ile Asn Val Pro Glu Trp Ser Tyr Ile
        115                 120                 125 gtg gag aag gcc aat cca gtc aat gac ctc tgt tac cca ggg gat ttc       432
Val Glu Lys Ala Asn Pro Val Asn Asp Leu Cys Tyr Pro Gly Asp Phe
130                 135                 140 aat gac tat gaa gaa ttg aaa cac cta ttg agc aga ata aac cat ttt       480
Asn Asp Tyr Glu Glu Leu Lys His Leu Leu Ser Arg Ile Asn His Phe
145                 150                 155                 160 gag aaa att cag atc atc ccc aaa agt tct tgg tcc agt cat gaa gcc       528
Glu Lys Ile Gln Ile Ile Pro Lys Ser Ser Trp Ser Ser His Glu Ala
                165                 170                 175 tca tta ggg gtg agc tca gca tgt cca tac cag gga aag tcc tcc ttt       576
Ser Leu Gly Val Ser Ser Ala Cys Pro Tyr Gln Gly Lys Ser Ser Phe
            180                 185                 190 ttc aga aat gtg gta tgg ctt atc aaa aag aac agt aca tac cca aca       624
Phe Arg Asn Val Val Trp Leu Ile Lys Lys Asn Ser Thr Tyr Pro Thr
        195                 200                 205 ata aag agg agc tac aat aat acc aac caa gaa gat ctt ttg gta ctg       672
Ile Lys Arg Ser Tyr Asn Asn Thr Asn Gln Glu Asp Leu Leu Val Leu
210                 215                 220 tgg ggg att cac cat cct aat gat gcg gca gag cag aca aag ctc tat       720
Trp Gly Ile His His Pro Asn Asp Ala Ala Glu Gln Thr Lys Leu Tyr
225                 230                 235                 240 caa aac cca acc acc tat att tcc gtt ggg aca tca aca cta aac cag       768
Gln Asn Pro Thr Thr Tyr Ile Ser Val Gly Thr Ser Thr Leu Asn Gln
                245                 250                 255 aga ttg gta cca aga ata gct act aga tcc aaa gta aac ggg caa agt       816
Arg Leu Val Pro Arg Ile Ala Thr Arg Ser Lys Val Asn Gly Gln Ser
            260                 265                 270 gga agg atg gag ttc ttc tgg aca att tta aag ccg aat gat gca atc       864
Gly Arg Met Glu Phe Phe Trp Thr Ile Leu Lys Pro Asn Asp Ala Ile
```

```
                 275                 280                 285
aac ttc gag agt aat gga aat ttc att gct cca gaa tat gca tac aaa       912
Asn Phe Glu Ser Asn Gly Asn Phe Ile Ala Pro Glu Tyr Ala Tyr Lys
290                 295                 300 att gtc aag aaa ggg gac tca aca att atg aaa agt gaa ttg gaa tat       960
Ile Val Lys Lys Gly Asp Ser Thr Ile Met Lys Ser Glu Leu Glu Tyr
305                 310                 315                 320 ggt aac tgc aac acc aag tgt caa act cca atg ggg gcg ata aac tct      1008
Gly Asn Cys Asn Thr Lys Cys Gln Thr Pro Met Gly Ala Ile Asn Ser
                325                 330                 335 agc atg cca ttc cac aat ata cac cct ctc acc att ggg gaa tgc ccc      1056
Ser Met Pro Phe His Asn Ile His Pro Leu Thr Ile Gly Glu Cys Pro
            340                 345                 350 aaa tat gtg aaa tca aac aga tta gtc ctt gcg act ggg ctc aga aat      1104
Lys Tyr Val Lys Ser Asn Arg Leu Val Leu Ala Thr Gly Leu Arg Asn
        355                 360                 365 agc cct caa aga gag aga aga aaa aag aga gga tta ttt gga gct          1152
Ser Pro Gln Arg Glu Arg Arg Lys Lys Arg Gly Leu Phe Gly Ala
370                 375                 380 ata gca ggt ttt ata gag gga gga tgg cag gga atg gta gat ggt tgg      1200
Ile Ala Gly Phe Ile Glu Gly Gly Trp Gln Gly Met Val Asp Gly Trp
385                 390                 395                 400 tat ggg tac cac cat agc aat gag cag ggg agt ggg tac gct gca gac      1248
Tyr Gly Tyr His His Ser Asn Glu Gln Gly Ser Gly Tyr Ala Ala Asp
                405                 410                 415 aaa gaa tcc act caa aag gca ata gat gga gtc acc aat aag gtc aac      1296
Lys Glu Ser Thr Gln Lys Ala Ile Asp Gly Val Thr Asn Lys Val Asn
            420                 425                 430 tcg atc att gac aaa atg aac act cag ttt gag gcc gtt gga agg gaa      1344
Ser Ile Ile Asp Lys Met Asn Thr Gln Phe Glu Ala Val Gly Arg Glu
        435                 440                 445 ttt aac aac tta gaa agg aga ata gag aat tta aac aag aag atg gaa      1392
Phe Asn Asn Leu Glu Arg Arg Ile Glu Asn Leu Asn Lys Lys Met Glu
450                 455                 460 gac ggg ttc cta gat gtc tgg act tat aat gct gaa ctt ctg gtt ctc      1440
Asp Gly Phe Leu Asp Val Trp Thr Tyr Asn Ala Glu Leu Leu Val Leu
465                 470                 475                 480 atg gaa aat gag aga act cta gac ttt cat gac tca aat gtc aag aac      1488
Met Glu Asn Glu Arg Thr Leu Asp Phe His Asp Ser Asn Val Lys Asn
                485                 490                 495 ctt tac gac aag gtc cga cta cag ctt agg gat aat gca aag gag ctg      1536
Leu Tyr Asp Lys Val Arg Leu Gln Leu Arg Asp Asn Ala Lys Glu Leu
            500                 505                 510 ggt aac ggt tgt ttc gag ttc tat cat aaa tgt gat aat gaa tgt atg      1584
Gly Asn Gly Cys Phe Glu Phe Tyr His Lys Cys Asp Asn Glu Cys Met
        515                 520                 525 gaa agt gta aga aat gga acg tat gac tac ccg cag tat tca gaa gaa      1632
Glu Ser Val Arg Asn Gly Thr Tyr Asp Tyr Pro Gln Tyr Ser Glu Glu
530                 535                 540 gcg cta aaa aga gag gaa ata agt gga gta aaa ttg gaa tca ata          1680
Ala Arg Leu Lys Arg Glu Glu Ile Ser Gly Val Lys Leu Glu Ser Ile
545                 550                 555                 560 gga att tac caa ata ctg tca att tat tct aca gtg gcg agt tcc cta      1728
Gly Ile Tyr Gln Ile Leu Ser Ile Tyr Ser Thr Val Ala Ser Ser Leu
                565                 570                 575 gca ctg gca atc atg gta gct ggt cta tcc tta tgg aga aac cgt aat      1776
Ala Leu Ala Ile Met Val Ala Gly Leu Ser Leu Trp Arg Asn Arg Asn
            580                 585                 590 aga caa tat taa                                                      1788
Arg Gln Tyr
```

-continued

```
                      595

<210> SEQ ID NO 11
<211> LENGTH: 595
<212> TYPE: PRT
<213> ORGANISM: Artificial Sequence
<220> FEATURE:
<223> OTHER INFORMATION: Synthetic Construct

<400> SEQUENCE: 11

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Val Asp Tyr Lys Asp Asp Asp Lys Leu
        35                  40                  45

Glu Asp Gln Ile Cys Ile Gly Tyr His Ala Asn Asn Ser Thr Glu Gln
    50                  55                  60

Val Asp Thr Ile Met Glu Lys Asn Val Thr Val Thr His Ala Gln Asp
65                  70                  75                  80

Ile Leu Glu Lys Lys His Asn Gly Lys Leu Cys Asp Leu Asp Gly Val
                85                  90                  95

Lys Pro Leu Ile Leu Arg Asp Cys Ser Val Ala Gly Trp Leu Leu Gly
            100                 105                 110

Asn Pro Met Cys Asp Glu Phe Ile Asn Val Pro Glu Trp Ser Tyr Ile
        115                 120                 125

Val Glu Lys Ala Asn Pro Val Asn Asp Leu Cys Tyr Pro Gly Asp Phe
    130                 135                 140

Asn Asp Tyr Glu Glu Leu Lys His Leu Leu Ser Arg Ile Asn His Phe
145                 150                 155                 160

Glu Lys Ile Gln Ile Ile Pro Lys Ser Ser Trp Ser His Glu Ala
                165                 170                 175

Ser Leu Gly Val Ser Ser Ala Cys Pro Tyr Gln Gly Lys Ser Ser Phe
            180                 185                 190

Phe Arg Asn Val Val Trp Leu Ile Lys Lys Asn Ser Thr Tyr Pro Thr
        195                 200                 205

Ile Lys Arg Ser Tyr Asn Asn Thr Asn Gln Glu Asp Leu Leu Val Leu
    210                 215                 220

Trp Gly Ile His His Pro Asn Asp Ala Ala Glu Gln Thr Lys Leu Tyr
225                 230                 235                 240

Gln Asn Pro Thr Thr Tyr Ile Ser Val Gly Thr Ser Thr Leu Asn Gln
                245                 250                 255

Arg Leu Val Pro Arg Ile Ala Thr Arg Ser Lys Val Asn Gly Gln Ser
            260                 265                 270

Gly Arg Met Glu Phe Phe Trp Thr Ile Leu Lys Pro Asn Asp Ala Ile
        275                 280                 285

Asn Phe Glu Ser Asn Gly Asn Phe Ile Ala Pro Glu Tyr Ala Tyr Lys
    290                 295                 300

Ile Val Lys Lys Gly Asp Ser Thr Ile Met Lys Ser Glu Leu Glu Tyr
305                 310                 315                 320

Gly Asn Cys Asn Thr Lys Cys Gln Thr Pro Met Gly Ala Ile Asn Ser
                325                 330                 335

Ser Met Pro Phe His Asn Ile His Pro Leu Thr Ile Gly Glu Cys Pro
            340                 345                 350

Lys Tyr Val Lys Ser Asn Arg Leu Val Leu Ala Thr Gly Leu Arg Asn
        355                 360                 365
```

```
Ser Pro Gln Arg Glu Arg Arg Lys Lys Arg Gly Leu Phe Gly Ala
    370                 375                 380

Ile Ala Gly Phe Ile Glu Gly Trp Gln Gly Met Val Asp Gly Trp
385                 390                 395                 400

Tyr Gly Tyr His His Ser Asn Glu Gln Gly Ser Gly Tyr Ala Ala Asp
                405                 410                 415

Lys Glu Ser Thr Gln Lys Ala Ile Asp Gly Val Thr Asn Lys Val Asn
                420                 425                 430

Ser Ile Ile Asp Lys Met Asn Thr Gln Phe Glu Ala Val Gly Arg Glu
                435                 440                 445

Phe Asn Asn Leu Glu Arg Arg Ile Glu Asn Leu Asn Lys Lys Met Glu
    450                 455                 460

Asp Gly Phe Leu Asp Val Trp Thr Tyr Asn Ala Glu Leu Leu Val Leu
465                 470                 475                 480

Met Glu Asn Glu Arg Thr Leu Asp Phe His Asp Ser Asn Val Lys Asn
                485                 490                 495

Leu Tyr Asp Lys Val Arg Leu Gln Leu Arg Asp Asn Ala Lys Glu Leu
                500                 505                 510

Gly Asn Gly Cys Phe Glu Phe Tyr His Lys Cys Asp Asn Glu Cys Met
    515                 520                 525

Glu Ser Val Arg Asn Gly Thr Tyr Asp Tyr Pro Gln Tyr Ser Glu Glu
    530                 535                 540

Ala Arg Leu Lys Arg Glu Glu Ile Ser Gly Val Lys Leu Glu Ser Ile
545                 550                 555                 560

Gly Ile Tyr Gln Ile Leu Ser Ile Tyr Ser Thr Val Ala Ser Ser Leu
                565                 570                 575

Ala Leu Ala Ile Met Val Ala Gly Leu Ser Leu Trp Arg Asn Arg Asn
                580                 585                 590

Arg Gln Tyr
        595

<210> SEQ ID NO 12
<211> LENGTH: 1782
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1782)
<220> FEATURE:
<221> NAME/KEY: misc_feature
<222> LOCATION: (1)..(114)
<223> OTHER INFORMATION: gp64 signal peptide
<220> FEATURE:
<221> NAME/KEY: misc_feature
<222> LOCATION: (115)..(135)
<223> OTHER INFORMATION: His tag
<220> FEATURE:
<221> NAME/KEY: misc_feature
<222> LOCATION: (136)..(141)
<223> OTHER INFORMATION: BamHI restriction site
<220> FEATURE:
<221> NAME/KEY: misc_feature
<222> LOCATION: (142)..(1758)
<223> OTHER INFORMATION: HA ectodomain and transmembrane domain
<220> FEATURE:
<221> NAME/KEY: misc_feature
<222> LOCATION: (1759)..(1782)
<223> OTHER INFORMATION: gp64 cytoplasmic tail domain

<400> SEQUENCE: 12 atg cta ctg gta aat cag tca cac caa ggc ttc aat aag gaa cac aca      48
```

```
        Met Leu Leu Val Asn Gln Ser His Gln Gly Phe Asn Lys Glu His Thr
        1               5                   10                  15 agc aag atg gta agc gct att gtt tta tat gtg ctt ttg gcg gcg gcg         96
Ser Lys Met Val Ser Ala Ile Val Leu Tyr Val Leu Leu Ala Ala Ala
            20                  25                  30 gcg cat tct gcc ttt gcg cat cac cac cat cac cac gga tcc gat            144
Ala His Ser Ala Phe Ala His His His His His His Gly Ser Asp
        35                  40                  45 cag att tgc att ggt tac cat gca aac aat tca aca gag cag gtt gac        192
Gln Ile Cys Ile Gly Tyr His Ala Asn Asn Ser Thr Glu Gln Val Asp
50                  55                  60 aca atc atg gaa aag aac gtt act gtt aca cat gcc caa gac ata ctg        240
Thr Ile Met Glu Lys Asn Val Thr Val Thr His Ala Gln Asp Ile Leu
65                  70                  75                  80 gaa aag aca cac aac ggg aag ctc tgc gat cta gat gga gtg aag cct        288
Glu Lys Thr His Asn Gly Lys Leu Cys Asp Leu Asp Gly Val Lys Pro
            85                  90                  95 cta att tta aga gat tgt agt gta gct gga tgg ctc ctc ggg aac cca        336
Leu Ile Leu Arg Asp Cys Ser Val Ala Gly Trp Leu Leu Gly Asn Pro
            100                 105                 110 atg tgt gac gaa ttc atc aat gta ccg gaa tgg tct tac ata gtg gag        384
Met Cys Asp Glu Phe Ile Asn Val Pro Glu Trp Ser Tyr Ile Val Glu
            115                 120                 125 aag gcc aat cca acc aat gac ctc tgt tac cca ggg agt ttc aac gac        432
Lys Ala Asn Pro Thr Asn Asp Leu Cys Tyr Pro Gly Ser Phe Asn Asp
130                 135                 140 tat gaa gaa ctg aaa cac cta ttg agc aga ata aac cat ttt gag aaa        480
Tyr Glu Glu Leu Lys His Leu Leu Ser Arg Ile Asn His Phe Glu Lys
145                 150                 155                 160 att caa atc atc ccc aaa agt tct tgg tcc gat cat gaa gcc tca tca        528
Ile Gln Ile Ile Pro Lys Ser Ser Trp Ser Asp His Glu Ala Ser Ser
            165                 170                 175 gga gtg agc tca gca tgt cca tac ctg gga agt ccc tcc ttt ttt aga        576
Gly Val Ser Ser Ala Cys Pro Tyr Leu Gly Ser Pro Ser Phe Phe Arg
            180                 185                 190 aat gtg gta tgg ctt atc aaa aag aac agt aca tac cca aca ata aag        624
Asn Val Val Trp Leu Ile Lys Lys Asn Ser Thr Tyr Pro Thr Ile Lys
            195                 200                 205 aaa agc tac aat aat acc aac caa gaa gat ctt ttg gta ctg tgg gga        672
Lys Ser Tyr Asn Asn Thr Asn Gln Glu Asp Leu Leu Val Leu Trp Gly
210                 215                 220 att cac cat cct aat gat gcg gca gag cag aca agg cta tat caa aac        720
Ile His His Pro Asn Asp Ala Ala Glu Gln Thr Arg Leu Tyr Gln Asn
225                 230                 235                 240 cca acc acc tat att tcc att ggg aca tca aca cta aac cag aga ttg        768
Pro Thr Thr Tyr Ile Ser Ile Gly Thr Ser Thr Leu Asn Gln Arg Leu
            245                 250                 255 gta cca aaa ata gct act aga tcc aaa gta aac ggg caa agt gga agg        816
Val Pro Lys Ile Ala Thr Arg Ser Lys Val Asn Gly Gln Ser Gly Arg
            260                 265                 270 atg gag ttc ttc tgg aca att tta aaa cct aat gat gca atc aac ttc        864
Met Glu Phe Phe Trp Thr Ile Leu Lys Pro Asn Asp Ala Ile Asn Phe
            275                 280                 285 gag agt aat gga aat ttc att gct cca gaa tat gca tac aaa att gtc        912
Glu Ser Asn Gly Asn Phe Ile Ala Pro Glu Tyr Ala Tyr Lys Ile Val
            290                 295                 300 aag aaa ggg gac tca gca att atg aaa agt gaa ttg gaa tat ggt aac        960
Lys Lys Gly Asp Ser Ala Ile Met Lys Ser Glu Leu Glu Tyr Gly Asn
305                 310                 315                 320 tgc aac acc aag tgt caa act cca atg ggg gcg ata aac tct agt atg       1008
```

```
Cys Asn Thr Lys Cys Gln Thr Pro Met Gly Ala Ile Asn Ser Ser Met
            325                 330                 335 cca ttc cac aac ata cac cct ctc acc atc ggg gaa tgc ccc aaa tat      1056
Pro Phe His Asn Ile His Pro Leu Thr Ile Gly Glu Cys Pro Lys Tyr
                340                 345                 350 gtg aaa tca aac aga tta gtc ctt gca aca ggg ctc aga aat agc cct      1104
Val Lys Ser Asn Arg Leu Val Leu Ala Thr Gly Leu Arg Asn Ser Pro
            355                 360                 365 caa aga gag agc aga aga aaa aag aga gga cta ttt gga gct ata gca      1152
Gln Arg Glu Ser Arg Arg Lys Lys Arg Gly Leu Phe Gly Ala Ile Ala
        370                 375                 380 ggt ttt ata gag gga gga tgg cag gga atg gta gat ggt tgg tat ggg      1200
Gly Phe Ile Glu Gly Gly Trp Gln Gly Met Val Asp Gly Trp Tyr Gly
385                 390                 395                 400 tac cac cat agc aat gag cag ggg agt ggg tac gct gca gac aaa gaa      1248
Tyr His His Ser Asn Glu Gln Gly Ser Gly Tyr Ala Ala Asp Lys Glu
                405                 410                 415 tcc act caa aag gca ata gat gga gtc acc aat aag gtc aac tca atc      1296
Ser Thr Gln Lys Ala Ile Asp Gly Val Thr Asn Lys Val Asn Ser Ile
            420                 425                 430 att gac aaa atg aac act cag ttt gag gcc gtt gga agg gaa ttt aat      1344
Ile Asp Lys Met Asn Thr Gln Phe Glu Ala Val Gly Arg Glu Phe Asn
        435                 440                 445 aac tta gaa agg aga ata gag aat tta aac aag aag atg gaa gac ggg      1392
Asn Leu Glu Arg Arg Ile Glu Asn Leu Asn Lys Lys Met Glu Asp Gly
    450                 455                 460 ttt cta gat gtc tgg act tat aat gcc gaa ctt ctg gtt ctc atg gaa      1440
Phe Leu Asp Val Trp Thr Tyr Asn Ala Glu Leu Leu Val Leu Met Glu
465                 470                 475                 480 aat gag aga act cta gac ttt cat gac tca aat gtt aag aac ctc tac      1488
Asn Glu Arg Thr Leu Asp Phe His Asp Ser Asn Val Lys Asn Leu Tyr
                485                 490                 495 gac aag gtc cga cta cag ctt agg gat aat gca aag gag ctg ggt aac      1536
Asp Lys Val Arg Leu Gln Leu Arg Asp Asn Ala Lys Glu Leu Gly Asn
            500                 505                 510 ggt tgt ttc gag ttc tat cac aaa tgt gat aat gaa tgt atg gaa agt      1584
Gly Cys Phe Glu Phe Tyr His Lys Cys Asp Asn Glu Cys Met Glu Ser
        515                 520                 525 ata aga aac gga acg tac aac tat ccg cag tat tca gaa gaa gca aga      1632
Ile Arg Asn Gly Thr Tyr Asn Tyr Pro Gln Tyr Ser Glu Glu Ala Arg
    530                 535                 540 tta aaa aga gag gaa ata agt ggg gta aaa ttg gaa tca ata gga act      1680
Leu Lys Arg Glu Glu Ile Ser Gly Val Lys Leu Glu Ser Ile Gly Thr
545                 550                 555                 560 tac caa ata ctg tca att tat tca aca gtg gcg agt tcc cta gca ctg      1728
Tyr Gln Ile Leu Ser Ile Tyr Ser Thr Val Ala Ser Ser Leu Ala Leu
                565                 570                 575 gca atc atg atg gct ggt cta tct ttg tgg aga aac cgt aat aga caa      1776
Ala Ile Met Met Ala Gly Leu Ser Leu Trp Arg Asn Arg Asn Arg Gln
            580                 585                 590 tat taa                                                              1782
Tyr

<210> SEQ ID NO 13
<211> LENGTH: 593
<212> TYPE: PRT
<213> ORGANISM: Artificial Sequence
<220> FEATURE:
<223> OTHER INFORMATION: Synthetic Construct

<400> SEQUENCE: 13
```

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala
            20                  25                  30

Ala His Ser Ala Phe Ala His His His His His His Gly Ser Asp
        35                  40                  45

Gln Ile Cys Ile Gly Tyr His Ala Asn Asn Ser Thr Glu Gln Val Asp
    50                  55                  60

Thr Ile Met Glu Lys Asn Val Thr Val Thr His Ala Gln Asp Ile Leu
65                  70                  75                  80

Glu Lys Thr His Asn Gly Lys Leu Cys Asp Leu Asp Gly Val Lys Pro
                85                  90                  95

Leu Ile Leu Arg Asp Cys Ser Val Ala Gly Trp Leu Leu Gly Asn Pro
                100                 105                 110

Met Cys Asp Glu Phe Ile Asn Val Pro Glu Trp Ser Tyr Ile Val Glu
        115                 120                 125

Lys Ala Asn Pro Thr Asn Asp Leu Cys Tyr Pro Gly Ser Phe Asn Asp
    130                 135                 140

Tyr Glu Glu Leu Lys His Leu Leu Ser Arg Ile Asn His Phe Glu Lys
145                 150                 155                 160

Ile Gln Ile Ile Pro Lys Ser Ser Trp Ser Asp His Glu Ala Ser Ser
                165                 170                 175

Gly Val Ser Ser Ala Cys Pro Tyr Leu Gly Ser Pro Ser Phe Phe Arg
                180                 185                 190

Asn Val Val Trp Leu Ile Lys Lys Asn Ser Thr Tyr Pro Thr Ile Lys
        195                 200                 205

Lys Ser Tyr Asn Asn Thr Asn Gln Glu Asp Leu Leu Val Leu Trp Gly
210                 215                 220

Ile His His Pro Asn Asp Ala Ala Glu Gln Thr Arg Leu Tyr Gln Asn
225                 230                 235                 240

Pro Thr Thr Tyr Ile Ser Ile Gly Thr Ser Thr Leu Asn Gln Arg Leu
                245                 250                 255

Val Pro Lys Ile Ala Thr Arg Ser Lys Val Asn Gly Gln Ser Gly Arg
        260                 265                 270

Met Glu Phe Phe Trp Thr Ile Leu Lys Pro Asn Asp Ala Ile Asn Phe
        275                 280                 285

Glu Ser Asn Gly Asn Phe Ile Ala Pro Glu Tyr Ala Tyr Lys Ile Val
    290                 295                 300

Lys Lys Gly Asp Ser Ala Ile Met Lys Ser Glu Leu Glu Tyr Gly Asn
305                 310                 315                 320

Cys Asn Thr Lys Cys Gln Thr Pro Met Gly Ala Ile Asn Ser Ser Met
                325                 330                 335

Pro Phe His Asn Ile His Pro Leu Thr Ile Gly Glu Cys Pro Lys Tyr
                340                 345                 350

Val Lys Ser Asn Arg Leu Val Leu Ala Thr Gly Leu Arg Asn Ser Pro
        355                 360                 365

Gln Arg Glu Ser Arg Arg Lys Arg Gly Leu Phe Gly Ala Ile Ala
    370                 375                 380

Gly Phe Ile Glu Gly Gly Trp Gln Gly Met Val Asp Gly Trp Tyr Gly
385                 390                 395                 400

Tyr His His Ser Asn Glu Gln Gly Ser Gly Tyr Ala Ala Asp Lys Glu
            405                 410                 415

Ser Thr Gln Lys Ala Ile Asp Gly Val Thr Asn Lys Val Asn Ser Ile
        420                 425                 430
```

```
Ile Asp Lys Met Asn Thr Gln Phe Glu Ala Val Gly Arg Glu Phe Asn
            435                 440                 445

Asn Leu Glu Arg Arg Ile Glu Asn Leu Asn Lys Lys Met Glu Asp Gly
        450                 455                 460

Phe Leu Asp Val Trp Thr Tyr Asn Ala Glu Leu Leu Val Leu Met Glu
465                 470                 475                 480

Asn Glu Arg Thr Leu Asp Phe His Asp Ser Asn Val Lys Asn Leu Tyr
                485                 490                 495

Asp Lys Val Arg Leu Gln Leu Arg Asp Asn Ala Lys Glu Leu Gly Asn
            500                 505                 510

Gly Cys Phe Glu Phe Tyr His Lys Cys Asp Asn Glu Cys Met Glu Ser
        515                 520                 525

Ile Arg Asn Gly Thr Tyr Asn Tyr Pro Gln Tyr Ser Glu Glu Ala Arg
    530                 535                 540

Leu Lys Arg Glu Glu Ile Ser Gly Val Lys Leu Glu Ser Ile Gly Thr
545                 550                 555                 560

Tyr Gln Ile Leu Ser Ile Tyr Ser Thr Val Ala Ser Ser Leu Ala Leu
                565                 570                 575

Ala Ile Met Met Ala Gly Leu Ser Leu Trp Arg Asn Arg Asn Arg Gln
            580                 585                 590

Tyr
```

<210> SEQ ID NO 14
<211> LENGTH: 1776
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1776)
<220> FEATURE:
<221> NAME/KEY: misc_feature
<222> LOCATION: (1)..(114)
<223> OTHER INFORMATION: gp64 signal peptide
<220> FEATURE:
<221> NAME/KEY: misc_feature
<222> LOCATION: (118)..(141)
<223> OTHER INFORMATION: Flag tag
<220> FEATURE:
<221> NAME/KEY: misc_feature
<222> LOCATION: (142)..(147)
<223> OTHER INFORMATION: XhoI restriction site
<220> FEATURE:
<221> NAME/KEY: misc_feature
<222> LOCATION: (148)..(1752)
<223> OTHER INFORMATION: HA ectodomain and transmembrane domain
<220> FEATURE:
<221> NAME/KEY: misc_feature
<222> LOCATION: (1753)..(1776)
<223> OTHER INFORMATION: gp64 cytoplasmic tail domain

<400> SEQUENCE: 14

```
atg cta ctg gta aat cag tca cac caa ggc ttc aat aag gaa cac aca      48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg      96
Ser Lys Met Val Ser Ala Ile Val Leu Tyr Val Leu Leu Ala Ala Ala
            20                  25                  30 gcg cat tct gcc ttt gcg gtc gac tac aaa gac gat gac gac aag ctc     144
Ala His Ser Ala Phe Ala Val Asp Tyr Lys Asp Asp Asp Asp Lys Leu
        35                  40                  45 gag gat cag att tgc att ggt tac cat gca aac aac tcg aca gag cag     192
Glu Asp Gln Ile Cys Ile Gly Tyr His Ala Asn Asn Ser Thr Glu Gln
```

```
              50                  55                  60
gtt gac aca ata atg gaa aag aac gtc act gtt aca cac gcg caa gac       240
Val Asp Thr Ile Met Glu Lys Asn Val Thr Val Thr His Ala Gln Asp
 65              70                  75                  80 ata ctg gaa aag aca cac aac ggg aaa ctc tgc gat cta gat gga gtg       288
Ile Leu Glu Lys Thr His Asn Gly Lys Leu Cys Asp Leu Asp Gly Val
                 85                  90                  95 aag cct cta att tta aga gat tgt agt gta gct gga tgg ctc ctc ggg       336
Lys Pro Leu Ile Leu Arg Asp Cys Ser Val Ala Gly Trp Leu Leu Gly
            100                 105                 110 aac cca atg tgt gac gaa ttc ctc aat gtg ccg gaa tgg tct tac ata       384
Asn Pro Met Cys Asp Glu Phe Leu Asn Val Pro Glu Trp Ser Tyr Ile
        115                 120                 125 gtg gag aag atc aat cca gcc aat gac ctc tgt tac cca ggg aat ttc       432
Val Glu Lys Ile Asn Pro Ala Asn Asp Leu Cys Tyr Pro Gly Asn Phe
    130                 135                 140 aac gac tat gaa gaa ctg aaa cac cta ttg agc aga ata aac cat ttt       480
Asn Asp Tyr Glu Glu Leu Lys His Leu Leu Ser Arg Ile Asn His Phe
145                 150                 155                 160 gag aaa att cag atc atc ccc aaa agt tct tgg tca gat cat gaa gcc       528
Glu Lys Ile Gln Ile Ile Pro Lys Ser Ser Trp Ser Asp His Glu Ala
                165                 170                 175 tca tca ggg gtg agc tca gca tgt cca tac cag gga agg tcc tcc ttt       576
Ser Ser Gly Val Ser Ser Ala Cys Pro Tyr Gln Gly Arg Ser Ser Phe
            180                 185                 190 ttt aga aat gtg gta tgg ctt atc aaa aag gac aat gca tac cca aca       624
Phe Arg Asn Val Val Trp Leu Ile Lys Lys Asp Asn Ala Tyr Pro Thr
        195                 200                 205 ata aag aga agt tac aat aat acc aac caa gaa gat ctt ttg gta ctg       672
Ile Lys Arg Ser Tyr Asn Asn Thr Asn Gln Glu Asp Leu Leu Val Leu
    210                 215                 220 tgg ggg att cac cat cca aat gat gcg gca gag cag aca agg ctc tat       720
Trp Gly Ile His His Pro Asn Asp Ala Ala Glu Gln Thr Arg Leu Tyr
225                 230                 235                 240 caa aac cca acc acc tat att tcc gtt ggg aca tca aca cta aac cag       768
Gln Asn Pro Thr Thr Tyr Ile Ser Val Gly Thr Ser Thr Leu Asn Gln
                245                 250                 255 aga ctg gta cca aaa ata gct act aga tcc aag gta aac ggg caa agt       816
Arg Leu Val Pro Lys Ile Ala Thr Arg Ser Lys Val Asn Gly Gln Ser
            260                 265                 270 gga agg atg gag ttc ttt tgg aca att tta aaa ccg aat gat gca ata       864
Gly Arg Met Glu Phe Phe Trp Thr Ile Leu Lys Pro Asn Asp Ala Ile
        275                 280                 285 aac ttt gag agt aat gga aat ttc att gct cca gaa aat gca tac aaa       912
Asn Phe Glu Ser Asn Gly Asn Phe Ile Ala Pro Glu Asn Ala Tyr Lys
    290                 295                 300 att gtc aag aaa ggg gac tca aca att atg aaa agt gaa ttg gaa tat       960
Ile Val Lys Lys Gly Asp Ser Thr Ile Met Lys Ser Glu Leu Glu Tyr
305                 310                 315                 320 ggt aac tgc aac acc aag tgt caa act cca ata ggg gcg ata aac tct      1008
Gly Asn Cys Asn Thr Lys Cys Gln Thr Pro Ile Gly Ala Ile Asn Ser
                325                 330                 335 agt atg cca ttc cac aac atc cac cct ctc acc atc ggg gaa tgc ccc      1056
Ser Met Pro Phe His Asn Ile His Pro Leu Thr Ile Gly Glu Cys Pro
            340                 345                 350 aaa tat gtg aaa tca aac aga tta gtc ctt gcg act ggg ctc aga aat      1104
Lys Tyr Val Lys Ser Asn Arg Leu Val Leu Ala Thr Gly Leu Arg Asn
        355                 360                 365 agc cct caa att gaa act aga gga tta ttt gga gct ata gca ggt ttt      1152
Ser Pro Gln Ile Glu Thr Arg Gly Leu Phe Gly Ala Ile Ala Gly Phe
```

|  |  |  |  |  |  |  |  |  |  |  |  |  |  |  |  |
|---|---|---|---|---|---|---|---|---|---|---|---|---|---|---|---|
| | | | 370 | | | | 375 | | | | 380 | | | | |
| ata | gag | gga | gga | tgg | cag | gga | atg | gta | gat | ggt | tgg | tat | ggg | tac | cac | 1200
| Ile | Glu | Gly | Gly | Trp | Gln | Gly | Met | Val | Asp | Gly | Trp | Tyr | Gly | Tyr | His |
| 385 | | | | 390 | | | | 395 | | | | 400 | | | |
| cat | agc | aac | gag | cag | ggg | agt | ggg | tac | gct | gca | gac | aaa | gaa | tcc | act | 1248
| His | Ser | Asn | Glu | Gln | Gly | Ser | Gly | Tyr | Ala | Ala | Asp | Lys | Glu | Ser | Thr |
| | | | | 405 | | | | 410 | | | | 415 | | | |
| caa | aag | gca | ata | gat | gga | gtc | acc | aat | aag | gtc | aac | tcg | atc | att | gac | 1296
| Gln | Lys | Ala | Ile | Asp | Gly | Val | Thr | Asn | Lys | Val | Asn | Ser | Ile | Ile | Asp |
| | | | 420 | | | | 425 | | | | 430 | | | | |
| aaa | atg | aac | act | cag | ttt | gag | gct | gtt | gga | agg | gaa | ttt | aat | aac | tta | 1344
| Lys | Met | Asn | Thr | Gln | Phe | Glu | Ala | Val | Gly | Arg | Glu | Phe | Asn | Asn | Leu |
| | | | | 435 | | | | 440 | | | | 445 | | | |
| gaa | agg | aga | ata | gaa | aat | tta | aac | aag | aag | atg | gaa | gac | gga | ttc | cta | 1392
| Glu | Arg | Arg | Ile | Glu | Asn | Leu | Asn | Lys | Lys | Met | Glu | Asp | Gly | Phe | Leu |
| | 450 | | | | 455 | | | | 460 | | | | | | |
| gat | gtc | tgg | act | tat | aat | gct | gaa | ctt | ctg | gtt | ctc | atg | gaa | aat | gag | 1440
| Asp | Val | Trp | Thr | Tyr | Asn | Ala | Glu | Leu | Leu | Val | Leu | Met | Glu | Asn | Glu |
| 465 | | | | 470 | | | | 475 | | | | 480 | | | |
| aga | act | cta | gac | ttt | cat | gac | tca | aat | gtc | aag | aac | ctt | tac | gac | aag | 1488
| Arg | Thr | Leu | Asp | Phe | His | Asp | Ser | Asn | Val | Lys | Asn | Leu | Tyr | Asp | Lys |
| | | | | 485 | | | | 490 | | | | 495 | | | |
| gtc | cga | cta | cag | ctt | agg | gat | aat | gca | aag | gag | ctt | ggt | aac | ggt | tgt | 1536
| Val | Arg | Leu | Gln | Leu | Arg | Asp | Asn | Ala | Lys | Glu | Leu | Gly | Asn | Gly | Cys |
| | | | 500 | | | | 505 | | | | 510 | | | | |
| ttc | gag | ttc | tat | cat | aga | tgt | gat | aat | gaa | tgt | atg | gaa | agt | gta | aga | 1584
| Phe | Glu | Phe | Tyr | His | Arg | Cys | Asp | Asn | Glu | Cys | Met | Glu | Ser | Val | Arg |
| | | 515 | | | | 520 | | | | 525 | | | | | |
| aac | gga | acg | tat | gac | tac | ccg | cag | tat | tca | gaa | gaa | gca | aga | tta | aaa | 1632
| Asn | Gly | Thr | Tyr | Asp | Tyr | Pro | Gln | Tyr | Ser | Glu | Glu | Ala | Arg | Leu | Lys |
| | 530 | | | | 535 | | | | 540 | | | | | | |
| aga | gag | gaa | ata | agt | gga | gta | aaa | ttg | gaa | tca | ata | gga | act | tac | caa | 1680
| Arg | Glu | Glu | Ile | Ser | Gly | Val | Lys | Leu | Glu | Ser | Ile | Gly | Thr | Tyr | Gln |
| 545 | | | | 550 | | | | 555 | | | | 560 | | | |
| ata | ctg | tca | att | tat | tca | aca | gtg | gcg | agc | tcc | cta | gca | ctg | gca | atc | 1728
| Ile | Leu | Ser | Ile | Tyr | Ser | Thr | Val | Ala | Ser | Ser | Leu | Ala | Leu | Ala | Ile |
| | | | | 565 | | | | 570 | | | | 575 | | | |
| atg | gtg | gct | ggt | cta | tct | tta | tgg | aga | aac | cgt | aat | aga | caa | tat | taa | 1776
| Met | Val | Ala | Gly | Leu | Ser | Leu | Trp | Arg | Asn | Arg | Asn | Arg | Gln | Tyr | |
| | 580 | | | | 585 | | | | 590 | | | | | | |

<210> SEQ ID NO 15
<211> LENGTH: 591
<212> TYPE: PRT
<213> ORGANISM: Artificial Sequence
<220> FEATURE:
<223> OTHER INFORMATION: Synthetic Construct

<400> SEQUENCE: 15

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Val Asp Tyr Lys Asp Asp Asp Lys Leu
        35                  40                  45

Glu Asp Gln Ile Cys Ile Gly Tyr His Ala Asn Asn Ser Thr Glu Gln
50                  55                  60

Val Asp Thr Ile Met Glu Lys Asn Val Thr Val Thr His Ala Gln Asp
65                  70                  75                  80

Ile Leu Glu Lys Thr His Asn Gly Lys Leu Cys Asp Leu Asp Gly Val

-continued

```
                    85                  90                  95
Lys Pro Leu Ile Leu Arg Asp Cys Ser Val Ala Gly Trp Leu Leu Gly
                100                 105                 110

Asn Pro Met Cys Asp Glu Phe Leu Asn Val Pro Glu Trp Ser Tyr Ile
            115                 120                 125

Val Glu Lys Ile Asn Pro Ala Asn Asp Leu Cys Tyr Pro Gly Asn Phe
        130                 135                 140

Asn Asp Tyr Glu Glu Leu Lys His Leu Leu Ser Arg Ile Asn His Phe
145                 150                 155                 160

Glu Lys Ile Gln Ile Ile Pro Lys Ser Ser Trp Ser Asp His Glu Ala
                165                 170                 175

Ser Ser Gly Val Ser Ser Ala Cys Pro Tyr Gln Gly Arg Ser Ser Phe
            180                 185                 190

Phe Arg Asn Val Val Trp Leu Ile Lys Lys Asp Asn Ala Tyr Pro Thr
        195                 200                 205

Ile Lys Arg Ser Tyr Asn Asn Thr Asn Gln Glu Asp Leu Leu Val Leu
    210                 215                 220

Trp Gly Ile His His Pro Asn Asp Ala Ala Glu Gln Thr Arg Leu Tyr
225                 230                 235                 240

Gln Asn Pro Thr Thr Tyr Ile Ser Val Gly Thr Ser Thr Leu Asn Gln
                245                 250                 255

Arg Leu Val Pro Lys Ile Ala Thr Arg Ser Lys Val Asn Gly Gln Ser
            260                 265                 270

Gly Arg Met Glu Phe Phe Trp Thr Ile Leu Lys Pro Asn Asp Ala Ile
        275                 280                 285

Asn Phe Glu Ser Asn Gly Asn Phe Ile Ala Pro Glu Asn Ala Tyr Lys
    290                 295                 300

Ile Val Lys Lys Gly Asp Ser Thr Ile Met Lys Ser Glu Leu Glu Tyr
305                 310                 315                 320

Gly Asn Cys Asn Thr Lys Cys Gln Thr Pro Ile Gly Ala Ile Asn Ser
                325                 330                 335

Ser Met Pro Phe His Asn Ile His Pro Leu Thr Ile Gly Glu Cys Pro
            340                 345                 350

Lys Tyr Val Lys Ser Asn Arg Leu Val Leu Ala Thr Gly Leu Arg Asn
        355                 360                 365

Ser Pro Gln Ile Glu Thr Arg Gly Leu Phe Gly Ala Ile Ala Gly Phe
    370                 375                 380

Ile Glu Gly Gly Trp Gln Gly Met Val Asp Gly Trp Tyr Gly Tyr His
385                 390                 395                 400

His Ser Asn Glu Gln Gly Ser Gly Tyr Ala Ala Asp Lys Glu Ser Thr
                405                 410                 415

Gln Lys Ala Ile Asp Gly Val Thr Asn Lys Val Asn Ser Ile Ile Asp
            420                 425                 430

Lys Met Asn Thr Gln Phe Glu Ala Val Gly Arg Glu Phe Asn Asn Leu
        435                 440                 445

Glu Arg Arg Ile Glu Asn Leu Asn Lys Lys Met Glu Asp Gly Phe Leu
    450                 455                 460

Asp Val Trp Thr Tyr Asn Ala Glu Leu Leu Val Leu Met Glu Asn Glu
465                 470                 475                 480

Arg Thr Leu Asp Phe His Asp Ser Asn Val Lys Asn Leu Tyr Asp Lys
                485                 490                 495

Val Arg Leu Gln Leu Arg Asp Asn Ala Lys Glu Leu Gly Asn Gly Cys
            500                 505                 510
```

```
Phe Glu Phe Tyr His Arg Cys Asp Asn Glu Cys Met Glu Ser Val Arg
            515                 520                 525

Asn Gly Thr Tyr Asp Tyr Pro Gln Tyr Ser Glu Glu Ala Arg Leu Lys
    530                 535                 540

Arg Glu Glu Ile Ser Gly Val Lys Leu Glu Ser Ile Gly Thr Tyr Gln
545                 550                 555                 560

Ile Leu Ser Ile Tyr Ser Thr Val Ala Ser Ser Leu Ala Leu Ala Ile
                565                 570                 575

Met Val Ala Gly Leu Ser Leu Trp Arg Asn Arg Asn Arg Gln Tyr
            580                 585                 590

<210> SEQ ID NO 16
<211> LENGTH: 1779
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1779)
<220> FEATURE:
<221> NAME/KEY: misc_feature
<222> LOCATION: (1)..(114)
<223> OTHER INFORMATION: gp64 signal peptide
<220> FEATURE:
<221> NAME/KEY: misc_feature
<222> LOCATION: (115)..(135)
<223> OTHER INFORMATION: His tag
<220> FEATURE:
<221> NAME/KEY: misc_feature
<222> LOCATION: (136)..(141)
<223> OTHER INFORMATION: BamHI restriction site
<220> FEATURE:
<221> NAME/KEY: misc_feature
<222> LOCATION: (142)..(1755)
<223> OTHER INFORMATION: HA ectodomain and transmembrane domain
<220> FEATURE:
<221> NAME/KEY: misc_feature
<222> LOCATION: (1756)..(1779)
<223> OTHER INFORMATION: gp64 cytoplasmic tail domain

<400> SEQUENCE: 16 atg cta ctg gta aat cag tca cac caa ggc ttc aat aag gaa cac aca      48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg      96
Ser Lys Met Val Ser Ala Ile Val Leu Tyr Val Leu Leu Ala Ala Ala
                20                  25                  30 gcg cat tct gcc ttt gcg cat cac cac cat cac cat cac gga tcc gat     144
Ala His Ser Ala Phe Ala His His His His His His Gly Ser Asp
            35                  40                  45 cag att tgc att ggt tac cat gca aac aac tcg aca gag cag gtt gac     192
Gln Ile Cys Ile Gly Tyr His Ala Asn Asn Ser Thr Glu Gln Val Asp
 50                  55                  60 aca ata atg gaa aag aac gtt act gtt aca cat gcc caa gac ata ctg     240
Thr Ile Met Glu Lys Asn Val Thr Val Thr His Ala Gln Asp Ile Leu
65                  70                  75                  80 gaa aag aca cac aac ggg aag ctc tgc gat cta gat gga gtg aag cct     288
Glu Lys Thr His Asn Gly Lys Leu Cys Asp Leu Asp Gly Val Lys Pro
                85                  90                  95 ctg att tta aga gat tgt agt gta gct gga tgg ctc ctc gga aac cca     336
Leu Ile Leu Arg Asp Cys Ser Val Ala Gly Trp Leu Leu Gly Asn Pro
            100                 105                 110 atg tgt gac gaa ttc atc aat gtg ccg gaa tgg tct tac ata gtg gag     384
Met Cys Asp Glu Phe Ile Asn Val Pro Glu Trp Ser Tyr Ile Val Glu
            115                 120                 125
```

| | | |
|---|---|---|
| aag gcc aac cca gcc aat gac ctc tgt tac cca ggg aat ttc aac gac<br>Lys Ala Asn Pro Ala Asn Asp Leu Cys Tyr Pro Gly Asn Phe Asn Asp<br>130                 135                 140 | | 432 |
| tat gaa gaa ctg aaa cac cta ttg agc aga ata aac cat ttt gag aaa<br>Tyr Glu Glu Leu Lys His Leu Leu Ser Arg Ile Asn His Phe Glu Lys<br>145                 150                 155                 160 | | 480 |
| att cag atc atc ccc aaa agt tct tgg tcc gat cat gaa gcc tca tca<br>Ile Gln Ile Ile Pro Lys Ser Ser Trp Ser Asp His Glu Ala Ser Ser<br>                165                 170                 175 | | 528 |
| ggg gtg agc tca gca tgt cca tac cag gga acg ccc tcc ttt ttc aga<br>Gly Val Ser Ser Ala Cys Pro Tyr Gln Gly Thr Pro Ser Phe Phe Arg<br>                    180                 185                 190 | | 576 |
| aat gta gta tgg ctt atc aaa aag aac aat aca tac cca aca ata aag<br>Asn Val Val Trp Leu Ile Lys Lys Asn Asn Thr Tyr Pro Thr Ile Lys<br>                195                 200                 205 | | 624 |
| aga agc tac aat aat acc aac cag gaa gat ctt ttg ata ctg tgg ggg<br>Arg Ser Tyr Asn Asn Thr Asn Gln Glu Asp Leu Leu Ile Leu Trp Gly<br>                210                 215                 220 | | 672 |
| att cat cat tct aat gat gcg gca gag cag aca aag ctc tat caa aac<br>Ile His His Ser Asn Asp Ala Ala Glu Gln Thr Lys Leu Tyr Gln Asn<br>225                 230                 235                 240 | | 720 |
| cca acc acc tat att tcc gtt ggg aca tca aca cta aac cag aga ttg<br>Pro Thr Thr Tyr Ile Ser Val Gly Thr Ser Thr Leu Asn Gln Arg Leu<br>                    245                 250                 255 | | 768 |
| gta cca aaa ata gct act aga tcc aaa gta aac ggg caa agt gga agg<br>Val Pro Lys Ile Ala Thr Arg Ser Lys Val Asn Gly Gln Ser Gly Arg<br>                260                 265                 270 | | 816 |
| atg gat ttc ttc tgg aca att tta aaa ccg aat gat gca atc aac ttc<br>Met Asp Phe Phe Trp Thr Ile Leu Lys Pro Asn Asp Ala Ile Asn Phe<br>                275                 280                 285 | | 864 |
| gag agt aat gga aat ttc att gct cca gaa tat gca tac aaa att gtc<br>Glu Ser Asn Gly Asn Phe Ile Ala Pro Glu Tyr Ala Tyr Lys Ile Val<br>                290                 295                 300 | | 912 |
| aag aaa ggg gac tca gca att gtt aaa agt gaa gtg gaa tat ggt aac<br>Lys Lys Gly Asp Ser Ala Ile Val Lys Ser Glu Val Glu Tyr Gly Asn<br>305                 310                 315                 320 | | 960 |
| tgc aac aca aag tgt caa act cca ata ggg gcg ata aac tct agt atg<br>Cys Asn Thr Lys Cys Gln Thr Pro Ile Gly Ala Ile Asn Ser Ser Met<br>                325                 330                 335 | | 1008 |
| cca ttc cac aac ata cac cct ctc acc atc ggg gaa tgc ccc aaa tat<br>Pro Phe His Asn Ile His Pro Leu Thr Ile Gly Glu Cys Pro Lys Tyr<br>                340                 345                 350 | | 1056 |
| gtg aaa tca aac aaa tta gtc ctt gcg act ggg ctc aga aat agt cct<br>Val Lys Ser Asn Lys Leu Val Leu Ala Thr Gly Leu Arg Asn Ser Pro<br>                355                 360                 365 | | 1104 |
| cta aga gaa aga aga aga aaa aga gga cta ttt gga gct ata gca ggg<br>Leu Arg Glu Arg Arg Arg Lys Arg Gly Leu Phe Gly Ala Ile Ala Gly<br>                370                 375                 380 | | 1152 |
| ttt ata gag gga gga tgg cag gga atg gta gat ggt tgg tat ggg tac<br>Phe Ile Glu Gly Gly Trp Gln Gly Met Val Asp Gly Trp Tyr Gly Tyr<br>385                 390                 395                 400 | | 1200 |
| cac cat agc aat gag cag ggg agt ggg tac gct gca gac aaa gaa tcc<br>His His Ser Asn Glu Gln Gly Ser Gly Tyr Ala Ala Asp Lys Glu Ser<br>                405                 410                 415 | | 1248 |
| act caa aag gca ata gat gga gtc acc aat aag gtc aac tcg atc att<br>Thr Gln Lys Ala Ile Asp Gly Val Thr Asn Lys Val Asn Ser Ile Ile<br>                420                 425                 430 | | 1296 |
| gac aaa atg aac act cag ttt gag gcc gtt gga agg gaa ttt aat aac<br>Asp Lys Met Asn Thr Gln Phe Glu Ala Val Gly Arg Glu Phe Asn Asn<br>                435                 440                 445 | | 1344 |

| | | | | | | | | | | | | | | | | |
|---|---|---|---|---|---|---|---|---|---|---|---|---|---|---|---|---|
| tta | gaa | agg | aga | ata | gag | aat | tta | aac | aag | aaa | atg | gaa | gac | gga | ttc | 1392 |
| Leu | Glu | Arg | Arg | Ile | Glu | Asn | Leu | Asn | Lys | Lys | Met | Glu | Asp | Gly | Phe | |
| | 450 | | | | | 455 | | | | | 460 | | | | | |
| cta | gat | gtc | tgg | act | tat | aat | gct | gaa | ctt | ctg | gtt | ctc | atg | gaa | aat | 1440 |
| Leu | Asp | Val | Trp | Thr | Tyr | Asn | Ala | Glu | Leu | Leu | Val | Leu | Met | Glu | Asn | |
| 465 | | | | | 470 | | | | | 475 | | | | | 480 | |
| gag | aga | act | cta | gac | ttc | cat | gat | tca | aat | gtc | aag | aac | ctt | tac | gac | 1488 |
| Glu | Arg | Thr | Leu | Asp | Phe | His | Asp | Ser | Asn | Val | Lys | Asn | Leu | Tyr | Asp | |
| | | | | 485 | | | | | 490 | | | | | 495 | | |
| aag | gtc | cga | cta | cag | ctt | agg | gat | aat | gca | aag | gag | ctg | ggt | aac | ggt | 1536 |
| Lys | Val | Arg | Leu | Gln | Leu | Arg | Asp | Asn | Ala | Lys | Glu | Leu | Gly | Asn | Gly | |
| | | 500 | | | | | 505 | | | | | 510 | | | | |
| tgt | ttc | gag | ttc | tat | cac | aaa | tgt | gat | aat | gaa | tgt | atg | gaa | agt | gta | 1584 |
| Cys | Phe | Glu | Phe | Tyr | His | Lys | Cys | Asp | Asn | Glu | Cys | Met | Glu | Ser | Val | |
| 515 | | | | | 520 | | | | | 525 | | | | | | |
| aga | aac | gga | acg | tat | gac | tac | ccg | cag | tat | tca | gaa | gaa | gca | aga | tta | 1632 |
| Arg | Asn | Gly | Thr | Tyr | Asp | Tyr | Pro | Gln | Tyr | Ser | Glu | Glu | Ala | Arg | Leu | |
| Asn | 530 | | | | | 535 | | | | | 540 | | | | | |
| aaa | aga | gag | gaa | ata | agt | gga | gta | aaa | ttg | gaa | tca | ata | gga | act | tac | 1680 |
| Lys | Arg | Glu | Glu | Ile | Ser | Gly | Val | Lys | Leu | Glu | Ser | Ile | Gly | Thr | Tyr | |
| 545 | | | | | 550 | | | | | 555 | | | | | 560 | |
| caa | ata | ctg | tca | att | tat | tca | aca | gtt | gcg | agt | tct | cta | gca | ctg | gca | 1728 |
| Gln | Ile | Leu | Ser | Ile | Tyr | Ser | Thr | Val | Ala | Ser | Ser | Leu | Ala | Leu | Ala | |
| | | | | 565 | | | | | 570 | | | | | 575 | | |
| atc | atg | gtg | gct | ggt | cta | tct | ttg | tgg | aga | aac | cgt | aat | aga | caa | tat | 1776 |
| Ile | Met | Val | Ala | Gly | Leu | Ser | Leu | Trp | Arg | Asn | Arg | Asn | Arg | Gln | Tyr | |
| | | | 580 | | | | | 585 | | | | | 590 | | | |
| taa | | | | | | | | | | | | | | | | 1779 |

<210> SEQ ID NO 17
<211> LENGTH: 592
<212> TYPE: PRT
<213> ORGANISM: Artificial Sequence
<220> FEATURE:
<223> OTHER INFORMATION: Synthetic Construct

<400> SEQUENCE: 17

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala His His His His His His Gly Ser Asp
        35                  40                  45

Gln Ile Cys Ile Gly Tyr His Ala Asn Asn Ser Thr Glu Gln Val Asp
    50                  55                  60

Thr Ile Met Glu Lys Asn Val Thr Val Thr His Ala Gln Asp Ile Leu
65                  70                  75                  80

Glu Lys Thr His Asn Gly Lys Leu Cys Asp Leu Asp Gly Val Lys Pro
                85                  90                  95

Leu Ile Leu Arg Asp Cys Ser Val Ala Gly Trp Leu Leu Gly Asn Pro
            100                 105                 110

Met Cys Asp Glu Phe Ile Asn Val Pro Glu Trp Ser Tyr Ile Val Glu
        115                 120                 125

Lys Ala Asn Pro Ala Asn Asp Leu Cys Tyr Pro Gly Asn Phe Asn Asp
    130                 135                 140

Tyr Glu Glu Leu Lys His Leu Leu Ser Arg Ile Asn His Phe Glu Lys
145                 150                 155                 160

Ile Gln Ile Ile Pro Lys Ser Ser Trp Ser Asp His Glu Ala Ser Ser
                165                 170                 175

-continued

```
Gly Val Ser Ser Ala Cys Pro Tyr Gln Gly Thr Pro Ser Phe Phe Arg
            180                 185                 190

Asn Val Val Trp Leu Ile Lys Lys Asn Asn Thr Tyr Pro Thr Ile Lys
            195                 200                 205

Arg Ser Tyr Asn Asn Thr Asn Gln Glu Asp Leu Leu Ile Leu Trp Gly
            210                 215                 220

Ile His His Ser Asn Asp Ala Ala Glu Gln Thr Lys Leu Tyr Gln Asn
225                 230                 235                 240

Pro Thr Thr Tyr Ile Ser Val Gly Thr Ser Thr Leu Asn Gln Arg Leu
                245                 250                 255

Val Pro Lys Ile Ala Thr Arg Ser Lys Val Asn Gly Gln Ser Gly Arg
            260                 265                 270

Met Asp Phe Phe Trp Thr Ile Leu Lys Pro Asn Asp Ala Ile Asn Phe
            275                 280                 285

Glu Ser Asn Gly Asn Phe Ile Ala Pro Glu Tyr Ala Tyr Lys Ile Val
            290                 295                 300

Lys Lys Gly Asp Ser Ala Ile Val Lys Ser Glu Val Glu Tyr Gly Asn
305                 310                 315                 320

Cys Asn Thr Lys Cys Gln Thr Pro Ile Gly Ala Ile Asn Ser Ser Met
                325                 330                 335

Pro Phe His Asn Ile His Pro Leu Thr Ile Gly Glu Cys Pro Lys Tyr
            340                 345                 350

Val Lys Ser Asn Lys Leu Val Leu Ala Thr Gly Leu Arg Asn Ser Pro
            355                 360                 365

Leu Arg Glu Arg Arg Lys Arg Gly Leu Phe Gly Ala Ile Ala Gly
            370                 375                 380

Phe Ile Glu Gly Gly Trp Gln Gly Met Val Asp Gly Trp Tyr Gly Tyr
385                 390                 395                 400

His His Ser Asn Glu Gln Gly Ser Gly Tyr Ala Ala Asp Lys Glu Ser
                405                 410                 415

Thr Gln Lys Ala Ile Asp Gly Val Thr Asn Lys Val Asn Ser Ile Ile
            420                 425                 430

Asp Lys Met Asn Thr Gln Phe Glu Ala Val Gly Arg Glu Phe Asn Asn
            435                 440                 445

Leu Glu Arg Arg Ile Glu Asn Leu Asn Lys Lys Met Glu Asp Gly Phe
            450                 455                 460

Leu Asp Val Trp Thr Tyr Asn Ala Glu Leu Leu Val Leu Met Glu Asn
465                 470                 475                 480

Glu Arg Thr Leu Asp Phe His Asp Ser Asn Val Lys Asn Leu Tyr Asp
                485                 490                 495

Lys Val Arg Leu Gln Leu Arg Asp Asn Ala Lys Glu Leu Gly Asn Gly
            500                 505                 510

Cys Phe Glu Phe Tyr His Lys Cys Asp Asn Glu Cys Met Glu Ser Val
            515                 520                 525

Arg Asn Gly Thr Tyr Asp Tyr Pro Gln Tyr Ser Glu Glu Ala Arg Leu
            530                 535                 540

Lys Arg Glu Glu Ile Ser Gly Val Lys Leu Glu Ser Ile Gly Thr Tyr
545                 550                 555                 560

Gln Ile Leu Ser Ile Tyr Ser Thr Val Ala Ser Ser Leu Ala Leu Ala
                565                 570                 575

Ile Met Val Ala Gly Leu Ser Leu Trp Arg Asn Arg Asn Arg Gln Tyr
            580                 585                 590
```

```
<210> SEQ ID NO 18
<211> LENGTH: 38
<212> TYPE: DNA
<213> ORGANISM: Artificial Sequence
<220> FEATURE:
<223> OTHER INFORMATION: Synthetic construct

<400> SEQUENCE: 18
ggatccgaat tcaggcctgt cgacgagctc gcggccgc                               38
```

TETRAVALENT INFLUENZA VACCINE AND USE THEREOF

CROSS REFERENCE TO RELATED APPLICATIONS

This application claims the benefit of U.S. Provisional Application No. 61/382,766, filed Sep. 14, 2010, which is herein incorporated by reference in its entirety.

ACKNOWLEDGMENT OF GOVERNMENT SUPPORT

This invention was made with government support under grant number U01AI077771, awarded by the National Institutes of Health. The government has certain rights in the invention.

FIELD

This disclosure concerns tetravalent influenza vaccines using baculovirus display, and methods of their use

BACKGROUND

Each year, seasonal influenza causes over 300,000 hospitalizations and 36,000 deaths in the US alone (Simonsen et al., *Lancet Infect Dis* 7:658-66, 2007). The emergence of the novel H1N1 influenza virus in 2009 demonstrated how quickly a new influenza pandemic can sweep across the world. The spread of highly pathogenic H5N1 viruses in birds and coincident infections in humans have raised the concerns that H5N1 viruses may cause a new pandemic in humans. Vaccination is an effective method to prevent influenza infection. There are two influenza vaccine approaches licensed in the United States; the inactivated, split vaccine and the live-attenuated virus vaccine. Inactivated vaccines can efficiently induce humoral immune responses but generally only poor cellular immune responses.

Baculoviruses are a family of large rod-shaped enveloped viruses with a large circular double-stranded DNA genome (80-200 kb). Baculoviruses infect some insects, but not mammals (Blissard, *Cytotechnology* 20:73-93, 1996). *Autographa californica* multiple nucleopolyhedrovirus (AcMNPV) is the most well studied baculovirus and most extensively used for protein expression because the polyhedrin (PH) and p10 promoters are efficient promoters (McMichael et al., *N Engl J Med* 309:13-17, 1983). Compared to other protein expression approaches, the baculovirus expression vector system (BEVS) produces abundant protein yields with appropriate eukaryotic glycosylation and other modifications. This system has also been used for virus-like particle (VLP) production for vaccines against HIV, HPV and influenza (Gheysen et al., *Cell* 59:103-112, 1989; Kirnbauer et al., *J Virol* 67:6929-6936, 1993; Latham et al., *J Virol* 75:6154-6165, 2001). However, the baculovirus (BV)-derived VLPs are always accompanied with BV contamination. Therefore, separating VLPs from contaminating BV is an obstacle that needs to be overcome.

Due to its low cytotoxicity and absence of pre-existing antibodies (Kost et al., *Nat Biotechnol* 23:567-575, 2005; Strauss et al., *Mol Ther* 15:193-202, 2007), AcMNPV has emerged as a potent vaccine vector (Fan et al., *J Virol Methods* 150:21-26, 2008; Feng et al., *DNA Cell Biol* 25:668-673, 2006; Lin et al., *Vaccine* 26:6361-6367, 2008; Prabakaran et al., *Virology* 380:412-420, 2008; Yoshida et al., *Infect Immun* 77:1782-1789, 2009). Foreign immunogens or peptides can be displayed on the envelope of AcMNPV by fusion with the baculovirus major envelope protein gp64 (Boublik et al., *Biotechnology* (*NY*) 13:1079-1084, 1995; Oker-Blom et al., *Brief Funct Genomic Proteomic* 2:244-253, 2003).

SUMMARY

Disclosed herein is the finding that baculovirus display of multiple influenza virus hemagglutinin (HA) proteins elicits broadly reactive immune responses against influenza. Thus, provided herein are recombinant baculovirus vectors having multiple different HA nucleic acid sequences, for example, at least two, at least three or at least four such sequences. In a disclosed embodiment, the recombinant baculovirus vector has a first, second, third and fourth nucleic acid sequence, each encoding an influenza hemagglutinin (HA) fusion protein. The first, second, third and fourth nucleic acid sequences each encode an influenza HA with a different amino acid sequence. In some embodiments, each influenza HA fusion protein includes a baculovirus gp64 signal peptide; an HA ectodomain and transmembrane domain; and a baculovirus gp64 cytoplasmic tail domain. Also provided are insect cells containing the disclosed baculovirus vectors and recombinant baculoviruses produced by transfection of insect cells with the provided vectors.

Further provided are recombinant baculoviruses displaying multiple different influenza virus HA fusion proteins in the baculovirus envelope. For example, the recombinant baculovirus displays a first, second, third and fourth influenza virus HA fusion protein in the baculovirus envelope, wherein each HA fusion protein comprises a different HA amino acid sequence. In some embodiments, each HA fusion protein includes a baculovirus gp64 signal peptide; an HA ectodomain and transmembrane domain; and a baculovirus gp64 cytoplasmic tail domain. Also provided are compositions that include the recombinant baculoviruses disclosed herein.

Multivalent influenza virus vaccines comprising the recombinant baculoviruses disclosed herein are further provided. In addition, methods of immunizing a subject against influenza virus using the multivalent, for example tetravalent, influenza virus vaccines are provided. Also provided are methods of eliciting an immune response against influenza virus by administration of a recombinant baculovirus (or composition thereof) or multivalent influenza virus vaccine, as disclosed herein.

In particular examples of the compositions and methods disclosed herein, the HA polypeptides are from H5N1 influenza virus.

The foregoing and other objects and features of the disclosure will become more apparent from the following detailed description, which proceeds with reference to the accompanying figures.

BRIEF DESCRIPTION OF THE DRAWINGS

FIGS. 5A-5B: Virus titers in lungs at day 3 and 6 post-challenge. Mice (n=5/group) immunized intramuscularly with live/inactivated Bac-spHAct, wt BV, VLPs or mock vaccination. At week 3 after the final immunization, immunized mice were intranasally infected with a lethal dose of mouse-adapted PR8 virus (10 $LD_{50}$). Mice were sacrificed on day 3 (A) and day 6 (B) post-challenge and lungs were collected for plaque assay.

FIG. 7: Hemagglutination-inhibition (HAI) titers against H5N1 viruses. Mice (n=36/group) were immunized intramuscularly with Bac-HA2.2, Bac-4HA or wt BV. Week 5 serum HAI antibody responses were assessed against VN/04, IN/05, WS/05 and AH/05 viruses. Bars indicate geometric mean titer (GMT)+/−SEM.

FIG. 9: Virus titers in lungs at day 3 post-challenge. Mice (n=5/group) were immunized intramuscularly with Bac-HA2.2, Bac-4HA or wt BV. At week 3 after the second immunization, immunized mice were intranasally infected with a lethal dose of VN/04, IN/05 or WS/05. Mice were sacrificed on day 3 post-challenge and lungs were collected for plaque assay (*$p<0.05$, **$p<0.01$).

FIGS. 12A-12B: MHC class I pentamer staining. Lung lymphocytes were collected on day 6 (A) and day 9 (B) post-infection with IN/06. One sample from a non-vaccinated, non-infected mouse was used as a background control. Each sample was stained with HA- and NP-pentamer, CD3, CD8 and CD19 antibodies. Cells were acquired using a LSRII flow cytometer.

SEQUENCE LISTING

Figure 1:
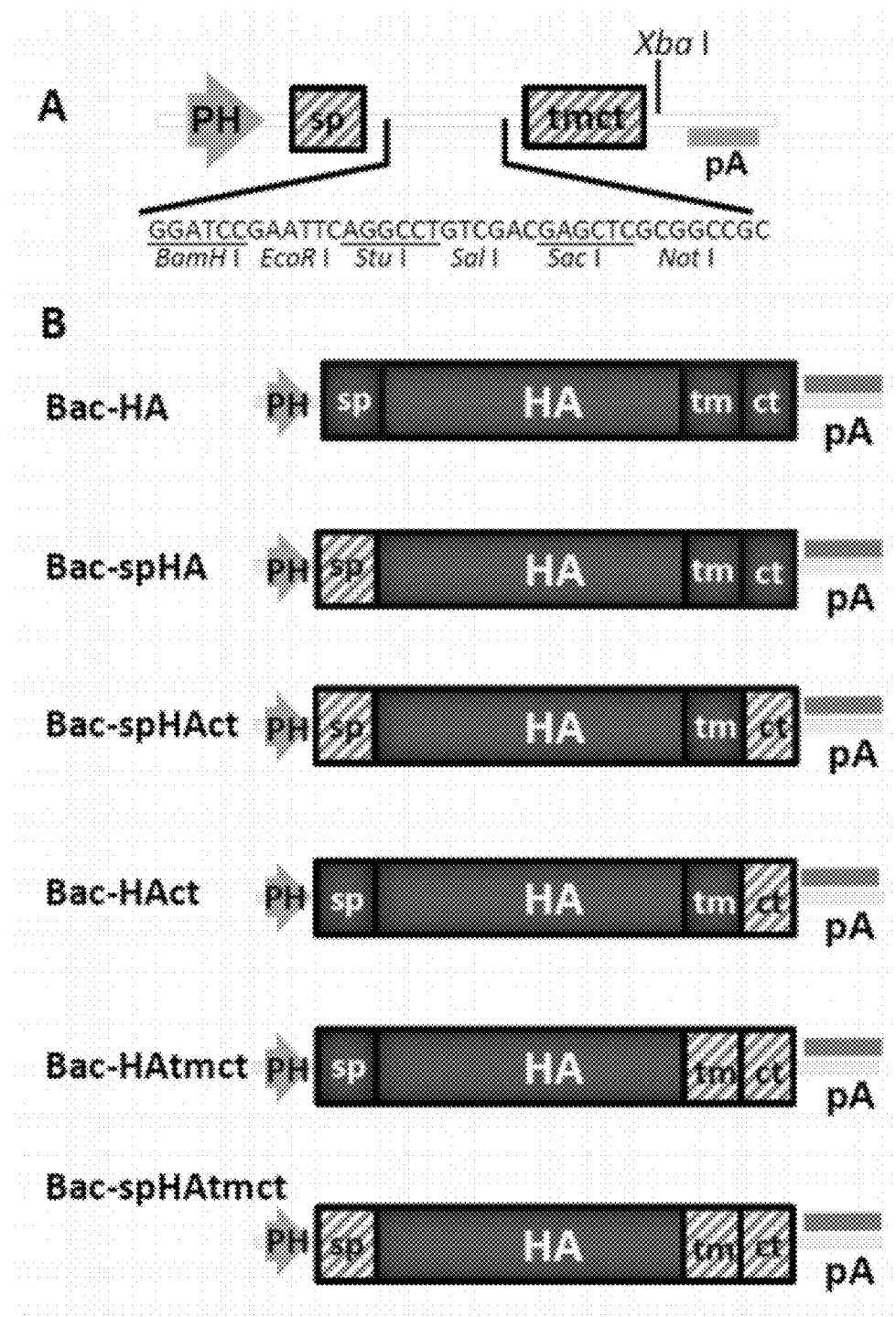
FIGS. 1A-1B: Schematic illustration of the HA-pseudotyped baculovirus. (A) Modified transfer vector with signal peptide (SP), transmembrane (TM), cytoplasmic tail (CT) domain sequences of gp64. The nucleotide sequence of the multiple-cloning site is set forth herein as SEQ ID NO: 18. (B) Schematic diagram of chimeric HA constructs. All components derived from HA are shown in dark gray while those from gp64 are shown in shadow.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 6, 2011, 58.4 KB, which is incorporated by reference herein. In the accompanying sequence listing:

SEQ ID NOs: 1-9 are the nucleotide sequences of primers used to construct recombinant baculoviruses.

SEQ ID NOs: 10 and 11 are the nucleotide and amino acid sequences, respectively, of the chimeric VN/04 HA.

SEQ ID NOs: 12 and 13 are the nucleotide and amino acid sequences, respectively, of the chimeric IN/05 HA.

SEQ ID NOs: 14 and 15 are the nucleotide and amino acid sequences, respectively, of the chimeric WS/05 HA.

SEQ ID NOs: 16 and 17 are the nucleotide and amino acid sequences, respectively, of the chimeric AH/05 HA.

SEQ ID NO: 18 is the nucleotide sequence of a multiple-cloning site in a baculovirus transfer vector.

DETAILED DESCRIPTION

I. Abbreviations

AcMNPV: *Autographa californica* multiple nucleopolyhedrovirus
BEVS: baculovirus expression vector system
BPL: β-propiolactone
BV: baculovirus
CT: cytoplasmic tail
CTL: cytotoxic T lymphocytes
DBV: displayed baculovirus
HA: hemagglutinin or hemagglutination assay
HAI: hemagglutination inhibition
hRBC: horse red blood cell
IFU: infectious unit
MOI: multiplicity of infection
PFU: plaque form unit
PH: polyhedrin
rBV: recombinant baculovirus
RDE: receptor destroying enzyme
SP: signal peptide
TM: transmembrane
tRBC: turkey red blood cell
VLP: virus-like particle II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (such as a vaccine) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza HA protein or chimeric HA protein.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. For example, the ability of an attenuated virus to cause disease in a subject can be reduced at least about 10%, at least about 25%, at least about 50%, at least about 75% or at least about 90% relative to wild-type virus.

Baculovirus: DNA viruses in the family Baculoviridae. Baculoviruses are a family of large rod-shaped enveloped viruses with a large circular double-stranded DNA genome (80-200 kb). Baculoviruses have a narrow host-range that is limited primarily to *Lepidopteran* species of insects (butterflies and moths), and baculoviruses do not infect mammals (Blissard, *Cytotechnology* 20:73-93, 1996). *Autographa californica* multiple nucleopolyhedrovirus (AcMNPV) is the most well studied baculovirus and most extensively used for protein expression because the polyhedrin (PH) and p10 promoters are efficient promoters (McMichael et al., *N Engl J Med* 309:13-17, 1983).

The baculovirus gp64 protein is a homotrimeric membrane glycoprotein. Generally, gp64 is 512 amino acids in length with four glycosylation sites at asparagine residues. This glycoprotein also has an N-terminal signal peptide, oligomerization and fusion domains, a hydrophobic transmembrane domain and a cytoplasmic tail domain. gp64 is essential for efficient budding of the virion and for the cell-to-cell transmission during the infection cycle as well as binding to the host cell surface. In some embodiments of the compositions and methods disclosed herein, the gp64 signal peptide is at least 95%, at least 96%, at least 97%, at least 98%, at least 99% or 100% identical to amino acid residues 1-38 of SEQ ID NO: 11. In particular examples, the gp64 signal peptide comprises, or consists of, residues 1-38 of SEQ ID NO: 11. In some embodiments herein, the gp64 cytoplasmic tail domain is at least 95%, at least 96%, at least 97%, at least 98%, at least 99% or 100% identical to amino acid residues 589-595 of SEQ ID NO: 11. In particular examples, the gp64 signal peptide comprises, or consists of, residues 589-595 of SEQ ID NO: 11.

The polyhedrin gene is present as a single copy in the baculovirus genome. Because the polyhedrin gene is not essential for virus replication in cultured cells, it can be readily modified to express foreign genes. The foreign gene sequence can be inserted into the polyhedrin gene 3' to the polyhedrin promoter sequence such that it is under the transcriptional control of the polyhedrin promoter. Baculovirus expression vectors (including those comprising the polyhedrin promoter for heterologous gene expression) are well known in the art and are commercially available (such as from Life Technologies, Carlsbad, Calif.).

Chimeric: A molecule (such as a polypeptide or polynucleotide) composed of portions having different origins. As used herein, a "chimeric HA" is an influenza HA having a portion of its sequence derived from influenza HA and at least one additional portion from another protein, such as baculovirus gp64. In particular embodiments, the chimeric HA comprises the HA ectodomain and transmembrane domain and the baculovirus gp64 signal peptide and gp64 cytoplasmic tail domain. Such chimeric HA proteins are also referred to herein as "HA fusion proteins."

Clade: Refers to the different categorizations of the known influenza viruses, such as influenza A H5N1 viruses. Viruses in an H5N1 clade are genetically related, but do not share the exact viral genome. There are at least ten different clades of H5N1 subtypes designated in the art: clade 0 clade 1, clade 2, clade 3, clade 4, clade 5, clade 6, clade 7, clade 8 and clade 9 (Abdel-Ghafar et al., *N Engl J Med* 358:261-273, 2008). Clade 2 is further divided into subclades (including clade 2.1, clade 2.2, clade 2.3, clade 2.4 and clade 2.5).

Different: As used herein, influenza HA proteins having "different" amino acid sequences refers to HA proteins that differ by at least one amino acid residue, such as at least 1, at least 2, at least 3, at least 4, at least 5, at least 6, at least 7, at least 8, at least 9 or at least 10 amino acid residues. In some embodiments, the HA proteins having "different" amino acid sequences have sequences that are no more than 50%, no more than 60%, no more than 70%, no more than 80%, no more than 90%, no more than 95%, no more than 98% or no more than 99% identical. In particular examples, the "different" HA proteins are each from a different clade, sub-clade, subtype, or any combination thereof.

Display/Displaying: As used herein, baculovirus "display" of a protein (such as HA) refers to expression of the protein in the baculovirus envelope. The recombinant baculovirus vectors disclosed herein encode four different chimeric influenza HA proteins, and upon transfection of the baculovirus vector into a host cell, each chimeric HA is expressed and translocated to the cell membrane. The recombinant baculoviruses produced from the transfected host cells incorporate the chimeric HAs into the viral envelope, thus "displaying" the chimeric HAs on the surface of the baculovirus virion.

Fusion protein: A protein (such as an HA fusion protein) generated by expression of a nucleic acid sequence engineered from nucleic acid sequences encoding at least a portion of two different (heterologous) proteins. To create a fusion protein, the nucleic acid sequences are in the same reading frame and contain no internal stop codons. In particular embodiments, the HA fusion protein comprises the HA ectodomain and transmembrane domain and the baculovirus gp64 signal peptide and gp64 cytoplasmic tail domain. Such HA fusion proteins are also referred to herein as "chimeric HA proteins."

Hemagglutinin (HA): An influenza virus surface glycoprotein. HA mediates binding of the virus particle to a host cells and subsequent entry of the virus into the host cell. HA (along with NA) is one of the two major influenza virus antigenic determinants. The nucleotide and amino acid sequences of numerous influenza HA proteins are known in the art and are publically available, such as those deposited with GenBank. In some embodiments of the compositions and methods disclosed herein, the HA is an H1, H2, H3, H4, H5, H6, H7, H8, H9, H10, H11, H12, H13, H14, H15 or H16 HA. In some embodiments, the HA is from an H5N1 influenza virus isolate. In particular examples in which the HA is from an H5N1 virus, the HA can be from clade 0, clade 1, clade, 2.1, clade 2.2, clade 2.3, clade 2.4, clade 2.5, clade 4, clade 4, clade 5, clade 6, clade 7, clade 8 or clade 9. The recombinant baculoviruses disclosed herein display multiple HA proteins, each having a different amino acid sequence. Generally, the HA proteins are each from a different clade, sub-clade or subtype and thus have a different amino acid sequence (such as an amino acid sequence that is no more than 50%, no more than 60%, no more than 70%, no more than 80%, no more than 90%, no more than 95% or no more than 99% identical to the other displayed HA proteins).

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response (such as an influenza virus vaccine), such as the production of antibodies or a T-cell response in an animal, including compositions that are injected or absorbed into an animal. As used herein, as "immunogenic composition" is a composition comprising an immunogen (such as an HA polypeptide). An "immunogen" is also referred to as an "antigen."

Immunize: To render a subject protected from an infectious disease, such as by vaccination.

Influenza virus: A segmented negative-strand RNA virus that belongs to the Orthomyxoviridae family. There are three types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. H5N1 is also referred to as "avian influenza."

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

Linker: One or more amino acids that serve as a spacer between two polypeptides of a fusion protein.

Multivalent: In the context of the present disclosure, "multivalent" refers to a composition, such as a recombinant baculovirus or influenza vaccine, having multiple different antigenic determinants, such as multiple (e.g., two, three, four, five or six) different HA polypeptides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments, of the present disclosure, the promoter used for expression of the HA fusion proteins is the baculovirus polyhedrin promoter.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates. In one example, a subject is one who is infective with influenza, or is at risk for such infection.

Tetravalent influenza virus vaccine: An influenza vaccine having four different antigenic determinants, such as four different HA polypeptides. In some embodiments, the tetravalent influenza virus vaccine is a recombinant baculovirus displaying four different chimeric HA polypeptides.

Therapeutically effective amount: A quantity of a specified agent (such as a recombinant baculovirus displaying influenza HA polypeptides) sufficient to achieve a desired effect in a subject being treated with that agent. For example, this may be the amount of an influenza virus vaccine useful for eliciting an immune response in a subject and/or for preventing infection by influenza virus. Ideally, in the context of the present disclosure, a therapeutically effective amount of an influenza vaccine is an amount sufficient to increase resistance to, prevent, ameliorate, and/or treat infection caused by influenza virus in a subject without causing a substantial cytotoxic effect in the subject. The effective amount of an influenza vaccine useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes. In some embodiments of the present disclosure, the vector is a baculovirus vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Baculovirus (BV) replicating in insect cells can express a foreign gene product as part of its genome. The influenza hemagglutinin (HA) can be expressed from BV and displayed on the surface of baculovirus (HA-DBV). In the studies described herein, six recombinant baculoviruses were generated that express chimeric HAs with segments of the BV glycoprotein (gp64). It is disclosed herein that the signal peptide (SP) and cytoplasmic tail (CT) domains of gp64 enhance the display of HA from influenza virus on the BV surface, while the transmembrane (TM) domain of gp64 impairs HA display. Different doses of either live or β-propiolactone (BPL)-inactivated HA-DBV were administered to BALB/c mice. Live HA-DBV elicited higher hemagglutination-inhibition (HAI) titers than BPL-inactivated HA-DBV, and provided sterilizing protection. A second generation recombinant BV simultaneously displaying four HAs derived from four subclades of H5N1 influenza viruses was also constructed. This tetravalent H5N1 HA-DBV vaccine elicited HAI titers against all four homologous H5N1 viruses, significantly decreased viral lung titers of challenged mice, and provided 100% protection against lethal doses of homologous H5N1 viruses. Moreover, mice vaccinated with HA-DBV exhibited high levels of IFNγ-secreting and HA-specific CD8$^+$ T cells. Taken together, these results demonstrate that HA-DBV can stimulate strong humoral, as well as cellular immune responses, and is an effective vaccine for influenza.

VI. Overview of Several Embodiments

Disclosed herein is the finding that baculovirus display of multiple influenza virus hemagglutinin (HA) proteins elicits broadly reactive immune responses against influenza. For example, provided herein are recombinant baculovirus vectors having multiple different HA nucleic acid sequences, for example, at least two, at least three or at least four such sequences. In some embodiments, the recombinant baculovirus vectors comprise a first, second, third and fourth nucleic acid sequence, each encoding an influenza HA fusion protein. The first, second, third and fourth nucleic acid sequences each encode an influenza HA polypeptide (such as the HA ectodomain and transmembrane domain) with a different amino acid sequence. For example, the different amino acid sequences are from different clades, sub-clade, subtypes, or any combination thereof. In some cases, the HA proteins are no more than 50%, no more than 60%, no more than 70%, no more than 80%, no more than 85%, no more than 90%, no more than 95%, no more than 98% or no more than 99% identical to each of the other HA proteins. In some embodiments, each influenza HA fusion protein includes a baculovirus gp64 signal peptide; an HA ectodomain and transmembrane domain; and a baculovirus gp64 cytoplasmic tail domain.

In some embodiments, multiple nucleic acid sequences, for example, the first, second, third and fourth nucleic acid sequences of the recombinant baculovirus vector are each operably linked to a promoter, such as the baculovirus polyhedrin promoter.

The recombinant baculovirus vectors of the present disclosure can be used to express (and display in the baculovirus envelope) any combination of influenza HA polypeptides from any type of influenza virus (including influenza A, influenza B or influenza C), or any subtype or clade of influenza virus. In some embodiments, the influenza virus is an influenza A virus. In particular examples in which the influenza virus is an influenza A virus, one or more of the HA polypeptides is selected from the H1, H2, H3, H4, H5, H6, H7, H8, H9, H10, H11, H12, H13, H14, H15 and H16 subtype. In some examples, the HA is from an H5N1, H1N1, H1N2 or H3N2 influenza A virus.

For example, the present disclosure contemplates recombinant vectors encoding multiple (such as four) different HA proteins from the same subtype (e.g., four different H1 HA proteins, four different H2 HA proteins, four different H3 HA proteins, four different H4 HA proteins, four different H5 HA proteins, four different H6 HA proteins, four different H7 HA proteins, four different H8 HA proteins, four different H9 HA proteins, four different H10 HA proteins, four different H11

HA proteins, four different H12 HA proteins, four different H13 HA proteins, four different H14 HA proteins, four different H15 HA proteins, or four different H16 HA proteins).

The present disclosure further encompasses recombinant vectors encoding HA proteins from two or more influenza A subtypes. For example, the recombinant vector can encode one or more HA proteins from the H5 subtype and one or more HA proteins from the H1 subtype.

In some embodiments, the multiple, for example the first, second, third and fourth nucleic acid sequences each encode an HA from an H5N1 influenza virus. The H5N1 influenza virus can be selected from any clade or subclade of H5N1, such as clade 0, clade 1, clade, 2.1, clade 2.2, clade 2.3, clade 2.4, clade 2.5, clade 4, clade 4, clade 5, clade 6, clade 7, clade 8 or clade 9.

For example, the present disclosure contemplates any combination of four HA proteins selected from any one of clades 0, 1, 2.1, 2.2, 2.3, 2.4, 2.5, 3, 4, 5, 6, 7, 8 and 9. The combination can include only one HA protein from each clade, or can include two or more HA proteins from one clade and two or more HA proteins from a second clade. In some examples, the recombinant vectors encode HA proteins from three different or four different clades.

In some embodiments, the H5N1 influenza virus is a clade 1, clade 2.1, clade 2.2 or clade 2.3 H5N1 influenza virus. In some embodiments, at least one of the nucleic acid sequences of the recombinant baculovirus vector encodes an HA polypeptide selected from the group consisting of A/Vietnam/1203/2004 (VN/04); A/Indonesia/5/05 (IN/05); A/Whooper Swan/244/Mongolia/05 (WS/05); and A/Anhui/1/05 HA (AH/05). In some cases, the recombinant baculovirus vector encodes one influenza HA polypeptide from each of clade 1, clade 2.1, clade 2.2 and clade 2.3. In particular examples, the clade 1 H5N1 influenza virus is A/Vietnam/1203/2004 (VN/04); the clade 2.1 H5N1 influenza virus is A/Indonesia/5/05 (IN/05); the clade 2.2 H5N1 influenza virus is A/Whooper Swan/244/Mongolia/05 (WS/05); and/or the clade 2.3 H5N1 influenza virus is A/Anhui/1/05 HA (AH/05).

The nucleic acid sequences encoding HA proteins from numerous different influenza viruses, including influenza A viruses, such as H5N1 viruses, are publically available (such as those deposited with GenBank). Thus, one skilled in the art would be able to select any influenza virus HA polypeptide for use with the disclosed baculovirus vectors.

In some embodiments, the nucleic acid sequence encoding the gp64 signal peptide of the HA fusion protein is at least 80%, at least 85%, at least 90%, at least 95%, at least 96%, at least 97%, at least 98%, or at least 99% identical to nucleotides 1-114 of SEQ ID NO: 10; and/or the nucleic acid sequence encoding the gp64 cytoplasmic tail domain is at least 80%, at least 85%, at least 90%, at least 95%, at least 96%, at least 97%, at least 98%, or at least 99% identical to nucleotides 1765-1788 of SEQ ID NO: 10.

In some examples, the nucleic acid sequence encoding the gp64 signal peptide of the HA fusion protein comprises nucleotides 1-114 of SEQ ID NO: 10; and/or the nucleic acid sequence encoding the gp64 cytoplasmic tail domain comprises nucleotides 1765-1788 of SEQ ID NO: 10. In particular examples, the nucleic acid sequence encoding the gp64 signal peptide of the HA fusion protein consists of nucleotides 1-114 of SEQ ID NO: 10; and/or the nucleic acid sequence encoding the gp64 cytoplasmic tail domain consists of nucleotides 1765-1788 of SEQ ID NO: 10.

In some embodiments, the first, second, third and fourth nucleic acid sequences are at least 80%, at least 85%, at least 90%, at least 95%, at least 96%, at least 97%, at least 98%, or at least 99% identical to the nucleic acid sequences of SEQ ID NO: 10, SEQ ID NO: 12, SEQ ID NO: 14 and SEQ ID NO: 16. In some examples, the first, second, third and fourth nucleic acid sequences comprise the nucleic acid sequences of SEQ ID NO: 10, SEQ ID NO: 12, SEQ ID NO: 14 and SEQ ID NO: 16. In particular examples, the first, second, third and fourth nucleic acid sequences consist of the nucleic acid sequences of SEQ ID NO: 10, SEQ ID NO: 12, SEQ ID NO: 14 and SEQ ID NO: 16.

Also provided are insect cells containing (e.g., transfected with) the disclosed baculovirus vectors. In some embodiments, the insect cells are *Spodoptera frugiperda* cells, such as Sf9 cells. In other embodiments, the insect cells are cells from *Bombix mori, Galleria mellanoma, Trichplusia ni*, or *Lamanthria dispar*.

Further provided are recombinant baculoviruses produced by transfection of insect cells with the recombinant baculovirus vectors disclosed herein.

Also provided are recombinant baculoviruses displaying a first, second, third and fourth influenza virus HA fusion protein in the baculovirus envelope, wherein each HA fusion protein comprises a different HA amino acid sequence. In some embodiments, each HA fusion protein includes a baculovirus gp64 signal peptide; an HA ectodomain and transmembrane domain; and a baculovirus gp64 cytoplasmic tail domain.

The recombinant baculoviruses of the present disclosure can display any combination of influenza HA polypeptides from any type of influenza virus (including influenza A, influenza B or influenza C), or any subtype or clade of influenza virus. In some embodiments, the influenza virus is an influenza A virus. In particular examples in which the influenza virus is an influenza A virus, one or more of the HA polypeptides is selected from the H1, H2, H3, H4, H5, H6, H7, H8, H9, H10, H11, H12, H13, H14, H15 and H16 subtype. In some examples, the HA is from an H5N1, H1N1, H1N2 or H3N2 influenza A virus.

For example, the present disclosure contemplates recombinant baculoviruses displaying HA fusion proteins having amino acid sequence from four different HA proteins from the same subtype (e.g., four different H1 HA proteins, four different H2 HA proteins, four different H3 HA proteins, four different H4 HA proteins, four different H5 HA proteins, four different H6 HA proteins, four different H7 HA proteins, four different H8 HA proteins, four different H9 HA proteins, four different H10 HA proteins, four different H11 HA proteins, four different H12 HA proteins, four different H13 HA proteins, four different H14 HA proteins, four different H15 HA proteins, or four different H16 HA proteins).

The present disclosure further encompasses recombinant baculoviruses displaying HA polypeptides from two or more influenza A subtypes. For example, the recombinant baculovirus or can display one or more HA proteins from the H5 subtype and one or more HA proteins from the H1 subtype.

In some embodiments, the first, second, third and fourth HA fusion proteins displayed by the recombinant baculovirus each comprise HA amino acid sequence from an H5N1 influenza virus. The H5N1 influenza virus can be selected from, for example, clade 1, clade 2.1, clade 2.2 or clade 2.3 H5N1 influenza virus.

For example, the present disclosure contemplates recombinant baculoviruses displaying any combination of four HA polypeptides selected from any one of clades 0, 1, 2.1, 2.2, 2.3, 2.4, 2.5, 3, 4, 5, 6, 7, 8 and 9. The combination can include only one HA protein from each clade, or can include two or more HA proteins from one clade and two or more HA proteins from a second clade. In some examples, the recombinant baculovirus displays HA proteins from three different or four different clades.

In some embodiments, at least one of the HA polypeptides is selected from the group consisting of A/Vietnam/1203/2004 (VN/04); A/Indonesia/5/05 (IN/05); A/Whooper Swan/244/Mongolia/05 (WS/05); and A/Anhui/1/05 HA (AH/05). In some cases, the recombinant baculovirus displays one influenza HA polypeptide from each of clade 1, clade 2.1, clade 2.2 and clade 2.3. In particular examples, the clade 1 H5N1 influenza virus is A/Vietnam/1203/2004 (VN/04); the clade 2.1 H5N1 influenza virus is A/Indonesia/5/05 (IN/05); the clade 2.2 H5N1 influenza virus is A/Whooper Swan/244/Mongolia/05 (WS/05); and/or the clade 2.3 H5N1 influenza virus is A/Anhui/1/05 HA (AH/05).

In some embodiments, the amino acid sequence of the gp64 signal peptide is at least 80%, at least 85%, at least 90%, at least 95%, at least 96%, at least 97%, at least 98%, or at least 99% identical to amino acid residues 1-38 of SEQ ID NO: 11; and/or the amino acid sequence of the gp64 cytoplasmic tail domain is at least 80%, at least 85%, at least 90%, at least 95%, at least 96%, at least 97%, at least 98%, or at least 99% identical to amino acid residues 589-595 of SEQ ID NO: 11.

In some embodiments, the amino acid sequence of the gp64 signal peptide comprises amino acid residues 1-38 of SEQ ID NO: 11; and/or the amino acid sequence of the gp64 cytoplasmic tail domain comprises amino acid residues 589-595 of SEQ ID NO: 11. In some embodiments, the amino acid sequence of the gp64 signal peptide consists of amino acid residues 1-38 of SEQ ID NO: 11; and/or the amino acid sequence of the gp64 cytoplasmic tail domain consists of amino acid residues 589-595 of SEQ ID NO: 11.

In some embodiments, the amino acid sequence of the first, second, third and fourth influenza virus HA fusion proteins is at least 80%, at least 85%, at least 90%, at least 95%, at least 96%, at least 97%, at least 98%, or at least 99% identical to the amino acid sequences of SEQ ID NO: 11, SEQ ID NO: 13, SEQ ID NO: 15 and SEQ ID NO: 17. In some examples, the first, second, third and fourth influenza virus HA fusion proteins comprise the amino acid sequences of SEQ ID NO: 11, SEQ ID NO: 13, SEQ ID NO: 15 and SEQ ID NO: 17. In particular examples, the first, second, third and fourth influenza virus HA fusion proteins consist of the amino acid sequences of SEQ ID NO: 11, SEQ ID NO: 13, SEQ ID NO: 15 and SEQ ID NO: 17.

Also provided are compositions comprising the recombinant baculoviruses disclosed herein. In some embodiments, the compositions further comprise a pharmaceutically acceptable carrier, an adjuvant, or both.

Tetravalent influenza virus vaccines comprising the recombinant baculoviruses disclosed herein are further provided. In some embodiments, the tetravalent influenza virus vaccine further comprises a pharmaceutically acceptable carrier, an adjuvant, or both.

In addition, methods of immunizing a subject against influenza virus are provided. In some embodiments, the methods of immunization include administration of a therapeutically effective amount of a tetravalent influenza virus vaccine, a therapeutically effective amount of a recombinant baculovirus displaying HA fusion proteins as disclosed herein, or a therapeutically effective amount of a composition comprising the recombinant baculoviruses. In particular examples, the influenza virus is an H5N1 influenza virus.

Also provided are methods of eliciting an immune response against influenza virus by administration of a therapeutically effective amount of a recombinant baculovirus (or composition thereof) or tetravalent influenza virus vaccine, as disclosed herein. In particular examples, the influenza virus is an H5N1 influenza virus.

In some embodiments of the methods disclosed herein, administration is intramuscular administration, such as by intramuscular injection.

The immune response to immunization with a recombinant baculovirus can be measured according to any standard method, such as by measurement of HA-specific antibody titers (such as by ELISA), HAI titers, IFNγ (such as by ELISPOT) and/or influenza-specific T cells (such as by MHC class I pentamer staining). The extent of an immune response can also be evaluated by determining viral titers in infected subjects that have been vaccinated. In some embodiments, immunization with a recombinant baculovirus disclosed herein increases an immune response at least 2-fold, at least 3-fold, at least 4-fold, at least 5-fold, at least 6-fold, at least 7-fold, at least 8-fold, at least 9-fold or at least 10-fold compared to immunization with another influenza vaccine (such as a vaccine containing a single HA polypeptide or a BPL-inactivated recombinant baculovirus). In particular examples, the HAI titer is increased at least 3-fold, at least 4-fold, at least 5-fold, at least 6-fold, at least 7-fold or at least 8-fold relative to an inactivated Bac-4HA vaccine, or at least 3-fold compared to a vaccine containing a single influenza HA polypeptide (such as Bac-HA2.2). In some examples, IFN-g production is increased at least 1.5-fold or at least 2-fold compared with a vaccine containing a single influenza HA polypeptide (such as Bac-HA2.2).

V. Baculovirus Display

Baculoviruses are large rod-shaped enveloped viruses with a large circular double-stranded DNA genome (80-200 kb) in the family Baculoviridae. These viruses are known to have a narrow host-range that is limited primarily to *Lepidopteran* species of insects (butterflies and moths). *Autographa californica* multiple nucleopolyhedrovirus (AcMNPV) is the most well studied baculovirus and most extensively used for protein expression because the polyhedrin (PH) and p10 promoters are efficient promoters (McMichael et al., *N Engl J Med* 309:13-17, 1983). AcMNPV is well-characterized with regard to host range, molecular biology and genetics.

Many baculoviruses, including AcMNPV, form large protein crystalline occlusions within the nucleus of infected cells. A single polypeptide, referred to as a polyhedrin, accounts for approximately 95% of the protein mass of these occlusion bodies. The gene for polyhedrin is present as a single copy in the AcMNPV viral genome. Because the polyhedrin gene is not essential for virus replication in cultured cells, it can be readily modified to express foreign genes. The foreign gene sequence can be inserted into the AcMNPV gene just 3' to the polyhedrin promoter sequence such that it is under the transcriptional control of the polyhedrin promoter.

Recombinant baculoviruses that express foreign genes can be constructed by way of homologous recombination between baculovirus DNA and chimeric plasmids containing the gene sequence of interest. Recombinant viruses can be detected by virtue of their distinct plaque morphology and plaque-purified to homogeneity.

Baculoviruses are particularly well-suited for use as eukaryotic cloning and expression vectors. They are generally safe by virtue of their narrow host range which is restricted to arthropods. The U.S. Environmental Protection Agency (EPA), has approved the use of three baculovirus species for the control of insect pests.

AcMNPV wild type and recombinant viruses replicate in a variety of insect cells, including continuous cell lines derived from the fall armyworm, *Spodoptera frugiperda* (e.g., Sf9 cells). *S. frugiperda* cells have a population doubling time of 18 to 24 hours and can be propagated in monolayer or in free suspension cultures. *S. frugiperda* cells have not been reported to support the replication of any known mammalian viruses. Other insect cells that can be infected by baculovirus, such as those from the species *Bombix mori, Galleria mellanoma, Trichplusia ni*, or *Lamanthria dispar*, can also be used to generate recombinant baculoviruses.

Due to its low cytotoxicity and absence of pre-existing antibodies (Kost et al., *Nat Biotechnol* 23:567-575, 2005; Strauss et al., *Mol Ther* 15:193-202, 2007), AcMNPV has emerged as a potent vaccine vector (Fan et al., *J Virol Methods* 150:21-26, 2008; Feng et al., *DNA Cell Biol* 25:668-673, 2006; Lin et al., *Vaccine* 26:6361-6367, 2008; Prabakaran et al., *Virology* 380:412-420, 2008; Yoshida et al., *Infect Immun* 77:1782-1789, 2009). Foreign immunogens or peptides can be displayed on the envelope of AcMNPV by fusion with the baculovirus major envelope protein gp64 (Boublik et al., *Biotechnology (NY)* 13:1079-1084, 1995; Oker-Blom et al., *Brief Funct Genomic Proteomic* 2:244-253, 2003).

Based on the baculovirus display system, some efficient vaccines have been studied not only for viral diseases, such as classical swine fever virus (Xu et al., *Vaccine* 26:5455-60, 2008), influenza virus (Jin et al., *PLoS ONE* 3:e3933, 2008; Prabakaran et al., *J Virol* 84:3201-3209, 2010; Prabakaran et al., *Virology* 380:412-420, 2008; Yang et al., *Mol Ther* 15:989-996, 2007), avian reovirus (Lin et al., *Vaccine* 26:6361-6367, 2008), and bovine herpesvirus (Peralta et al., *Appl Microbiol Biotechnol* 75:407-414, 2007), but also for parasitic diseases, such as *Plasmodium berghei* (Boublik et al., *Biotechnology (NY)* 13:1079-1084, 1995; Yoshida et al., *Infect Immun* 77:1782-1789, 2009) and *Plasmodium falciparum* (Strauss et al., *Mol Ther* 15:193-202, 2007).

Most BV display strategies rely on gp64 protein, which is the major envelope protein of baculovirus. Both influenza HA and baculovirus gp64 are type I transmembrane glycoproteins comprised of an amino-terminal signal peptide domain, carboxy-proximal transmembrane domain and cytoplasmic tail domain. Both proteins mediate viral entry into host cells and efficient virion budding (Monsma and Blissard, *J Virol* 69:2583-2595, 1995; Oomens et al., *Virology* 254:297-314, 1999). HA and gp64 proteins get incorporated into the infected host cell membrane. During the budding process, the budding virions pick up the protein as the constituent viral envelops (Tani et al., *Virology* 279:343-353, 2001; Yang et al., *Mol Ther* 15:989-996, 2007). Therefore, influenza HA can be displayed on the surface of baculovirus (Jin et al., *PLoS ONE* 3:e3933, 2008; Lu et al., *Biochem Biophys Res Commun* 358:404-409, 2007; Prabakaran et al., *Virology* 380:412-420, 2008; Yang et al., *Mol Ther* 15:989-996, 2007).

VI. Influenza

Influenza viruses are segmented negative-strand RNA viruses that belong to the Orthomyxoviridae family. There are three types of influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Currently, sixteen subtypes of HA (H1-H16) and nine NA (N1-N9) antigenic variants are known for influenza A virus. Previously, only three subtypes were known to circulate in humans (H1N1, H1N2, and H3N2). However, in recent years, the pathogenic H5N1 subtype of avian influenza A has been reported to cross the species barrier and infect humans as documented in Hong Kong in 1997 and 2003, leading to the death of several patients.

In humans, the avian influenza virus infects cells of the respiratory tract as well as the intestinal tract, liver, spleen, kidneys and other organs. Symptoms of avian influenza infection include fever, respiratory difficulties including shortness of breath and cough, lymphopenia, diarrhea and difficulties regulating blood sugar levels. In contrast to seasonal influenza, the group most at risk is healthy adults which make up the bulk of the population. Due to the high pathogenicity of certain avian influenza A subtypes, particularly H5N1, and their demonstrated ability to cross over to infect humans, there is a significant economic and public health risk associated with these viral strains, including a real epidemic and pandemic threat. Currently, no effective vaccines for H5N1 infection are available.

The influenza A virus genome encodes nine structural proteins and one nonstructural (NS1) protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB 1 and PA), nucleoprotein (NP), neuraminidase (NA), hemagglutinin (subunits HA1 and HA2), the matrix proteins (M1 and M2) and the non-structural proteins (NS1 and NS2) (Krug et al., In "The Influenza Viruses," R. M. Krug, ed., Plenum Press, N.Y., 1989, pp. 89 152).

Influenza virus' ability to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

HA is a viral surface glycoprotein generally comprising approximately 560 amino acids and representing 25% of the total virus protein. It is responsible for adhesion of the viral particle to, and its penetration into, a host cell in the early stages of infection. Cleavage of the virus HA0 precursor into the HA1 and HA2 sub-fragments is a necessary step in order for the virus to infect a cell. Thus, cleavage is required in order to convert new virus particles in a host cell into virions capable of infecting new cells. Cleavage is known to occur during transport of the integral HA0 membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA1 and the carboxy terminal HA2. One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between virus and target cell membrane. This process is followed by fusion of the two membranes and entry of the virus into the target cell.

Proteolytic activation of HA involves cleavage at an arginine residue by a trypsin-like endoprotease, which is often an intracellular enzyme that is calcium dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acid in length, and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (Horimoto et al., *Clin Microbiol Rev.* 14(1):129-149, 2001).

In order to be packaged into progeny virions, viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., *J Virol,* 82:2295-2304, 2008). The M1 protein that lies within the envelope is thought to function in assembly and budding. A limited number of M2 proteins are integrated into the virions (Zebedee, *J. Virol.* 62:2762-2772, 1988). They form tetramers having H+ ion channel activity, and when activated by the low pH in endosomes, acidify the inside of the virion, facilitating its uncoating (Pinto et al., *Cell* 69:517-528, 1992). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable although it grew less efficiently than the parent virus in interferon-non-defective cells (Garcia-Sastre, *Virology* 252:324-330, 1998).

NS2 has been detected in virus particles (Richardson et al., *Arch. Virol.* 116:69-80, 1991; Yasuda et al., *Virology* 196:249-255, 1993). The average number of NS2 proteins in a virus particle was estimated to be 130-200 molecules. An in vitro binding assay shows direct protein-protein contact between M1 and NS2. NS2-M1 complexes have also been detected by immunoprecipitation in virus-infected cell lysates. The NS2 protein is thought to play a role in the export of RNP from the nucleus through interaction with M1 protein (Ward et al., *Arch. Virol.* 140:2067-2073, 1995).

VII. Baculovirus Display of Influenza Hemagglutinin

The present disclosure describes studies that demonstrate the efficiency of influenza HA displayed on the surface of baculovirus and its utility as a vaccine. Baculovirus surface display has previously been used for the analysis of protein-protein interaction (Sakihama et al., *PLoS ONE* 3:e4024, 2008), drug screening (Makela and Oker-Blom, *Comb Chem High Throughput Screen* 11:86-98, 2008), monoclonal antibody generation (Lindley et al., *J Immunol Methods* 234:123-135, 2000), as well as vaccine production (Fan et al., *J Virol Methods* 150:21-26, 2008; Lin et al., *Vaccine* 26:6361-6367, 2008; Prabakaran et al., *J Virol* 84:3201-3209, 2010; Yoshida et al., *Infect Immun* 77:1782-1789, 2009). Initially, vaccines were developed that fused epitopes or peptides to the coat protein of AcMNPV gp64, which resulted in surface display of these peptides on the baculovirus surface. Subsequently, it was found that some native viral envelope proteins can be displayed on the baculovirus surface even without the fusion with gp64, such as HIV-1 gp120 (Boublik et al., *Biotechnology (NY)* 13:1079-1084, 1995), influenza HA (Lu et al., *Biochem Biophys Res Commun* 358:404-409, 2007), vesicular stomatitis virus glycoprotein (Kitagawa et al., *J Virol* 79:3639-3652, 2005). However, so far no comprehensive studies have investigated whether fusion of native proteins results in efficient display on the baculovirus surface as a delivery vehicle for vaccines.

In the present disclosure, the SP, TM, and CT domains of gp64 were examined to enhance foreign antigen display on the baculovirus surface. The signal peptide of the membrane protein plays an important role in directing protein to the endoplasmic reticulum membrane and trafficking (Rapoport, *Science* 258:931-936, 1992). The TM domain of baculovirus envelope is critical for protein trafficking, membrane anchoring, membrane fusion, and viral budding (Lazarovits et al., *J Biol Chem* 265:4760-4767, 1990; Li and Blissard, *J Virol* 82:3329-3341, 2008). The CT domain of a viral envelope protein may influence envelope incorporation and virus budding, since the CT domains interact with the components of viral core (Schnell et al., *EMBO J* 17:1289-1296, 1998; Suomalainen et al., *J Virol* 66:4737-4747, 1992).

Figure 3:
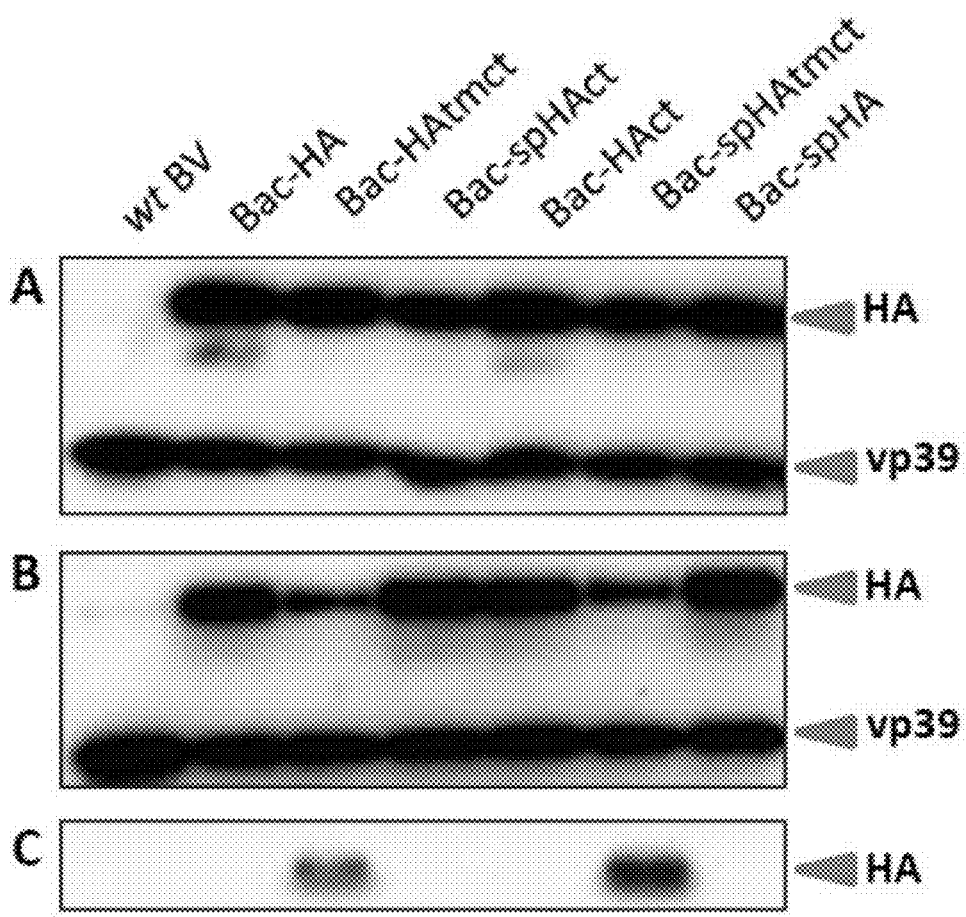
FIGS. 3A-3C: Western-blot assay of HA-displayed baculovirus. (A) Supernatants from infected Sf9 cells probed with HA and vp39 antibodies. (B) Pelleted rBV by ultracentrifugation probed with HA and vp39 antibodies. (C) Supernatants after ultracentrifugation of recombinant baculovirus (rBV) probed with HA antibody.

The CT domain of gp64 has been shown to enhance the incorporation of influenza HA into baculovirus (Yang et al., *Mol Ther* 15:989-996, 2007). However, prior to the present disclosure, it was not known if SP and TM domains of gp64 have similar functions. Therefore, six recombinant baculoviruses expressing six chimeric or native HAs were constructed. All six HAs were expressed, translocated to the infected cell surface and incorporated into baculovirus envelope. Importantly, all constructs expressed HA at similar levels (FIG. 3A), indicating that the substitutions of these three domains does not significantly affect HA expression. However, not all expressed HA were incorporated into mature baculovirus with equal efficiency (FIGS. 3B & 3C). The HA containing TM domain of gp64 resulted in unbound HA, indicating that TM domain of HA is important for HA incorporating into virions. Roth et al. reported that substitutions of TM domains of HA with VSV-G and herpes simplex virus glycoprotein C had minimal effect on the HA ectodomain (Roth et al., *J Cell Biol* 102:1271-1283, 1986), but replacement or mutation of the TM domain of HA affected its folding and stability, as well as virus-cell membrane fusion (Doyle et al., *J Cell Biol* 103:1193-11204, 1986; Lazarovits et al., *J Biol Chem* 265:4760-4767, 1990; Monsma and Blissard, *J Virol* 69:2583-2595, 1995). Hemagglutination titer of influenza virus can reflect the abundance of properly folded hemagglutinin on a viral particle. At equivalent virus titer, Bac-spHAct has the highest hemagglutination titer. Therefore, it was chosen for subsequent mouse studies.

The studies disclosed herein investigated the efficacy of HA-DBV as an influenza vaccine. There is a direct correlation between HAI titers and protection against influenza challenge. Yang et al. reported that HA displayed BV can successfully elicit functional antibodies although they did not analyze protection by challenging the immunized mice (Yang et al., *Mol Ther* 15:989-996, 2007). Prabakaran et al. reported that intranasal or gastrointestinal delivery of HA-DBV protected mice against H5N1 influenza virus infection (Prabakaran et al., *J Virol* 84:3201-3209, 2010; Prabakaran et al., *Virology* 380:412-420, 2008).

The current disclosure describes studies to investigate the dosage of HA-DBV as a vaccine in a mouse model and to compare live and inactivated HA-DBV. The results indicated that live HA-DBV elicits strong humoral immune responses, as indicated by the HAI titers, even at a low dose ($4 \times 10^6$ ifu/mouse), whereas the inactivated HA-DBV induces low HAI titers. After challenge, viral titers in lungs were determined on day 3 and day 6 post-challenge. It was found that all mice vaccinated with live Bac-spHAct had undetectable viral titers in their lungs on day 3 and 6 post challenge, suggesting that antibodies induced by live Bac-spHAct conferred sterilizing immunity. Most mice vaccinated with inactivated Bac-spHAct had detectable lung virus titers by day 3 post challenge. Some mice in the VLP-vaccinated group had detectable viral titers in their lungs, indicating that the efficacy of the live HA-DBV is superior to the VLP vaccine, which is most likely the result of the strong adjuvant property of baculovirus. All wt BV-vaccinated mice had lung viral titers similar to unvaccinated mice. Viral lung titers correlated with protection, mice with low viral titers were protected. Even though baculoviruses are unable to replicate in mammalian cells, only the live HA-DBV vaccines, not the inactivated ones, elicited high titer protective immune responses.

BV contains a large genome (80-200 kb) (Miller, *Bioessays* 11:91-95, 1989). This enables insertion of large foreign DNA fragments or construction of multivalent vaccines. Influenza viruses have many serotypes in nature. A single influenza infection may be sufficient to provide lifelong immunity to the invading strain or serotype, but cannot provide protection against emerging serotypes. H5N1 avian influenza virus has the potential to emerge as a pandemic threat in humans. So far, H5N1 influenza viruses are divisible into 10 clades on the basis of phylogenetic analysis of HA genes (Abdel-Ghafar et al., *N Engl J Med* 358:261-273, 2008). The cross-clade protections are very poor, so multivalent H5N1 influenza vaccines are critically important for preventing its spread. The major human infections were caused by clades 1, 2.1, 2.2 and 2.3. Therefore, an rBV was constructed that expressed four HAs derived from these four subclades of H5N1 influenza viruses. In a mouse study, it was found that monovalent H5N1 vaccine induced poor cross-clade antibody responses, but multivalent H5N1 vaccine elicited broadly-reactive antibody responses against all the HA subtypes included in the DBV. These correlated with protection rates and viral titers in lung. Some mice did not have detectable HAI titers, but survived from lethal dose virus challenge, which may be a result of cellular immune responses clearing some virally infected cells. Previous studies have reported that virus-specific CTL play an important role in the recovery and protection during influenza virus infection, especially when a protective antibody titer is absent (Graham et al., *J Exp Med* 186:2063-8, 1997; McMichael et al., *N Engl J Med* 309:13-17, 1983).

To investigate influenza-specific T cell responses elicited by HA-DBV, IFNγ-ELISPOT and MHC-I pentamer staining were performed. On day 6 post-challenge, the recall of HA-specific IFNγ-secreting memory T cells were detected in HA-DBV vaccinated mice, but not in wt BV vaccinated mice. Little or no NP-specific IFNγ-secreting T cells were detected in all vaccinated mice since the NP protein was not included in the HA-DBV (Hikono et al., *Immunol Rev* 211:119-132, 2006; Kedzierska et al., *Immunol Rev* 211:133-145, 2006). On day 9 post infection, which is close to the peak of the primary response, NP-specific IFNγ-secreting T cells can be measured. Meanwhile, there was a much higher frequency of HA-specific IFNγ-secreting T cells in HA-DBV vaccinated mice compared to wt BV vaccinated mice. Similarly, the frequency of HA-pentamer positive $CD8^+$ T cells was significantly higher in HA-DBV vaccinated mice compared to wt BV vaccinated mice on both day 6 and 9 post-challenge. These data indicated that HA-specific $CD8^+$ T cells were induced by the HA-DBV vaccine and memory T cells were present in the immunized mice. Even though cellular immune responses cannot confer sterilizing immunity, they are able to reduce the severity of infection and lower morbidity and mortality rates (Flynn et al., *Immunity* 8:683-691, 1998), and antigen-specific memory T cells are able to rapidly respond to a secondary virus infection (Hikono et al., *Immunol Rev* 211: 119-132, 2006). Furthermore, cellular immune responses to the conserved epitopes contained in vaccines may provide cross-protective immunity against different subtypes of influenza virus infection (Heiny et al., *PLoS ONE* 2:e1190, 2007; Lee et al., *J Clin Invest* 118:3478-3490, 2008; Thomas et al., *Emerg Infect Dis* 12:48-54, 2006).

DBVs have several advantages as a vaccine platform. DBVs are easy to generate, grow efficiently without the addition of fetal calf serum, and they are stable under refrigeration. Displayed proteins, expressed from either insect or mammalian cells have similar protein processing and post-translational modifications and they form native structures on the BV surface. The baculovirus genome allows for insertion of large foreign DNA segments or the construction of multivalent vaccines. There is little or no observable cytopathic effect following administration of high doses of BV. Taken together, HA-DBV can be used as a vaccine platform for multiple infectious disease pathogens.

VIII. Administration of Recombinant Baculoviruses and Compositions Thereof

Recombinant baculoviruses, or compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Recombinant baculoviruses, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent influenza virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation. In some embodiments, the dose is about $10^4$ to about $10^9$ ifu, such as about $10^6$ to about $10^8$ ifu. In particular examples, the dose is about $4 \times 10^6$ to about $1 \times 10^8$.

Provided herein are pharmaceutical compositions which include a therapeutically effective amount of the recombinant baculoviruses alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The recombinant baculoviruses described herein can be administered alone or in combination with other therapeutic agents to enhance antigenicity. For example, the recombinant viruses can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

The following examples are provided to illustrate certain particular features and/or embodiments. These examples should not be construed to limit the disclosure to the particular features or embodiments described.

EXAMPLES

Example 1

Materials and Methods

This example describes the experimental procedures used for the studies described in Example 2.

Cells and Viruses.

*Spodoptera frugiperda* (Sf9) cells were propagated at 28° C. in Sf-900II serum free medium. Cells were infected by each recombinant baculovirus at a multiplicity of infection (MOI) of 0.1-1.0 and virus supernatants were collected 4 days post-infection. Influenza viruses used in this study included the subtype H1N1, A/Puerto Rico/8/1934 (PR8), or the PR8-reassortant H5N1 viruses representing A/Vietnam/1203/2004 (VN/04), A/Indonesia/5/05 (IN/05), A/Whooper Swan/244/05 (WS/05), and A/Anhui/1/05 HA (AH/05). Each reassortant virus expressed the HA and NA derived from H5N1 viruses and the internal protein genes came from A/PR/8/1934 donor virus. Each virus was used to infect mice as previously described (Bright et al., *PLoS ONE* 3:e1501, 2008).

Construction of Plasmids and Recombinant Baculoviruses.

The SP, TM, and CT domains of the gp64 gene were amplified from bacmid DNA by PCR. The full-length or ectodomain of HA genes from mouse-adapted PR8 were amplified by PCR from one plasmid containing full-length HA of the PR8 virus. A series of plasmids encoding the SP, TM and CT regions of gp64 and various portions of HA were generated using the following strategy. Nine primers (A-I as shown in Table 1) were used to generate the chimeric HA-gp64 genes. Primers A and B were used to amplify the gene fragment encoding the gp64 SP. Primers C and D were used to amplify the gene fragment encoding gp64 TM and CT. Primers E and F were used to amplify full-length HA of PR8. Primers G and H were used to amplify the ectodomain of PR8 HA (without SP, TM and CT). Primers E and I were used to amplify PR8 HA, but the CT was derived from gp64. Primers E and H were used to amplify PR8 HA without TM and CT. Primers G and F were used to amplify PR8 HA without SP. Primers G and I were used to amplify PR8 HA without SP, and CT was derived from gp64. Appropriate fragments were serially inserted into pFastBac™ transfer vector (Invitrogen, Carlsbad, Calif.) in frame. Thus, each construct expresses chimeric PR8 HA proteins (FIGS. 1A and B). All recombinant baculoviruses were generated using the Bac-to-Bac system (Invitrogen, Carlsbad, Calif.) and designated as Bac-HA, Bac-spHA, Bac-spHAct, Bac-HAct, Bac-HAtmct and Bac-spHAtmct.

The recombinant virus selection and amplification were performed following standard protocols. The infectious titers of recombinant baculoviruses were determined by the Bac-PAK Baculovirus Rapid Titer Kit (Clontech, Mountain View, Calif.) and were expressed as infectious units per milliliter (ifu/ml).

Purification of HA-Displayed Baculovirus.

The recombinant baculoviruses were produced by infecting Sf9 cells at an MOI of 0.1. Supernatants were collected 4 days after infection and were clarified by centrifugation at 3000×g for 10 minutes at 4° C. to remove cell debris. Viral particles were precipitated via ultracentrifugation (100,000×g through 20% glycerol, w/v) for 4 hours at 4° C. The pellets were subsequently resuspended in PBS and stored at 4° C. The viral titer was determined using the BacPAK Baculovirus Rapid Titer Kit.

Hemagglutination Assay for HA-Displayed Baculoviruses.

A series of 2-fold dilutions of HA-displayed baculovirus in PBS was prepared and incubated at 25° C. for 30 minutes with 50 μl of 1% turkey red blood cells (tRBCs), or 1 hour with 50 μl of 1% horse red blood cells (hRBCs) (Lampire Biologicals, Pipersville, Pa., USA). The extent of hemagglutination was inspected visually, and the highest dilution capable of agglutinating red blood cells was determined.

Hemadsorption Assays.

Insect Sf9 cells (infected or uninfected with recombinant baculovirus containing HA genes or no HA genes) were diluted to a concentration of $1\times10^6$ cell/ml in PBS. Cells (100 μl) were mixed with 10 μl of 1% red blood cells and shaken gently for 10 minutes at room temperature. Then 10 μl of the suspension was pipetted on a glass plate and observed by microscopy (Wang et al., *Vaccine* 24:2176-2185, 2006).

TABLE 1

Primers used for PR8-HA displaying constructs

| Primer | Primer sequence (5'-3') | Primer annotation |
|---|---|---|
| A | CGC<u>TGATCA</u>GCCACCATGCTACTGGT AAATCAGTCACAC (SEQ ID NO: 1) | Forward primer for gp64 Signal peptide with Bcl I site |
| B | CGAGCTCGTCGACAGGCCTGAATTCG <u>GATCC</u>CGCAAAGGCAGAATGCGCC (SEQ ID NO: 2) | Reverse primer for gp64 Signal peptide with multiple cloning sites |
| C | CAGGCCTGTCGACGAGCTCGCGGCCG CGTTCATGTTTGGTCATGTAG (SEQ ID NO: 3) | Forward primer for gp64 TM-CTD with multiple cloning sites |
| D | AAG<u>CGGCCG</u>TTAATATTGTCTATTAC GGTTTCTAATC (SEQ ID NO: 4) | Reverse primer for gp64 TM-CTD with Eag I site |
| E | CAA<u>GTCGAC</u>GCCACCATGAAGGCAAA CCTACTGGTCC (SEQ ID NO: 5) | Forward primer for HA of PR8 virus with Sal I site |
| F | CTC<u>GCGGCCGC</u>TCAGATGCATATTCT GCACTGC (SEQ ID NO: 6) | Reverse primer for HA of PR8 virus with Not I site |
| G | GCG<u>GGATCC</u>GCAGACACAATATGTAT AGGC (SEQ ID NO: 7) | Forward primer for PR8 HA without SP (with BamH I) |
| H | AAC<u>GCGGCCGC</u>AATCTGATAGATCCC CATTGATTC (SEQ ID NO: 8) | Reverse primer for PR8 HA without TM, CT (with Not I) |
| I | GGC<u>TCTAGA</u>TTA*ATATTGTCTATTACGG TTTCTACACATCCAGAAACTGATTGC* (SEQ ID NO: 9) | Reverse primer for PR8 HA with CT of gp64 (with Xba I) |

Underlined sequences are restriction enzyme sites. Bolded sequences are start or stop codons.

Western Blot Analysis.

The supernatants from rBV infected Sf9 cells or purified baculoviruses were subjected to Western blot analysis. Mouse anti-PR8 HA polyclonal antibody and mouse anti-vp39 monoclonal antibody was used to detect proteins. The primary antibodies were detected with goat anti-mouse monoclonal antibodies conjugated with horseradish peroxidase (1:5000, SouthernBiotech, Birmingham, Ala.).

Vaccinations.

Female BALB/c mice (*Mus musculis*, females, 6-8 weeks old) were purchased from Harlan Sprague Dawley (Indianapolis, Ind., USA). Mice were housed in microisolator units and allowed free access to food and water and were cared for under USDA guidelines for laboratory animals. Mice (10 groups, 15 mice per group) were vaccinated with live or BPL inactivated Bac-spHAct at 3 different doses ($1 \times 10^8$, $2 \times 10^7$, and $4 \times 10^6$ ifu/mouse), with wild-type (wt) baculovirus ($1 \times 10^8$ ifu), mammalian cell derived VLPs (6 µg), or PBS as a control, via intramuscular injection at week 0 and boosted with the same doses at week 3 (Table 2).

The HAI titer was determined by the reciprocal of the last dilution that contained non-agglutinated RBCs. Positive and negative serum controls were included on each plate.

Challenge and Viral Load.

Challenge infections were performed as previously described (Bright et al., *PLoS ONE* 3:e1501, 2008). At 3 weeks after the final immunization, ketamine-anesthetized mice were intranasally infected with 1,500 plaque forming units (pfu) of A/PR/8/1934 virus (equivalent to 10× the 50% lethal dose [$LD_{50}$]) in 50 µl of PBS. Mice were weighed daily and analyzed for disease (i.e. weight loss, ruffling fur, inactivity). Mice that lost greater than 20% of body weight were humanely euthanized. One day 3 and 6 post-challenge, five mice from each group were sacrificed and the lungs were harvested. The tissues were homogenized, and viral load was determined by plaque assay on Madin-Darby canine kidney (MDCK) cells as previously described (Bright et al., *PLoS ONE* 3:e1501, 2008).

TABLE 2

Mouse study groups and protective efficacy

| Vaccines used in each mouse group | Immunization dose (ifu) | Virus & dose used for challenge (pfu) | Clinical signs** | Protection (%) |
|---|---|---|---|---|
| PR8 HA-displayed BV | | | | |
| G1: Live Bac-spHAct | $1 \times 10^8$ | A/PR8 ($1.5 \times 10^3$) | Healthy | 100 |
| G2: Live Bac-spHAct | $2 \times 10^7$ | A/PR8 ($1.5 \times 10^3$) | Healthy | 100 |
| G3: Live Bac-spHAct | $4 \times 10^6$ | A/PR8 ($1.5 \times 10^3$) | Healthy | 100 |
| G4: Live wt baculovirus | $1 \times 10^8$ | A/PR8 ($1.5 \times 10^3$) | Sick (+++) | 0 |
| G5: Inactivated Bac-spHAct | $1 \times 10^8$ | A/PR8 ($1.5 \times 10^3$) | Healthy | 100 |
| G6: Inactivated Bac-spHAct | $2 \times 10^7$ | A/PR8 ($1.5 \times 10^3$) | Healthy | 100 |
| G7: Inactivated Bac-spHAct | $4 \times 10^6$ | A/PR8 ($1.5 \times 10^3$) | Sick (+) | 100 |
| G8: Inactivated wt baculovirus | $1 \times 10^8$ | A/PR8 ($1.5 \times 10^3$) | Sick (+++) | 0 |
| G9: PR8 VLP* | 6 µg | A/PR8 ($1.5 \times 10^3$) | Healthy | 100 |
| G10: PBS | | A/PR8 ($1.5 \times 10^3$) | Sick (+++) | 0 |
| H5N1 HA-displayed BV | | | | |
| G1: Live Bac-HA2.2 | $1 \times 10^7$ | A/VN/04 ($5 \times 10^3$) | Sick (++) | 60 |
| G2: Live Bac-HA2.2 | $1 \times 10^7$ | A/IN/05 ($5 \times 10^3$) | Sick (++) | 40 |
| G3: Live Bac-HA2.2 | $1 \times 10^7$ | A/WS/05 ($5 \times 10^3$) | Healthy | 100 |
| G4: Live Bac-HA1.0/2.1/2.2/2.3 | $1 \times 10^7$ | A/VN/04 ($5 \times 10^3$) | Healthy | 100 |
| G5: Live Bac-HA1.0/2.1/2.2/2.3 | $1 \times 10^7$ | A/IN/05 ($5 \times 10^3$) | Healthy | 100 |
| G6: Live Bac-HA1.0/2.1/2.2/2.3 | $1 \times 10^7$ | A/WS/05 ($5 \times 10^3$) | Healthy | 100 |
| G7: Live wt baculovirus | $1 \times 10^7$ | A/VN/04 ($5 \times 10^3$) | Sick (+++) | 0 |
| G8: Live wt baculovirus | $1 \times 10^7$ | A/IN/05 ($5 \times 10^3$) | Sick (+++) | 0 |
| G9: Live wt baculovirus | $1 \times 10^7$ | A/WS/05 ($5 \times 10^3$) | Sick (+++) | 0 |

*VLP was produced by transfecting 293T cells with three plasmids expressing HA, NA and M1 of PR8 virus.
**Mice with +++ signs showed severe illness. Clinical signs were determined by body weight losses and mouse symptoms of illness. +++, lost in body weight of over 20% and riffling fur; ++, some mice died and some had only10~20% weight loss with riffling fur; +, 10~20% decreases in body weight, with riffling fur; healthy, <5% body weight changes and no riffling fur.

Hemagglutination Inhibition (HAI) Assays.

Blood samples were collected from anesthetized mice via retro-orbital plexus puncture before immunization and at 2 weeks after each immunization (week 2, 5). After the blood samples were clotted and centrifuged, serum samples were collected. The HAI assay was used to assess functional antibodies to HA able to inhibit agglutination of erythrocytes. To inactivate non-specific inhibitors, aliquots of each serum sample were treated with receptor-destroying enzyme (RDE; Denka Seiken Co., Japan) overnight at 37° C., heat-inactivated at 56° C. for 30 minutes, and diluted 1:5 with PBS (Crevar et al., Virol J 5:131, 2008). RDE-treated sera (25 µl) were diluted serially two-fold in v-bottom 96-well microtiter plates. An equal volume of influenza virus, adjusted to approximately 8 HA units/50 µl was added to each well. The plates were covered and incubated at room temperature for 30 minutes followed by the addition of 50 µl freshly prepared 1% tRBCs or hRBCs in PBS. The plates were mixed by agitation, covered, and allowed to set for 30 minutes or 1 hour at 25° C.

Construction of Multiple-HA-Displayed Baculovirus.

Figure 2A:
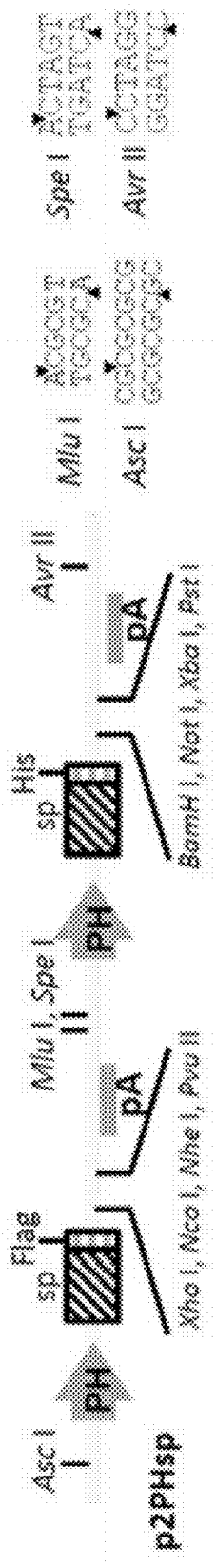
FIGS. 2A-2C: Construction of the four-unit transfer vector pHA1.0/2.1/2.2/2.3. (A) Dual-PH promoter transfer vector with SP of gp64 and two multiple cloning sites. (B) Stepwise construction of pHA1.0/2.1/2.2/2.3. (C) Schematic showing the baculovirus transfer vector for the tetravalent H5N1 vaccine.
Figure 2B:
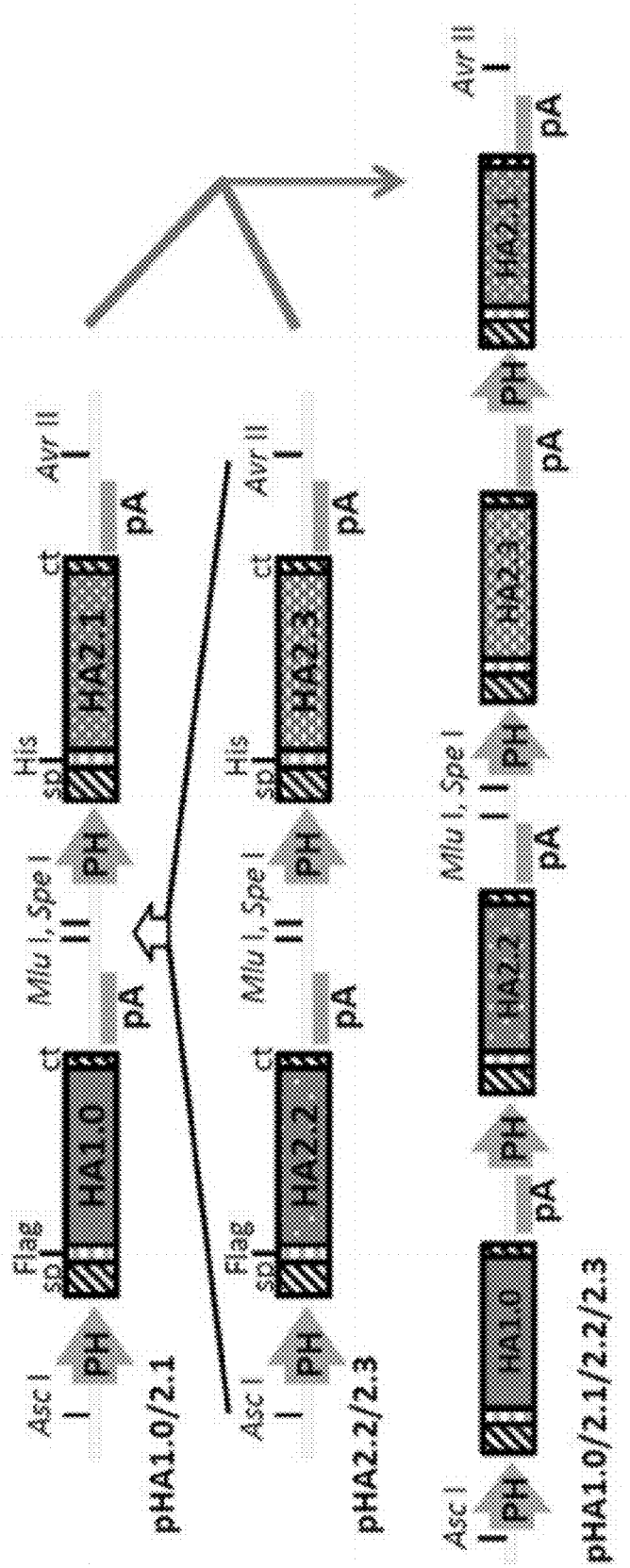
Figure 2C:
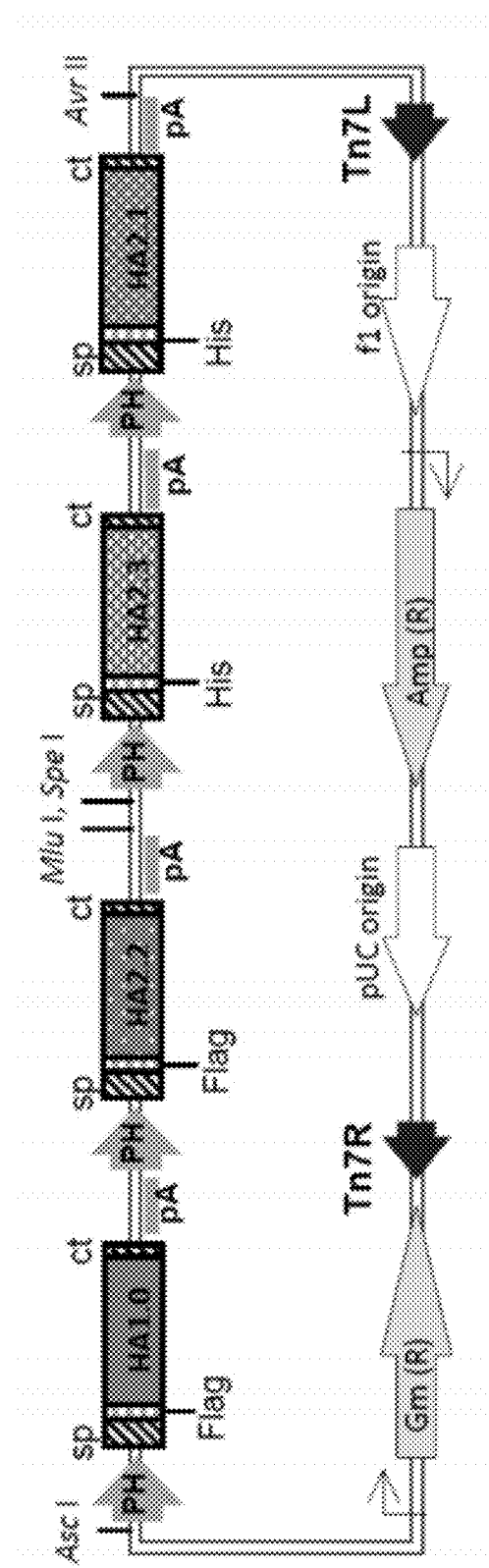

In order to introduce four expression cassettes into baculovirus, pFastBac™ Dual plasmid was firstly modified to contain two PH promoters and two multiple cloning sites (p2PH). The SP region of gp64 with Flag or His tag was inserted into p2PH to make the transfer vector p2PHsp. Two pairs of compatible restriction sites (Asc I-Mlu I, Spe I-Avr II) were introduced into p2PHsp as shown in FIG. 2A. Appropriate ectodomain of HAs from four H5N1 influenza viruses were PCR amplified from the following virus strains: A/Vietnam/1203/2005 (clade 1), A/Indonesia/5/05 (clade 2.1), A/Whooper Swan/244/05 (clade 2.2), and A/Anhui/1/05 HA (clade 2.3). The four-HA plasmid pHA1.0/2.1/2.2/2.3 was constructed in two stages (FIG. 2B). (i) First, the two dual-HA plasmids were constructed. HA fragments of VN/04 and IN/05 were cloned into one p2PHsp to obtain plasmid pHA1.0/2.1. HA fragments of WS/05 and AH/05 were cloned into another p2PHsp to obtain plasmid pHA2.2/2.3. (ii) The fragment containing the HA2.2 and HA2.3 cassettes, along with their promoter-terminator, was excised with Asc I and Avr II from pHA2.2/2.3 and cloned in between the Mlu I and Spe I sites in the pHA1.0/2.1 to obtain the four-HA plasmid pHA1.0/2.1/2.2/2.3 (p4HA). Recombinant baculoviruses were generated using the Bac-to-Bac system and designated as Bac-HA1.0/2.1, Bac-HA2.2/2.3 and Bac-HA1.0/2.1/2.2/2.3 (Bac-4HA). A schematic of the completed baculovirus transfer vector is shown in FIG. 2C. Multiple-HA-displayed baculoviruses were propagated and purified as above. Protein expression was checked by Western-blot, hemagglutination assay and hemadsorption assay.

Evaluation for the Tetravalent H5N1 Vaccine Candidate in Mouse Model.

Mice (9 groups, 12 mice per group) were intramuscularly vaccinated with Bac-HA2.2, Bac-4HA, or wt BV ($1\times10^7$ ifu/mouse) at week 0 and week 3 (Table 2). Serum was collected at weeks 2 and 5 to determine anti-HA-specific antibody titer. For virus challenge, anesthetized mice were infected intranasally with 5000 pfu of A/VN/04, A/IN/05, or A/WS/05 viruses in 50 µl of PBS per mouse at 3 weeks after the final immunization. Five mice from each group were sacrificed on day 3 post-challenge for examining virus replication in lungs. Five mice in each group were monitored daily for survival and morbidity post infection. Mice that lost greater than 20% of body weight were euthanized. The ability of each vaccine to protect against homologous or heterologous challenge was compared to separate groups of wt-baculovirus vaccinated control mice that were subsequently challenged with each reassortant virus. The remaining mice in each group were used to determine the elicitation of anti-HA specific cellular responses by murine IFNγ enzyme linked immunospot (IFNγ-ELISPOT) assay (R & D Systems, Minneapolis, Minn., USA) and MHC class I pentamer staining (ProImmune, Oxford, UK).

IFNγ-ELISPOT Assays.

Spleens were harvested from vaccinated mice at day 6 and day 9 post-challenge and splenocytes were isolated for IFNγ-ELISPOT assays as previously described (Ross et al., PLoS One 4:e6032, 2009). Briefly, pre-coated anti-IFNγ plates were incubated (25° C. for 2 hours) with cRPMI (200 ml) and then incubated with freshly isolated splenocytes ($5\times10^5$/well). Splenocytes were stimulated with the single peptides representing the immunodominant H2-Kd CD8$^+$ T cell epitopes $HA_{533}$ and $NP_{147}$ or as a negative control the non-specific $Ova_{257}$ peptide (Pepscan Presto, Leystad, Netherlands). Both $HA_{533}$ and $NP_{147}$ peptides were originally derived from the PR8 (H1N1) virus, but they are conserved in H5N1 influenza viruses (Ross et al., PLoS One 4:e6032, 2009). Additional wells were stimulated with PMA (50 ng)/ionomycin (500 ng) or were mock stimulated. In addition, IL-2 was added to all wells (10 units/ml). After 48-hour stimulation, plates were washed with PBS-Tween (3×) and were incubated overnight at 4° C. with anti-mIFNγ antibody. The plates were washed and then incubated (25° C. for 2 hours) with streptavidin conjugated to alkaline phosphatase. Following extensive washing, cytokine/antibody complexes were incubated at room temperature with BCIP/NBT chromagen until spots appeared. The plates were rinsed with $dH_2O$ and air-dried at 25° C. Spots were counted by an ImmunoSpot™ ELISPOT reader (Cellular Technology Ltd., Cleveland, Ohio, USA).

Flow Cytometry.

In order to detect influenza-specific CD8$^+$ T cells, MHC class I pentamer staining was employed. The CD8$^+$ T cell responses to $NP_{147}$ are dominant followed by $HA_{533}$ responses in influenza virus infected BALB/c mice. Lung lymphocytes were isolated from infected mice at day 6 and 9 post-challenge as previously described (Ross et al., PLoS One 4:e6032, 2009). The cells were washed with FACS buffer (PBS, 1% FBS, 0.1% sodium azide) and then blocked with anti-CD16/CD32 mouse Fc receptor block (BD Biosciences, San Jose, Calif., USA), followed by staining with a murine MHC-I encoded allele Kd-specific pentamer for the $HA_{533}$ epitope or $NP_{147}$ epitope conjugated to phycoerythrin (PE). Lymphocytes were subsequently stained with anti-CD8 antibodies conjugated to Pacific Blue, anti-CD3 antibodies conjugated to PerCP and anti-CD19 antibodies conjugated with APC-Cy7 (BD Biosciences, San Jose, Calif., USA). The cells are then incubated with a viability dye (Molecular Probes, Invitrogen, Eugene, Oreg., USA). Once the surface staining was complete the cells were washed with FACS buffer, then fixed in 1% formalin/PBS and the cells were acquired using a LSRII flow cytometer (BD Biosciences, San Jose, Calif., USA).

Example 2

Hemagglutinin Displayed Baculovirus Protects Against Highly Pathogenic Influenza This example describes the finding that vaccination with tetravalent HA-DBV stimulates strong humoral and cellular immune responses and protects mice against lethal H5N1 influenza virus challenge.

Construction of Recombinant Baculoviruses.

In order to investigate the gp64 components that may influence incorporation of HA on to baculovirus, six novel chimeric genes were constructed. The coding sequences for the signal peptide, transmembrane and cytoplasmic tail domains of HA were replaced with those of gp64 (FIG. 1B): Bac-HA, expressing full length HA; Bac-spHA, expressing ectodomain of HA with SP derived from gp64; Bac-spHAct, expressing ectodomain of HA with SP and CT derived from gp64; Bac-HAct, expressing HA with CT derived from gp64; Bac-HAtmct, expressing ectodomain of HA with TM and CT derived from gp64; Bac-spHAtmct, expressing ectodomain of HA with SP, TM and CT derived from gp64. All constructs were derived from the mouse adapted influenza virus A/PR/8/34 (H1N1). The hypothesis was that the SP of the gp64 would facilitate the translocation of the chimeric HA to the insect cell plasma membrane and the TM and CT domains of gp64 would stabilize the chimeric HA incorporated into virus envelope.

Confirmation of HA Expression and Incorporation into Baculovirus.

Figure 11:
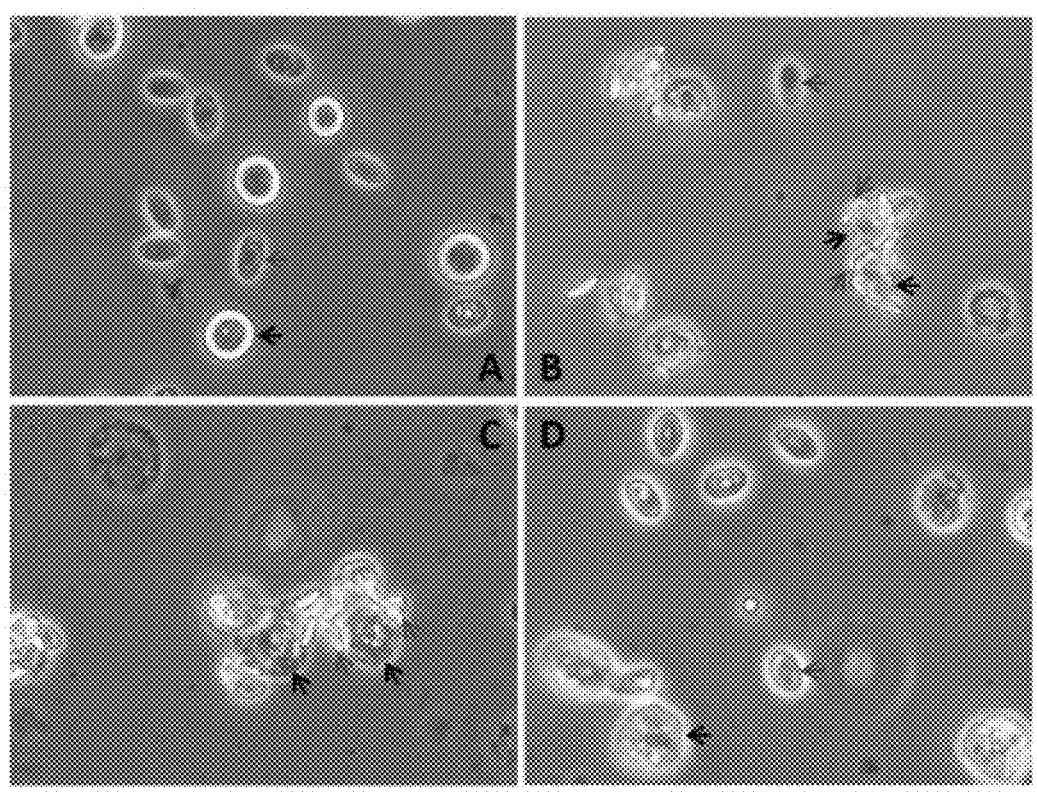
FIGS. 11A-11D: Expressed HA anchoring on the infected insect cells by hemadsorption assay. Shown are uninfected Sf9 cells (A), Sf9 cells infected with Bac-spHAct (B), Sf9 cells infected with Bac-4HA (C) and Sf9 cells infected with BV without HA (D). Light arrows indicate the red blood cells; dark arrows indicate Sf9 cells.

To determine whether the HA expressed by BV is properly translocated to the insect cell surface, BV-infected and uninfected insect cells were incubated with tRBCs for agglutination. Approximately 80% RBCs were absorbed on the insect cells infected with baculoviruses containing HA genes. In contrast, no RBC absorption was observed for the uninfected insect cells or cells infected with baculovirus without HA gene (FIG. 11). Therefore, the HA proteins expressed in insect cells were translocated to the cell surface, and were properly folded maintaining their hemagglutination activity.

To confirm the expression of each chimeric HA, Sf9 cells were infected with these recombinant baculoviruses at a MOI ~1.0, and harvested at 4 days post-infection and the expressed HAs were quantified by scanning densitometry (FIG. 3A). Equivalent amounts (ifu) of recombinant baculoviruses were loaded in each well and the quantities of incorporated HA were normalized on the basis of equal amounts of vp39 (the major baculovirus capsid protein). HA proteins were expressed at similar levels by all six constructs (FIG. 3A).

To confirm that each HA was incorporated on the envelope of baculoviruses, supernatants from infected Sf9 cells were used to perform hemagglutination assays. All recombinant baculovirus containing an HA gene bound RBCs, but baculoviruses without an HA gene did not agglutinate tRBCs. Furthermore, at the same titer of baculovirus ($5\times10^7$ ifu/ml), Bac-spHAct had the highest HA titer (1:64) while Bac-spHAtmct and Bac-HAtmct had the lowest HA titer (1:2), indicating that the different domains of gp64 (SP, TM and CT) affected the efficiency of HA incorporation into baculovirus. In order to verify whether all expressed HAs are incorporated into baculovirus, HA-DBVs from infected Sf9 cells were pelleted by ultracentrifugation and the supernatants and pelleted fractions were analyzed. Four DBV pellets from cells infected with Bac-HA, Bac-spHA, Bac-spHAct, and Bac-HAct incorporated similar amounts of each chimeric HA, while two DBV pellets (Bac-HAtmct and Bac-spHAtmct) incorporated about 50% less HAs (FIG. 3B). Supernatants from Bac-spHAtmct and Bac-HAtmct had some unbound HAs while the other four constructs did not have detectable HAs after ultracentrifugation (FIG. 3C). Therefore, Bac-spHAct was chosen as the template for further vaccine studies.

HA-DBVs Elicit Hemagglutination-Inhibition Activity.

Figure 4:
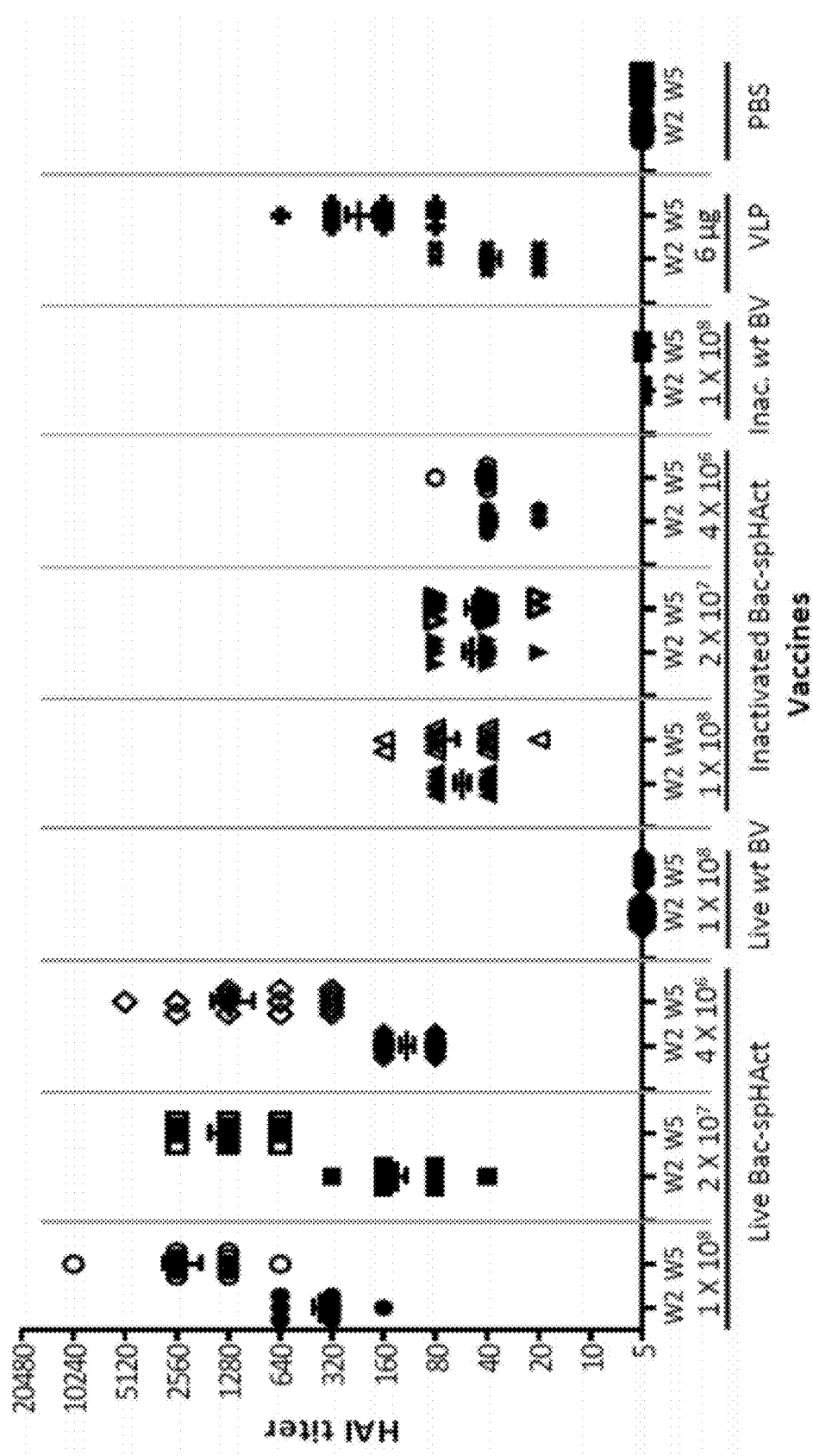
FIG. 4: Hemagglutination-inhibition (HAI) titers. Mice (n=15/group) immunized intramuscularly with live/inactivated Bac-spHAct, wt BV, VLPs or mock vaccination. Week 2 (W2), and week 5 (W5) serum HAI antibody responses were assessed against PR8 virus. Bars indicate geometric mean titer (GMT)+/−SEM.

Mice (BALB/c, n=15/group) were vaccinated with either (1) live HA-DBV (Bac-spHAct) with the HA derived from the A/PR/8/34; (2) the same BV inactivated with BPL; (3) wt BV; (4) purified PR8 VLPs produced in mammalian cells; or (5) mock vaccinated with PBS. Serum samples were evaluated for the ability to inhibit PR8 influenza virus induced hemagglutination of tRBCs. All Bac-spHAct vaccinated mice had detectable HAI titer against PR8 virus from serum collected at weeks 2 and 5 (FIG. 4). Two weeks after the first vaccination, the average HAI titers for live Bac-spHAct groups ($1\times10^8$, $2\times10^7$, and $4\times10^6$ ifu/mouse) were between 118 and 373, while the average HAI titers for BPL-inactivated Bac-spHAct groups ($1\times10^8$, $2\times10^7$, and $4\times10^6$ ifu/mouse, same doses but inactivated) were between 38 and 56. Following the second vaccination, HAI titers increased from the first dose (~10 fold) in mice vaccinated with live Bac-spHAct vaccine, while the HAI titers from mice vaccinated with BPL-inactivated Bac-spHAct vaccines did not increase significantly. Mice that were immunized with the live Bac-spHAct vaccinated groups had significantly higher HAI titers than the mice vaccinated with the BPL-inactivated Bac-spHAct. Remarkably, the live Bac-spHAct vaccinated mice had higher HAI titers compared to VLP vaccinated mice after the primary and boost immunization. As expected, there were no HA inhibiting antibody responses elicited in mice that were immunized with wt BV.

Viral Titers in Lungs of Vaccinated Mice Post Challenge.

Figure 5:
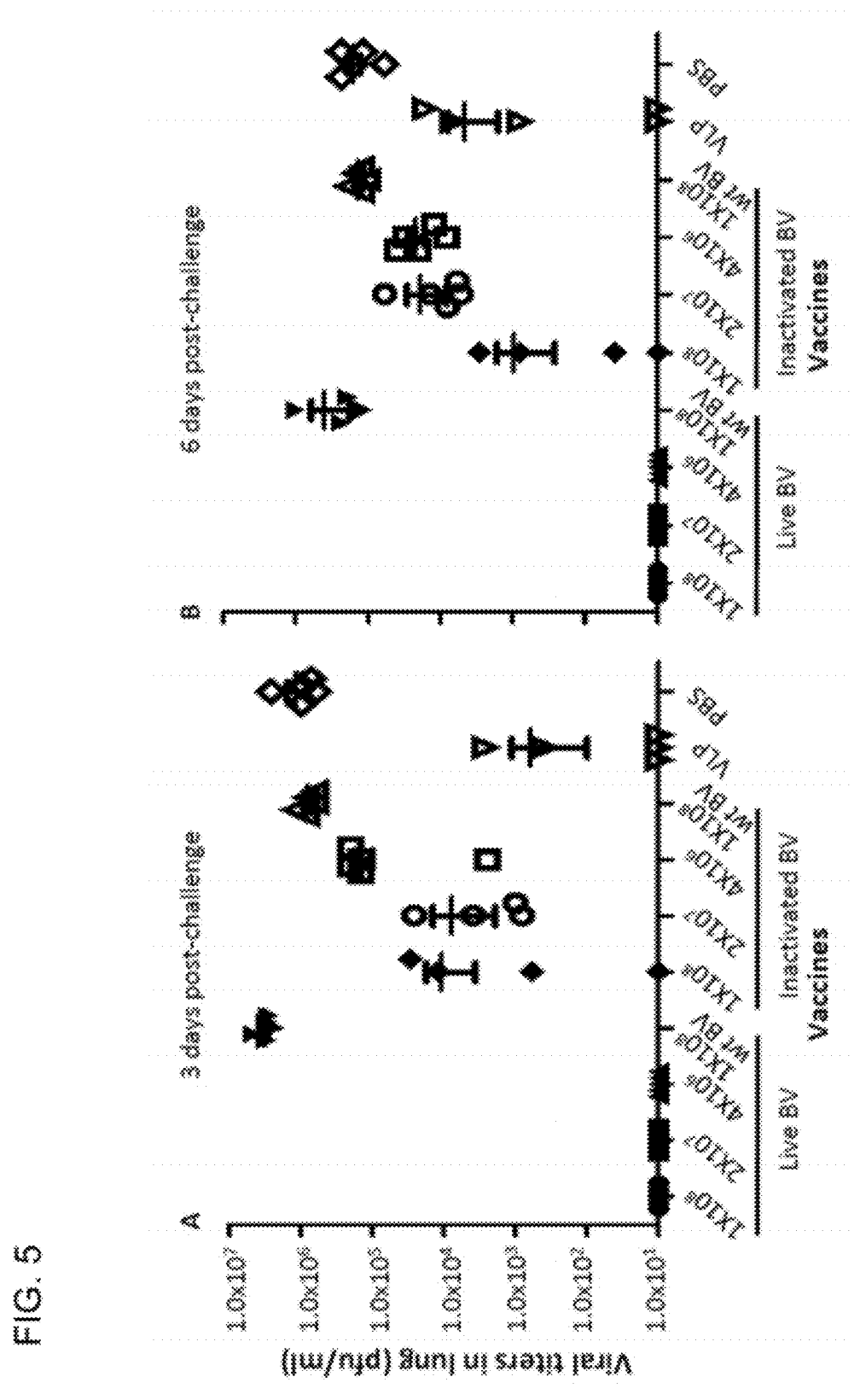

Lung viral titers were determined at days 3 and 6 post-challenge (FIG. 5). Unvaccinated mice and mice vaccinated with live or inactivated wt BV had high viral titers in their lungs (~$1\times10^6$ pfu/ml). Mice which were immunized with a mammalian cell-derived VLP vaccine showed a 1000-fold reduction of viral titer. However, mice vaccinated with live Bac-spHAct, irrespective of the dose, did not have detectable virus (<10 pfu/ml) in their lungs. In contrast, mice vaccinated with inactivated Bac-spHAct had virus titers that ranged from $1\times10^3$ to $1\times10^5$ pfu/ml at day 3 (FIG. 5A). By day 6, mice vaccinated with inactivated Bac-spHAct with $1\times10^8$ ifu showed a reduction in lung viral titer, whereas mice vaccinated with a lower dose of inactivated Bac-spHAct maintained similar viral titers as day 3 (FIG. 5B). Mice vaccinated with the live HA-DBV elicited immune responses that blocked PR8 virus infection, even if immunized with a very low dose ($4\times10^6$ ifu/mouse). Therefore, additional studies were performed using a live HA-DBV regimen.

Immunization with Bac-spHAct Confers Protection from Lethal PR8 Virus Challenge.

Figure 6:
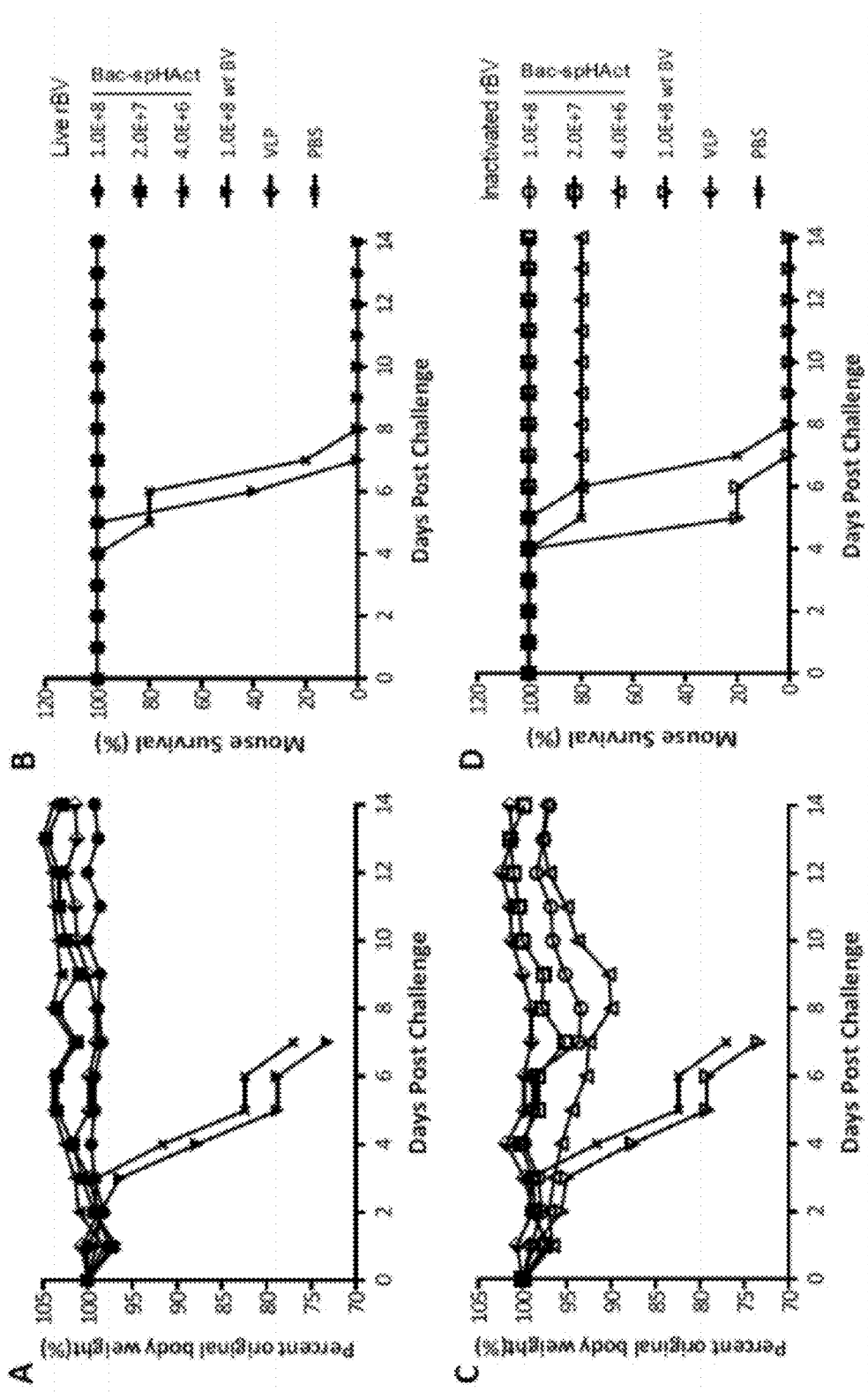
FIGS. 6A-6D: Protection of mice from lethal PR8 challenge. At week 3 after the final immunization, immunized mice (n=5/group) were intranasally infected with a lethal dose of mouse-adapted PR8 virus (10 $LD_{50}$). Mice were monitored daily for 14 days. (A) Body weight changes of mice immunized with live Bac-spHAct, wt BV, VLP or PBS. (B) Percent survival of mice immunized with live Bac-spHAct, wt BV, VLP or PBS. (C) Body weight changes of mice immunized with β-propiolactone (BPL)-inactivated Bac-spHAct, wt BV, VLP or PBS. (D) Percent survival of mice immunized with BPL-inactivated Bac-spHAct, wt BV, VLP or PBS.

To evaluate the protective efficacy of different vaccine strategies of Bac-spHAct, mice were challenged intranasally with a lethal dose of PR8 virus. All mice vaccinated with either live or BPL inactivated wt BV or non-vaccinated mice lost greater than 20% of their original body weight and died from complications associated with infection by day 5-8 post challenge (FIG. 6). All mice vaccinated with live Bac-spHAct or VLP vaccines were protected from lethal challenge without weight loss, regardless of vaccination dose (FIGS. 6A and B), whereas mice vaccinated with inactivated Bac-spHAct lost some weight following challenge (FIG. 6C), and one out of five mice vaccinated with the lowest dose of inactivated Bac-spHAct ($4\times10^6$ ifu/mouse) died after challenge (FIG. 6D). All the other mice vaccinated with Bac-spHAct survived virus challenge.

HAI Antibody Titers Elicited by Bac-HA2.2 or Bac-4HA Vaccines.

Figure 7:
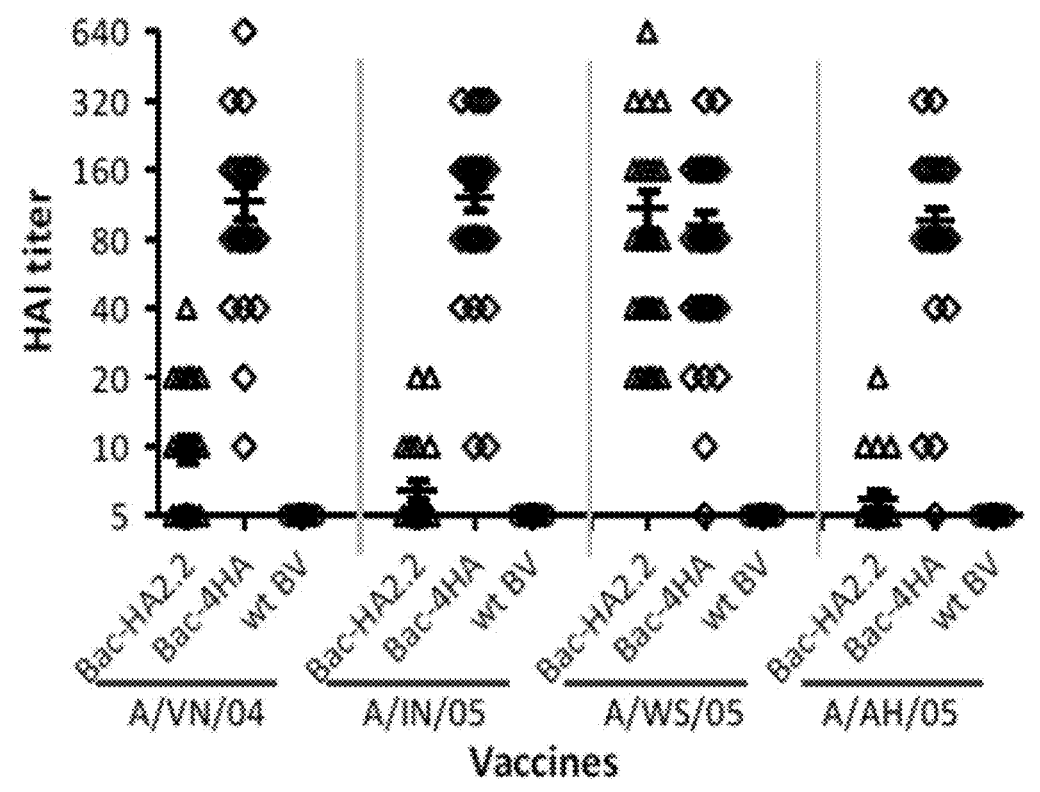

Since the comparison of PR8 HA-displayed constructs indicated that SP and CT domains of gp64 can enhance the HA incorporation into baculovirus, HA-DBV were constructed to contain chimeric HAs derived from four subclades of H5N1 influenza viruses which were fused with SP and CT domains of gp64. The HA displayed on the surface of baculovirus maintain hemagglutination activity. Mice were vaccinated with live H5N1 HA-DBV ($1\times10^7$ ifu/mouse) of either a monovalent HA-DBV (Bac-HA2.2) or a tetravalent HA-DBV (Bac-4HA). Two weeks after primary vaccination, the HAI titers to all H5N1 viruses were undetectable or low (<1:10), regardless of the vaccine administered. Following the second vaccination, the HAI titers of all vaccine groups became detectable (FIG. 7). At week 5, mice vaccinated with the monovalent HA-DBV (Bac-HA2.2) had an average HAI titer of 1:100 against A/WS/05, low ($\leq$1:20) HAI titer against heterologous viruses (VN/04, IN/05, AH/05). In contrast, mice vaccinated with the tetravalent HA-DBV (Bac-4HA) had HAI titers against all four viruses (VN/04, IN/05, WS/05, AH/05), with a seroconversion rate ranging from 86-94%. As expected, wt BV vaccinated mice had no detectable HAI titers.

Protection Against Heterologous or Homologous H5N1 Viral Challenge.

Figure 8:
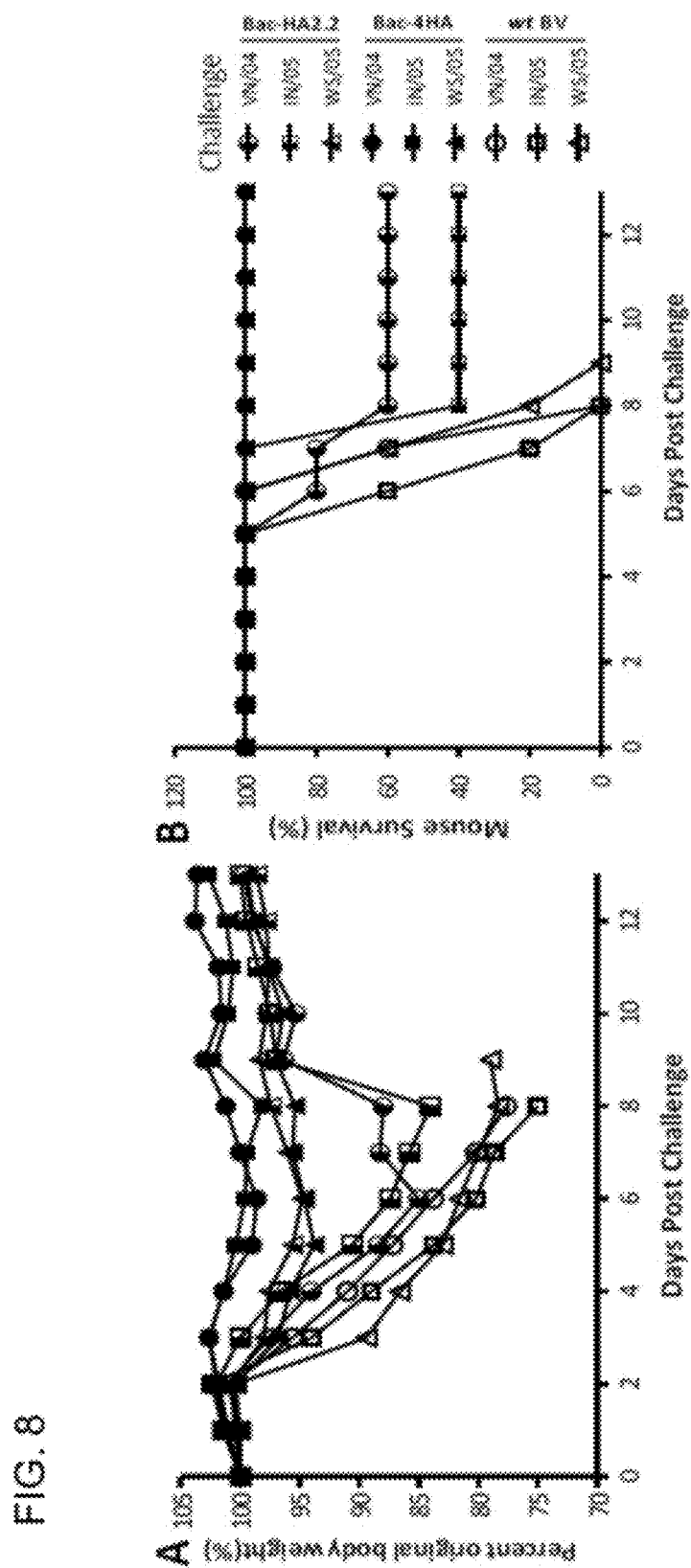
FIGS. 8A-8B: Protection of mice from lethal H5N1 virus challenge. At week 3 after the final immunization, immunized mice (n=5/group) were intranasally infected with a lethal dose of VN/04, IN/05 or WS/05 virus. Mice were monitored daily for 13 days. Shown are body weight changes (A) and percent survival (B) after challenge.

To test whether immunization protects mice from a lethal infection with reassortant H5N1 influenza viruses, mice that received either Bac-HA2.2, Bac-4HA, or wt BV vaccine were challenged intranasally with lethal doses of either VN/04, IN/05 or WS/05 viruses (FIG. 8 and Table 2). All mice vaccinated with Bac-4HA were protected from death following lethal challenge with VN/04, IN/05 or WS/05 reassortant viruses. All mice vaccinated with Bac-HA2.2 were protected from lethal challenge with homologous WS/05, whereas only 60% of the mice infected with heterologous VN/04 and 40% of mice infected with IN/05 were protected. All mice vaccinated with wt BV lost greater than 20% of their original weight and had to be euthanized or died from complications associated with infection by day 6-9 post-challenge.

Figure 9:
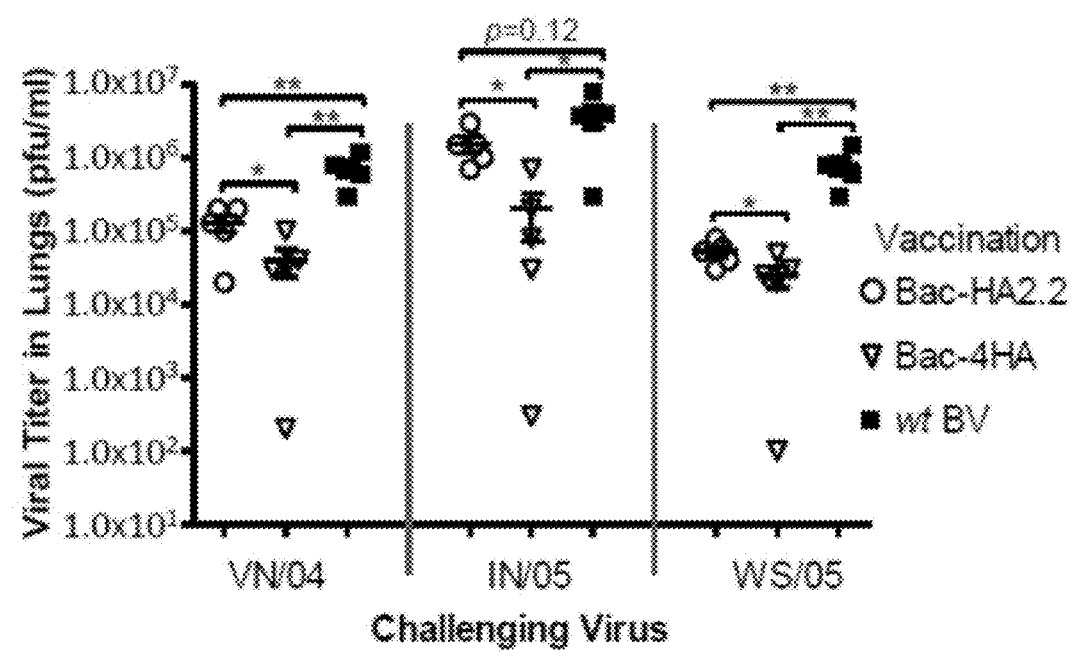

Lung viral titers at day 3 post-challenge were analyzed to determine virus replication in the lung (FIG. 9). The wt BV immunized mice groups showed high viral titer (~$1\times10^6$ pfu/ml), regardless of the challenge virus, while significantly lower viral titers were detected in the Bac-4HA vaccinated groups. High titers of virus replication were also observed in the mice that received Bac-HA2.2, albeit lower than the titers observed in mice immunized with wt BV. These results indicate that Bac-4HA can induce protective immune responses that can protect from challenge with VN/04, IN/05 or WS/05 influenza viruses, while Bac-HA2.2 can induce partial protective immune responses against heterologous virus (VN/04, IN/05).

Cell-Mediated Immunity Elicited by HA-DBV.

Figure 10:
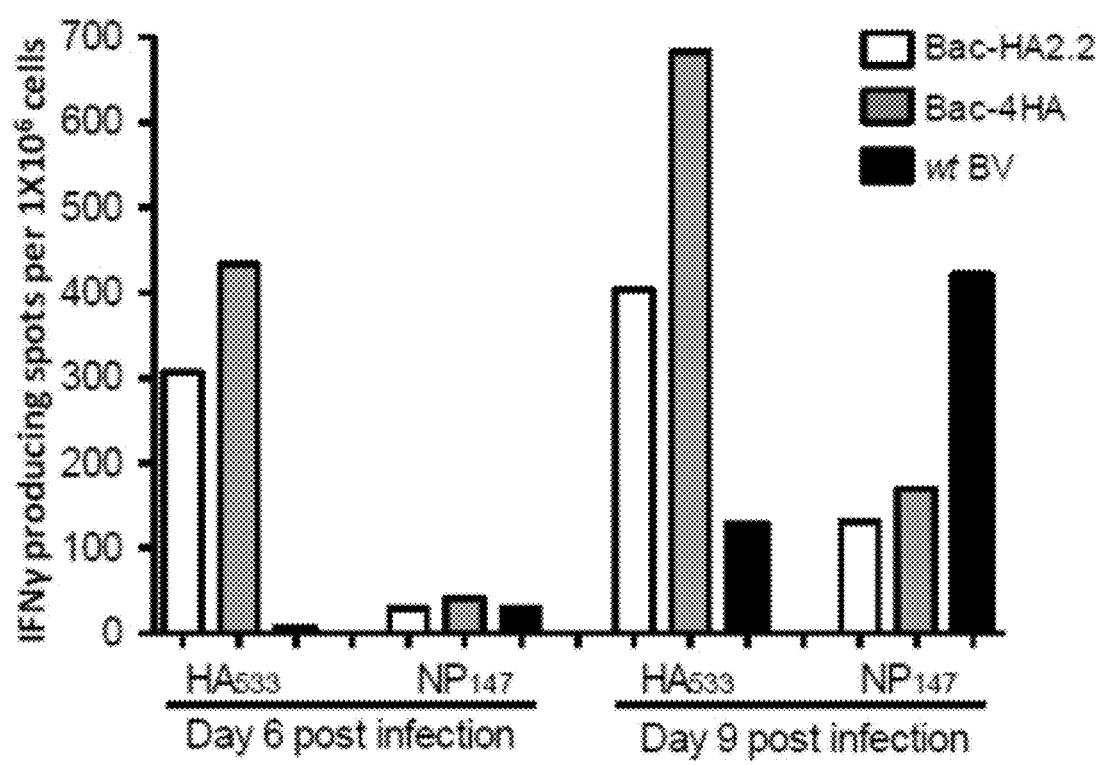
FIG. 10: IFNγ-ELISPOT assays. Splenocytes were collected on day 6 and 9 post-infection with IN/05. Each sample was stimulated with $HA_{533}$, $NP_{147}$, and Ova peptides.

The magnitude of T-cell responses induced by HA-DBV was determined using IFNγ-ELISPOT and flow cytometry. Splenocytes were harvested at 6 and 9 days post challenge and stimulated in vitro with H2d-restricted CD8+ T cell specific peptide $HA_{533}$ (Ross et al., *PLoS One* 4:e6032, 2009). After HA peptide stimulation, wt BV vaccinated mice had T cell responses similar to the negative controls (unstimulated or stimulated with irrelevant peptide) (FIG. 10). In contrast, mice vaccinated with Bac-HA2.2 or Bac-4HA vaccines had significantly higher IFNγ responses (300-460 spots/1×10$^6$ cells) following HA peptide stimulation (FIG. 10). After $NP_{147}$ peptide stimulation, IFNγ responses were detected at low levels in all vaccinated mice on day 6 post infection, which is to be expected since the NP epitope is not present in the vaccine. The ELISPOT assay was performed also on day 9 post challenge, which is the peak of the T cell response during a primary infection. With $HA_{533}$ peptide stimulation, mice vaccinated with Bac-HA2.2 or Bac-4HA had 400-700 spots while mice vaccinated with wt BV had only 130 spots per 1×10$^6$ cells, which is expected because the T cell response in HA-DBV vaccinated mice is a recall response that must be stronger than the primary response in wt BV vaccinated mice. With $NP_{147}$ peptide stimulation, mice vaccinated with Bac-HA2.2 or Bac-4HA had 150 spots while mice vaccinated with wt BV had 400 spots per 1×10$^6$ cells. This discovery is most likely due to the fact that wt BV vaccinated mice were not protected from infection with the influenza virus which resulted in a robust activation of influenza-specific T cell responses, whereas in the HA-DBV vaccinated mice a large proportion of the challenge virus was neutralized by antibodies or cleared by influenza specific T cells, therefore resulting in a lower frequency of NP-specific T cells on day 9 post challenge.

To determine the influenza-specific T cell response in lung, lung cells were collected at day 6 and 9 post-challenge by IN/05 and analyzed via staining with a pentamer specific for T cells recognizing the $HA_{533}$ or $NP_{147}$ epitopes (Ross et al., *PLoS One* 4:e6032, 2009) (FIG. 12A & FIG. 12B). On day 6 post-challenge, the percentage of NP-pentamer+/CD8+ T cells in all vaccinated/infected mice was similar to unvaccinated/uninfected mice. About 2.6% HA-pentamer+/CD8+ T cells were detected in the lungs of mice vaccinated with Bac-HA2.2 and Bac-4HA. As expected, there were no HA-pentamer+/CD8+ T cells in wt BV vaccinated mice (Table 3). On day 9 post-challenge, HA-DBV vaccinated mice had 4.6-5.4% NP-pentamer+/CD8+ T cells in their lungs, whereas wt BV vaccinated mice had 15% of their lung lymphocytes stain positive for the NP-pentamer. This revealed the same phenomenon as IFNγ-ELISPOT results on day 9 post-challenge. In contrast, 26.1% of cells collected from mice vaccinated with Bac-HA2.2 and 20.8% from Bac-4HA vaccinated mice were HA-pentamer+/CD8+, and only 3.1% were HA-pentamer+/CD8+ in wt BV vaccinated mice, since recall immune responses in the former were stronger than primary immune responses in the later.

TABLE 3

Percentage of pentamer positive CD8+ T cells in lung

| Challenge after vaccination | Day 6 post infection | | | Day 9 post infection | | |
|---|---|---|---|---|---|---|
| | Bac-HA2.2 | Bac-4HA | wt BV | Bac-HA2.2 | Bac-4HA | wt BV |
| HA pentamer+/CD8+ (%) | 2.6 | 2.6 | 0.1 | 26.1 | 20.8 | 1.3 |
| NP pentamer+/CD8+ (%) | 0.2 | 0.5 | 0.6 | 5.4 | 4.6 | 15 |

Example 3

Tetravalent H5N1 Influenza Vaccine Sequences

This example provides the nucleotide sequences encoding the HA fusion proteins for the tetravalent H5N1 influenza vaccine based on baculovirus display as described in the previous examples. The nucleotide and amino acid sequences of each chimeric HA is set forth in the Sequence Listing as SEQ ID NOs: 10-17. The baculovirus transfer vector of the tetravalent H5N1 influenza vaccine is depicted in FIG. 2C.

Provided below are the nucleotide sequences of each chimeric HA gene. The underlined portion at the beginning of each sequence is the signal peptide domain of baculovirus gp64. The underlined portion at the end of each sequence is the cytoplasmic tail domain of baculovirus gp64. The middle portion of each sequence encodes a tag (His tag or Flag tag) and a restriction site (XhoI or BamHI) and the ectodomain and transmembrane domain of influenza HA. Tables 4-7 provide the sequence identifiers and nucleotide and amino acid residues of each component of the chimeric HA.

Chimeric HA Sequence of A/Vietnam/1203/2004 (VN/04, Clade 1):

(SEQ ID NO: 10)
ATGCTACTGGTAAATCAGTCACACCAAGGCTTCAATAAGGAACACACAAG

CAAGATGGTAAGCGCTATTGTTTTATATGTGCTTTTGGCGGCGGCGGCGC

ATTCTGCCTTTGCGGTCGACTACAAAGACGATGACGACAAGCTCGAGGAT

CAGATTTGCATTGGTTACCATGCAAACAACTCGACAGAGCAGGTTGACAC

AATAATGGAAAAGAACGTTACTGTTACACATGCCCAAGACATACTGGAAA

AGAAACACAACGGGAAGCTCTGCGATCTAGATGGAGTGAAGCCTCTAATT

TTGAGAGATTGTAGCGTAGCTGGATGGCTCCTCGGAAACCCAATGTGTGA

CGAATTCATCAATGTGCCGGAATGGTCTTACATAGTGGAGAAGGCCAATC

CAGTCAATGACCTCTGTTACCCAGGGGATTTCAATGACTATGAAGAATTG

AAACACCTATTGAGCAGAATAAACCATTTTGAGAAAATTCAGATCATCCC

CAAAAGTTCTTGGTCCAGTCATGAAGCCTCATTAGGGGTGAGCTCAGCAT

GTCCATACCAGGGAAAGTCCTCCTTTTTCAGAAATGTGGTATGGCTTATC

AAAAAGAACAGTACATACCCAACAATAAAGAGGAGCTACAATAATACCAA

CCAAGAAGATCTTTTGGTACTGTGGGGGATTCACCATCCTAATGATGCGG

CAGAGCAGACAAAGCTCTATCAAAACCCAACCACCTATATTTCCGTTGGG

ACATCAACACTAAACCAGAGATTGGTACCAAGAATAGCTACTAGATCCAA

AGTAAACGGGCAAAGTGGAAGGATGGAGTTCTTCTGGACAATTTTAAAGC

-continued
CGAATGATGCAATCAACTTCGAGAGTAATGGAAATTTCATTGCTCCAGAA

TATGCATACAAAATTGTCAAGAAAGGGGACTCAACAATTATGAAAAGTGA

ATTGGAATATGGTAACTGCAACACCAAGTGTCAAACTCCAATGGGGCGA

TAAACTCTAGCATGCCATTCCACAATATACACCCTCTCACCATTGGGGAA

TGCCCCAAATATGTGAAATCAAACAGATTAGTCCTTGCGACTGGGCTCAG

AAATAGCCCTCAAAGAGAGAAGAAGAAAAAAGAGAGGATTATTTGGAG

CTATAGCAGGTTTTATAGAGGGAGGATGGCAGGGAATGGTAGATGGTTGG

TATGGGTACCACCATAGCAATGAGCAGGGGAGTGGGTACGCTGCAGACAA

AGAATCCACTCAAAAGGCAATAGATGGAGTCACCAATAAGGTCAACTCGA

TCATTGACAAAATGAACACTCAGTTTGAGGCCGTTGGAAGGGAATTTAAC

AACTTAGAAAGGAGAATAGAGAATTTAAACAAGAAGATGGAAGACGGGTT

CCTAGATGTCTGGACTTATAATGCTGAACTTCTGGTTCTCATGGAAAATG

AGAGAACTCTAGACTTTCATGACTCAAATGTCAAGAACCTTTACGACAAG

GTCCGACTACAGCTTAGGGATAATGCAAAGGAGCTGGGTAACGGTTGTTT

CGAGTTCTATCATAAATGTGATAATGAATGTATGGAAAGTGTAAGAAATG

GAACGTATGACTACCCGCAGTATTCAGAAGAAGCGAGACTAAAAAGAGAG

GAAATAAGTGGAGTAAAATTGGAATCAATAGGAATTTACCAAATACTGTC

AATTTATTCTACAGTGGCGAGTTCCCTAGCACTGGCAATCATGGTAGCTG

GTCTATCCTTATGG<u>AGAAACCGTAATAGACAATATTAA</u>

The amino acid sequence of the chimeric VN/04 HA is set forth herein as SEQ ID NO: 11. The nucleotide and amino acid positions of the gp64 signal sequence, HA ectodomain/transmembrane (TM) domain and gp64 cytoplasmic tail domain of chimeric VN/04 are listed in Table 4 below.

TABLE 4

Chimeric VN/04 HA

| Component | Nucleotides residues of SEQ ID NO: 10 | Amino acid residues of SEQ ID NO: 11 |
|---|---|---|
| gp64 signal peptide | 1-114 | 1-38 |
| Flag tag | 118-141 | 40-47 |
| XhoI restriction site | 142-147 | 48-49 |
| HA ectodomain and TM | 148-1764 | 50-588 |
| gp64 cytoplasmic domain | 1765-1788 | 589-595 |

Chimeric HA Sequence of A/Indonesia/5/05 (IN/05, Clade 2.1):

(SEQ ID NO: 12)
<u>ATGCTACTGGTAAATCAGTCACACCAAGGCTTCAATAAGGAACACACAAG</u>

<u>CAAGATGGTAAGCGCTATTGTTTTATATGTGCTTTTGGCGGCGGCGGCGC</u>

<u>ATTCTGCCTTTGCG</u>CATCACCACCATCACCATCACGGATCCGATCAGATT

TGCATTGGTTACCATGCAAACAATTCAACAGAGCAGGTTGACACAATCAT

GGAAAAGAACGTTACTGTTACACATGCCCAAGACATACTGGAAAAGACAC

ACAACGGGAAGCTCTGCGATCTAGATGGAGTGAAGCCTCTAATTTTAAGA

GATTGTAGTGTAGCTGGATGGCTCCTCGGGAACCCAATGTGTGACGAATT

CATCAATGTACCGGAATGGTCTTACATAGTGGAGAAGGCCAATCCAACCA

ATGACCTCTGTTACCCAGGGAGTTTCAACGACTATGAAGAACTGAAACAC

CTATTGAGCAGAATAAACCATTTTGAGAAAATTCAAATCATCCCCAAAAG

TTCTTGGTCCGATCATGAAGCCTCATCAGGAGTGAGCTCAGCATGTCCAT

ACCTGGGAAGTCCCTCCTTTTTTAGAAATGTGGTATGGCTTATCAAAAAG

AACAGTACATACCCAACAATAAAGAAAAGCTACAATAATACCAACCAAGA

AGATCTTTTGGTACTGTGGGGAATTCACCATCCTAATGATGCGGCAGAGC

AGACAAGGCTATATCAAAACCCAACCACCTATATTTCCATTGGGACATCA

ACACTAAACCAGAGATTGGTACCAAAAATAGCTACTAGATCCAAAGTAAA

CGGGCAAAGTGGAAGGATGGAGTTCTTCTGGACAATTTTAAAACCTAATG

ATGCAATCAACTTCGAGAGTAATGGAAATTTCATTGCTCCAGAATATGCA

TACAAAATTGTCAAGAAAGGGGACTCAGCAATTATGAAAAGTGAATTGGA

ATATGGTAACTGCAACACCAAGTGTCAAACTCCAATGGGGGCGATAAACT

CTAGTATGCCATTCCACAACATACACCCTCTCACCATCGGGGAATGCCCC

AAATATGTGAAATCAAACAGATTAGTCCTTGCAACAGGGCTCAGAAATAG

CCCTCAAAGAGAGCAGAAGAAAAAGAGAGGACTATTTGGAGCTATAG

CAGGTTTTATAGAGGGAGGATGGCAGGGAATGGTAGATGGTTGGTATGGG

TACCACCATAGCAATGAGCAGGGGAGTGGGTACGCTGCAGACAAAGAATC

CACTCAAAAGGCAATAGATGGAGTCACCAATAAGGTCAACTCAATCATTG

ACAAAATGAACACTCAGTTTGAGGCCGTTGGAAGGGAATTTAATAACTTA

GAAAGGAGAATAGAGAATTTAAACAAGAAGATGGAAGACGGGTTTCTAGA

TGTCTGGACTTATAATGCCGAACTTCTGGTTCTCATGGAAAATGAGAGAA

CTCTAGACTTTCATGACTCAAATGTTAAGAACCTCTACGACAAGGTCCGA

CTACAGCTTAGGGATAATGCAAAGGAGCTGGGTAACGGTTGTTTCGAGTT

CTATCACAAATGTGATAATGAATGTATGGAAAGTATAAGAAACGGAACGT

ACAACTATCCGCAGTATTCAGAAGAAGCAAGATTAAAAAGAGAGGAAATA

AGTGGGGTAAAATTGGAATCAATAGGAACTTACCAAATACTGTCAATTTA

TTCAACAGTGGCGAGTTCCCTAGCACTGGCAATCATGATGGCTGGTCTAT

CTTTGTGG<u>AGAAACCGTAATAGACAATATTAA</u>

The amino acid sequence of the chimeric IN/05 HA is set forth herein as SEQ ID NO: 13. The nucleotide and amino acid positions of the gp64 signal sequence, HA ectodomain/transmembrane (TM) domain and gp64 cytoplasmic tail domain of chimeric IN/05 are listed in Table 5 below.

TABLE 5

Chimeric IN/05 HA

| Component | Nucleotides residues of SEQ ID NO: 12 | Amino acid residues of SEQ ID NO: 13 |
|---|---|---|
| gp64 signal peptide | 1-114 | 1-38 |
| His tag | 115-135 | 39-45 |
| BamHI restriction site | 136-141 | 46-47 |
| HA ectodomain and TM | 142-1758 | 48-586 |
| gp64 cytoplasmic domain | 1759-1782 | 587-593 |

Chimeric HA Sequence of A/Whooper Swan/244/Mongolia/05 (WS/05, Clade 2.2):

(SEQ ID NO: 14)

ATGCTACTGGTAAATCAGTCACACCAAGGCTTCAATAAGGAACACACAAG

CAAGATGGTAAGCGCTATTGTTTTATATGTGCTTTTGGCGGCGGCGGCGC

ATTCTGCCTTTGCGGTCGACTACAAAGACGATGACGACAAGCTCGAGGAT

CAGATTTGCATTGGTTACCATGCAAACAACTCGACAGAGCAGGTTGACAC

AATAATGGAAAAGAACGTCACTGTTACACACGCGCAAGACATACTGGAAA

AGACACACAACGGGAAACTCTGCGATCTAGATGGAGTGAAGCCTCTAATT

TTAAGAGATTGTAGTGTAGCTGGATGGCTCCTCGGGAACCCAATGTGTGA

CGAATTCCTCAATGTGCCGGAATGGTCTTACATAGTGGAGAAGATCAATC

CAGCCAATGACCTCTGTTACCCAGGGAATTTCAACGACTATGAAGAACTG

AAACACCTATTGAGCAGAATAAACCATTTTGAGAAAATTCAGATCATCCC

CAAAAGTTCTTGGTCAGATCATGAAGCCTCATCAGGGGTGAGCTCAGCAT

GTCCATACCAGGGAAGGTCCTCCTTTTTTAGAAATGTGGTATGGCTTATC

AAAAAGGACAATGCATACCCAACAATAAAGAGAAGTTACAATAATACCAA

CCAAGAAGATCTTTTGGTACTGTGGGGATTCACCATCCAAATGATGCGG

CAGAGCAGACAAGGCTCTATCAAAACCCAACCACCTATATTTCCGTTGGG

ACATCAACACTAAACCAGAGACTGGTACCAAAAATAGCTACTAGATCCAA

GGTAAACGGGCAAAGTGGAAGGATGGAGTTCTTTTGGACAATTTTAAAAC

CGAATGATGCAATAAACTTTGAGAGTAATGGAAATTTCATTGCTCCAGAA

AATGCATACAAAATTGTCAAGAAAGGGGACTCAACAATTATGAAAAGTGA

ATTGGAATATGGTAACTGCAACACCAAGTGTCAAACTCCAATAGGGGCGA

TAAACTCTAGTATGCCATTCCACAACATCCACCCTCTCACCATCGGGGAA

TGCCCCAAATATGTGAAATCAAACAGATTAGTCCTTGCGACTGGGCTCAG

AAATAGCCCTCAAATTGAAACTAGAGGATTATTTGGAGCTATAGCAGGTT

TTATAGAGGGAGGATGGCAGGGAATGGTAGATGGTTGGTATGGGTACCAC

CATAGCAACGAGCAGGGGAGTGGGTACGCTGCAGACAAAGAATCCACTCA

AAAGGCAATAGATGGAGTCACCAATAAGGTCAACTCGATCATTGACAAAA

TGAACACTCAGTTTGAGGCTGTTGGAAGGGAATTTAATAACTTAGAAAGG

AGAATAGAAAATTTAAACAAGAAGATGGAAGACGGATTCCTAGATGTCTG

GACTTATAATGCTGAACTTCTGGTTCTCATGGAAAATGAGAGAACTCTAG

ACTTTCATGACTCAAATGTCAAGAACCTTTACGACAAGGTCCGACTACAG

CTTAGGGATAATGCAAAGGAGCTTGGTAACGGTTGTTTCGAGTTCTATCA

TAGATGTGATAATGAATGTATGGAAAGTGTAAGAAACGGAACGTATGACT

ACCCGCAGTATTCAGAAGAAGCAAGATTAAAAAGAGAGGAAATAAGTGGA

GTAAAATTGGAATCAATAGGAACTTACCAAATACTGTCAATTTATTCAAC

AGTGGCGAGCTCCCTAGCACTGGCAATCATGGTGGCTGGTCTATCTTTAT

GGAGAAACCGTAATAGACAATATTAA

The amino acid sequence of the chimeric WS/05 HA is set forth herein as SEQ ID NO: 15. The nucleotide and amino acid positions of the gp64 signal sequence, HA ectodomain/transmembrane (TM) domain and gp64 cytoplasmic tail domain of chimeric WS/05 are listed in Table 6 below.

TABLE 6

| | Chimeric WS/05 HA | |
|---|---|---|
| Component | Nucleotides residues of SEQ ID NO: 14 | Amino acid residues of SEQ ID NO: 15 |
| gp64 signal peptide | 1-114 | 1-38 |
| Flag tag | 118-141 | 40-47 |
| XhoI restriction site | 142-147 | 48-49 |
| HA ectodomain and TM | 148-1752 | 50-584 |
| gp64 cytoplasmic domain | 1753-1776 | 585-591 |

Chimeric HA Sequence of A/Anhui/1/05 HA (AH/05, Clade 2.3):

(SEQ ID NO: 16)

ATGCTACTGGTAAATCAGTCACACCAAGGCTTCAATAAGGAACACACAAG

CAAGATGGTAAGCGCTATTGTTTTATATGTGCTTTTGGCGGCGGCGGCGC

ATTCTGCCTTTGCGCATCACCACCATCACCATCACGGATCCGATCAGATT

TGCATTGGTTACCATGCAAACAACTCGACAGAGCAGGTTGACACAATAAT

GGAAAAGAACGTTACTGTTACACATGCCCAAGACATACTGGAAAAGACAC

ACAACGGGAAGCTCTGCGATCTAGATGGAGTGAAGCCTCTGATTTTAAGA

GATTGTAGTGTAGCTGGATGGCTCCTCGGGAACCCAATGTGTGACGAATT

CATCAATGTGCCGGAATGGTCTTACATAGTGGAGAAGGCCAACCCAGCCA

ATGACCTCTGTTACCCAGGGAATTTCAACGACTATGAAGAACTGAAACAC

CTATTGAGCAGAATAAACCATTTTGAGAAAATTCAGATCATCCCCAAAAG

TTCTTGGTCCGATCATGAAGCCTCATCAGGGGTGAGCTCAGCATGTCCAT

ACCAGGGAACGCCCTCCTTTTTCAGAAATGTGGTATGGCTTATCAAAAAG

AACAATACATACCCAACAATAAAGAGAAGCTACAATAATACCAACCAGGA

AGATCTTTTGATACTGTGGGGATTCATCATTCTAATGATGCGGCAGAGC

AGACAAAGCTCTATCAAAACCCAACCACCTATATTTCCGTTGGGACATCA

ACACTAAACCAGAGATTGGTACCAAAAATAGCTACTAGATCCAAAGTAAA

CGGGCAAAGTGGAAGGATGGATTTCTTCTGGACAATTTTAAAACCGAATG

ATGCAATCAACTTCGAGAGTAATGGAAATTTCATTGCTCCAGAATATGCA

TACAAAATTGTCAAGAAAGGGGACTCAGCAATTGTTAAAAGTGAAGTGGA

ATATGGTAACTGCAACACCAAGTGTCAAACTCCAATAGGGGCGATAAACT

CTAGTATGCCATTCCACAACATACACCCTCTCACCATCGGGGAATGCCCC

AAATATGTGAAATCAAACAAATTAGTCCTTGCGACTGGGCTCAGAAATAG

TCCTCTAAGAGAAGAAGAAGAAAAAGAGGACTATTTGGAGCTATAGCAG

GGTTTATAGAGGGAGGATGGCAGGGAATGGTAGATGGTTGGTATGGGTAC

CACCATAGCAATGAGCAGGGGAGTGGGTACGCTGCAGACAAAGAATCCAC

TCAAAAGGCAATAGATGGAGTCACCAATAAGGTCAACTCGATCATTGACA

AAATGAACACTCAGTTTGAGGCCGTTGGAAGGGAATTTAATAACTTAGAA

AGGAGAATAGAGAATTTAAACAAGAAAATGGAAGACGGATTCCTAGATGT

CTGGACTTATAATGCTGAACTTCTGGTTCTCATGGAAAATGAGAGAACTC

```
-continued
TAGACTTCCATGATTCAAATGTCAAGAACCTTTACGACAAGGTCCGACTA

CAGCTTAGGGATAATGCAAAGGAGCTGGGTAACGGTTGTTTCGAGTTCTA

TCACAAATGTGATAATGAATGTATGGAAAGTGTAAGAAACGGAACGTATG

ACTACCCGCAGTATTCAGAAGAAGCAAGATTAAAAAGAGAGGAAATAAGT

GGAGTAAAATTGGAATCAATAGGAACTTACCAAATACTGTCAATTTATTC

AACAGTTGCGAGTTCTCTAGCACTGGCAATCATGGTGGCTGGTCTATCTT

TGTGGAGAAACCGTAATAGACAATATTAA
```

The amino acid sequence of the chimeric AH/05 HA is set forth herein as SEQ ID NO: 17. The nucleotide and amino acid positions of the gp64 signal sequence, HA ectodomain/transmembrane (TM) domain and gp64 cytoplasmic tail domain of chimeric AH/05 are listed in Table 7 below.

TABLE 7

| Chimeric AH/05 HA | | |
|---|---|---|
| Component | Nucleotides residues of SEQ ID NO: 16 | Amino acid residues of SEQ ID NO: 17 |
| gp64 signal peptide | 1-114 | 1-38 |
| His tag | 115-135 | 39-45 |
| BamHI restriction site | 136-141 | 46-47 |
| HA ectodomain and TM | 142-1755 | 48-585 |
| gp64 cytoplasmic domain | 1756-1779 | 586-592 |

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

The invention claimed is:

1. A recombinant baculovirus vector, comprising a first, second, third and fourth nucleic acid sequence each encoding an influenza hemagglutinin (HA) fusion protein, wherein the first, second, third and fourth nucleic acid sequences each encode an influenza HA with a different amino acid sequence, and wherein each influenza HA fusion protein comprises:
  (i) a baculovirus gp64 signal peptide;
  (ii) an HA ectodomain and transmembrane domain; and
  (iii) a baculovirus gp64 cytoplasmic tail domain.

2. The recombinant vector of claim 1, wherein the first, second, third and fourth nucleic acid sequences are each operably linked to a promoter.

3. The recombinant vector of claim 2, wherein the promoter is the baculovirus polyhedrin promoter.

4. The recombinant vector of claim 1, wherein the first, second, third and fourth nucleic acid sequences each encode:
  (i) an HA from a different influenza A virus;
  (ii) an HA from a different HA subtype;
  (iii) an HA from a different influenza virus clade or subclade;
  (iv) an HA from a different H5N1 influenza virus; or
  (v) an HA from a different clade 2 H5N1 influenza virus.

5. The recombinant vector of claim 1, wherein the first, second, third and fourth nucleic acid sequences each encode an HA from a different H5N1 influenza virus.

6. The recombinant vector of claim 5, wherein the H5N1 influenza virus is selected from a clade 1, clade 2.1, clade 2.2 and clade 2.3 H5N1 influenza virus.

7. The recombinant vector of claim 6, wherein:
  (i) the clade 1 H5N1 influenza virus is A/Vietnam/1203/2004 (VN/04);
  (ii) the clade 2.1 H5N1 influenza virus is A/Indonesia/5/05 (IN/05);
  (iii) the clade 2.2 H5N1 influenza virus is A/Whooper Swan/244/Mongolia/05 (WS/05);
  (iv) the clade 2.3 H5N1 influenza virus is A/Anhui/1/05 HA (AH/05); or
  (v) any combination of two or more of (i) to (iv).

8. The recombinant baculovirus of claim 1, wherein:
  (i) the nucleic acid sequence encoding the gp64 signal peptide comprises nucleotides 1-114 of SEQ ID NO: 10;
  (ii) the nucleic acid sequence encoding the gp64 cytoplasmic tail domain comprises nucleotides 1765-1788 of SEQ ID NO: 10; or
  (iii) both (i) and (ii).

9. The recombinant baculovirus of claim 1, wherein the first, second, third and fourth nucleic acid sequences are at least 95% identical to the nucleic acid sequences of SEQ ID NO: 10, SEQ ID NO: 12, SEQ ID NO: 14 and SEQ ID NO: 16, respectively.

10. An isolated insect cell comprising the vector of claim 1.

11. A recombinant baculovirus displaying a first, second, third and fourth influenza virus HA fusion protein in the baculovirus envelope, wherein each HA fusion protein comprises a different HA amino acid sequence, and wherein each HA fusion protein comprises:
  (i) a baculovirus gp64 signal peptide;
  (ii) an HA ectodomain and transmembrane domain; and
  (iii) a baculovirus gp64 cytoplasmic tail domain.

12. The recombinant baculovirus of claim 11, wherein the first, second, third and fourth HA fusion proteins each comprise an HA amino acid sequence from a different H5N1 influenza virus.

13. The recombinant baculovirus of claim 12, wherein the H5N1 influenza virus is selected from a clade 1, clade 2.1, clade 2.2 and clade 2.3 H5N1 influenza virus.

14. The recombinant baculovirus of claim 13, wherein:
  (i) the clade 1 H5N1 influenza virus is A/Vietnam/1203/2004 (VN/04);
  (ii) the clade 2.1 H5N1 influenza virus is A/Indonesia/5/05 (IN/05);
  (iii) the clade 2.2 H5N1 influenza virus is A/Whooper Swan/244/Mongolia/05 (WS/05);
  (iv) the clade 2.3 H5N1 influenza virus is A/Anhui/1/05 HA (AH/05); or
  (v) any combination of two or more of (i) to (iv).

15. The recombinant baculovirus of claim 11, wherein:
  (i) the amino acid sequence of the gp64 signal peptide comprises amino acid residues 1-38 of SEQ ID NO: 11;
  (ii) the amino acid sequence of the gp64 cytoplasmic tail domain comprises amino acid residues 589-595 of SEQ ID NO: 11; or
  (iii) both (i) and (ii).

16. The recombinant baculovirus of claim 11, wherein the amino acid sequence of the first, second, third and fourth influenza virus HA fusion protein is at least 95% identical to the amino acid sequences of SEQ ID NO: 11, SEQ ID NO: 13, SEQ ID NO: 15 and SEQ ID NO: 17, respectively.

17. A composition comprising the recombinant baculovirus of claim 11 and a pharmaceutically acceptable carrier.

18. A method of eliciting an immune response against influenza virus in a subject, comprising administering a therapeutically effective amount of the recombinant baculovirus of claim 11.

19. The method of claim 18, wherein administration is intramuscular administration.

* * * * *